United States Patent
Nangia et al.

(10) Patent No.: US 9,744,137 B2
(45) Date of Patent: Aug. 29, 2017

(54) TOPIRAMATE COMPOSITIONS AND METHODS OF ENHANCING ITS BIOAVAILABILITY

(75) Inventors: Avinash Nangia, Sharon, MA (US); Daya D. Verma, Edison, NJ (US); Jules Jacob, Taunton, MA (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 1314 days.

(21) Appl. No.: 11/897,940

(22) Filed: Aug. 31, 2007

(65) Prior Publication Data

US 2008/0085306 A1    Apr. 10, 2008

Related U.S. Application Data

(60) Provisional application No. 60/841,924, filed on Aug. 31, 2006.

(51) Int. Cl.
| | |
|---|---|
| A61K 9/22 | (2006.01) |
| A61K 9/28 | (2006.01) |
| A61K 9/16 | (2006.01) |
| A61K 9/20 | (2006.01) |
| A61K 9/48 | (2006.01) |
| A61K 9/50 | (2006.01) |
| A61K 31/357 | (2006.01) |

(52) U.S. Cl.
CPC .......... *A61K 9/2846* (2013.01); *A61K 9/1635* (2013.01); *A61K 9/2013* (2013.01); *A61K 9/2054* (2013.01); *A61K 9/2077* (2013.01); *A61K 9/2086* (2013.01); *A61K 9/4808* (2013.01); *A61K 9/4891* (2013.01); *A61K 9/5073* (2013.01); *A61K 31/357* (2013.01)

(58) Field of Classification Search
CPC ...... A61K 9/20; A61K 9/2004; A61K 9/2077; A61K 9/2095; A61K 9/28; A61K 9/2806; A61K 9/284
USPC ........................................ 424/465, 489, 464
See application file for complete search history.

(56) References Cited

U.S. PATENT DOCUMENTS

| | | | |
|---|---|---|---|
| 2,528,378 A | 10/1950 | Mannheimer et al. |
| 2,675,619 A | 4/1954 | Cone |
| 2,677,700 A | 5/1954 | Jackson et al. |
| 2,781,354 A | 2/1957 | Mannheimer et al. |
| 2,979,578 A | 4/1961 | Curtis |
| 2,996,431 A | 8/1961 | Barry |
| 3,036,118 A | 5/1962 | Jackson et al. |
| 3,139,383 A | 6/1964 | Neville et al. |
| 3,535,307 A | 10/1970 | Moss et al. |
| 3,811,444 A | 5/1974 | Heller et al. |
| 3,829,506 A | 8/1974 | Schmolka et al. |
| 3,962,414 A | 6/1976 | Michaels |
| 3,992,518 A | 11/1976 | Chien et al. |
| 4,066,747 A | 1/1978 | Capozza |
| 4,070,347 A | 1/1978 | Schmitt |
| 4,079,038 A | 3/1978 | Choi et al. |
| 4,083,949 A | 4/1978 | Benedikt |
| 4,093,709 A | 6/1978 | Choi et al. |
| 4,290,426 A | 9/1981 | Luschen et al. |
| 4,434,153 A | 2/1984 | Urquhart et al. |
| 4,513,006 A | 4/1985 | Maryanoff et al. |
| 4,721,613 A | 1/1988 | Urquhart et al. |
| 4,727,064 A | 2/1988 | Pitha |
| 4,752,470 A | 6/1988 | Mehta |
| 4,757,128 A | 7/1988 | Domb et al. |
| 4,853,229 A | 8/1989 | Theeuwes |
| 4,938,763 A | 7/1990 | Dunn et al. |
| 4,997,904 A | 3/1991 | Domb |
| 5,030,447 A | 7/1991 | Joshi et al. |
| 5,133,974 A * | 7/1992 | Paradissis ............ A61K 9/5078 424/451 |
| 5,175,235 A | 12/1992 | Domb et al. |
| 5,180,589 A | 1/1993 | Joshi et al. |
| 5,225,202 A | 7/1993 | Hodges et al. |
| 5,256,440 A | 10/1993 | Appel et al. |
| 5,378,475 A | 1/1995 | Smith et al. |
| 5,478,577 A | 12/1995 | Sackler et al. |
| 5,500,227 A | 3/1996 | Oschlack et al. |
| 5,576,311 A | 11/1996 | Guy |

(Continued)

FOREIGN PATENT DOCUMENTS

| | | |
|---|---|---|
| CN | 1130352 A | 9/1996 |
| WO | WO 93/21906 A1 | 11/1993 |

(Continued)

OTHER PUBLICATIONS

US 6,103,281, 08/2000, DelDuca et al. (withdrawn)
Liu et al., "Preparation, characterization and in vivo evaluation of formulation of baicalein with hydroxypropyl-β-cyclodextrin," International Journal of Pharmaceutics, 2006, 312:137-143.
Notification, International Search Report and Written Opinion of International Search Authority mailed Dec. 8, 2008, in corresponding PCT/US2007/086391 (18 pgs.).
International Search Report and Written Opinion mailed Sep. 2, 2008, in PCT/US2007/19208, 10 pages.
Adin et al., "Topiramate Serum Concentration-to-Dose Ratio," Therapeutic Drug Monitoring, Jun. 2004; 26(3):251-257.

(Continued)

*Primary Examiner* — Micah-Paul Young
(74) *Attorney, Agent, or Firm* — Sunit Talapatra; Foley & Lardner LLP

(57) ABSTRACT

The present invention is directed to pharmaceutical compositions that allow for once-daily or alternate day dosage forms of topiramate. The proposed delayed/extended release single dosage form is equivalent to the immediate-release multiple dose daily regimen, and upon administration, provides steady state blood levels of topiramate. Formulations with increased bioavailability and improved pharmacokinetics are disclosed. A once-a-day administration of topiramate is advantageous over the multiple dose regimen both in terms of patient compliance and reduced adverse events, thus providing better treatment of the conditions for which the topiramate is indicated.

25 Claims, 45 Drawing Sheets

(56) References Cited

U.S. PATENT DOCUMENTS

| | | | |
|---|---|---|---|
| 5,753,693 A | 5/1998 | Shank | |
| 5,760,007 A | 6/1998 | Shank et al. | |
| 5,773,019 A | 6/1998 | Ashton et al. | |
| 5,935,933 A | 8/1999 | Shank et al. | |
| 5,955,096 A | 9/1999 | Santos et al. | |
| 5,985,312 A | 11/1999 | Jacob et al. | |
| 5,998,380 A | 12/1999 | Ehrenberg et al. | |
| 6,123,965 A | 9/2000 | Jacob et al. | |
| 6,156,348 A | 12/2000 | Santos et al. | |
| 6,191,117 B1 | 2/2001 | Kozachuk | |
| 6,197,346 B1 | 3/2001 | Mathiowitz et al. | |
| 6,201,010 B1 | 3/2001 | Cottrell | |
| 6,217,908 B1 | 4/2001 | Mathiowitz et al. | |
| 6,235,311 B1 | 5/2001 | Ullah et al. | |
| 6,248,363 B1 | 6/2001 | Patel et al. | |
| 6,294,192 B1 | 9/2001 | Patel et al. | |
| 6,319,903 B1 | 11/2001 | Carrazana et al. | |
| 6,344,215 B1 | 2/2002 | Bettman et al. | |
| 6,365,187 B2 | 4/2002 | Mathiowitz et al. | |
| 6,368,586 B1 | 4/2002 | Jacob et al. | |
| 6,479,467 B1 | 11/2002 | Buchanan et al. | |
| 6,503,884 B1 | 1/2003 | Ehrenberg et al. | |
| 6,514,531 B1 | 2/2003 | Alaux et al. | |
| 6,524,620 B2 | 2/2003 | Chen et al. | |
| 6,559,293 B1 | 5/2003 | Almarsson et al. | |
| 6,562,865 B1* | 5/2003 | Codd et al. | 514/456 |
| 6,569,463 B2 | 5/2003 | Patel et al. | |
| 6,696,091 B2 | 2/2004 | Thakur et al. | |
| 6,699,840 B2 | 3/2004 | Almarsson et al. | |
| 6,797,283 B1 | 9/2004 | Edgren et al. | |
| 6,923,988 B2 | 8/2005 | Patel et al. | |
| 7,018,609 B2 | 3/2006 | Hwang Pun et al. | |
| 7,195,778 B2 | 3/2007 | Fleshner-Barak et al. | |
| 7,611,722 B2 | 11/2009 | Lerner et al. | |
| 7,737,133 B2 | 6/2010 | Devane et al. | |
| 2002/0044962 A1 | 4/2002 | Cherukuri et al. | |
| 2002/0054907 A1 | 5/2002 | Devane et al. | |
| 2002/0064563 A1* | 5/2002 | Thakur | A61K 9/1676 424/490 |
| 2002/0150616 A1 | 10/2002 | Vandecruys | |
| 2003/0017972 A1 | 1/2003 | Pun et al. | |
| 2003/0064097 A1 | 4/2003 | Patel et al. | |
| 2003/0072802 A1 | 4/2003 | Cutler | |
| 2003/0091630 A1* | 5/2003 | Louie-Helm et al. | 424/468 |
| 2003/0133985 A1 | 7/2003 | Louie-Helm et al. | |
| 2003/0147952 A1* | 8/2003 | Lim et al. | 424/468 |
| 2003/0157173 A1* | 8/2003 | Percel et al. | 424/473 |
| 2003/0166581 A1 | 9/2003 | Almarsson et al. | |
| 2003/0215496 A1 | 11/2003 | Patel et al. | |
| 2003/0216430 A1* | 11/2003 | Kawamura | C07D 401/06 514/312 |
| 2003/0225002 A1 | 12/2003 | Livingstone | |
| 2004/0002462 A1* | 1/2004 | Najarian | 514/23 |
| 2004/0022844 A1 | 2/2004 | Hasenzahl et al. | |
| 2004/0028729 A1* | 2/2004 | Shojaei et al. | 424/452 |
| 2004/0028735 A1 | 2/2004 | Kositprapa | |
| 2004/0052843 A1 | 3/2004 | Lerner et al. | |
| 2004/0053853 A1 | 3/2004 | Almarsson et al. | |
| 2004/0082519 A1 | 4/2004 | Hedner et al. | |
| 2004/0091529 A1 | 5/2004 | Edgren et al. | |
| 2004/0096501 A1 | 5/2004 | Vaya et al. | |
| 2004/0109894 A1 | 6/2004 | Shefer et al. | |
| 2004/0115262 A1 | 6/2004 | Jao et al. | |
| 2004/0122104 A1 | 6/2004 | Hirsh et al. | |
| 2004/0132826 A1 | 7/2004 | Hirsh et al. | |
| 2004/0156901 A1 | 8/2004 | Thakur et al. | |
| 2004/0157785 A1 | 8/2004 | Connor | |
| 2004/0185097 A1 | 9/2004 | Kannan et al. | |
| 2004/0234601 A1 | 11/2004 | Legrand et al. | |
| 2004/0258758 A1 | 12/2004 | Gustow et al. | |
| 2005/0053653 A1 | 3/2005 | Kidane et al. | |
| 2005/0058707 A1 | 3/2005 | Reyes et al. | |
| 2005/0069587 A1 | 3/2005 | Modi et al. | |
| 2005/0106242 A1 | 5/2005 | Yan et al. | |
| 2005/0106247 A1 | 5/2005 | Venkatesh et al. | |
| 2005/0129765 A1 | 6/2005 | Li et al. | |
| 2005/0136108 A1* | 6/2005 | Yam | A61K 9/0004 424/468 |
| 2005/0169982 A1 | 8/2005 | Almarssoo et al. | |
| 2005/0169992 A1 | 8/2005 | Jao et al. | |
| 2005/0175697 A1 | 8/2005 | Edgren et al. | |
| 2005/0191343 A1 | 9/2005 | Liang | |
| 2005/0220596 A1 | 10/2005 | Gaedy et al. | |
| 2006/0018933 A1 | 1/2006 | Vaya et al. | |
| 2006/0018934 A1 | 1/2006 | Vaya et al. | |
| 2006/0024365 A1 | 2/2006 | Vaya et al. | |
| 2006/0034927 A1 | 2/2006 | Casadevall et al. | |
| 2006/0045912 A1* | 3/2006 | Truog | 424/468 |
| 2006/0078609 A1 | 4/2006 | Vandecruys et al. | |
| 2006/0105045 A1 | 5/2006 | Buchanan et al. | |
| 2006/0121112 A1* | 6/2006 | Jenkins | A61K 9/5084 424/468 |
| 2006/0147527 A1 | 7/2006 | Bachmann et al. | |
| 2006/0223762 A1 | 10/2006 | Ehrenberg et al. | |
| 2006/0233892 A1 | 10/2006 | Hendrix | |
| 2007/0212411 A1 | 9/2007 | Fawzy et al. | |
| 2008/0085306 A1 | 4/2008 | Nangia et al. | |
| 2008/0118557 A1 | 5/2008 | Liang et al. | |
| 2008/0131501 A1 | 6/2008 | Liang et al. | |

FOREIGN PATENT DOCUMENTS

| | | |
|---|---|---|
| WO | WO 01/37808 A1 | 5/2001 |
| WO | WO 02/03984 A2 | 1/2002 |
| WO | WO 02/043731 A3 | 6/2002 |
| WO | WO-2004/002427 A2 | 1/2004 |
| WO | WO 2004/022037 A1 | 3/2004 |
| WO | WO 2004/078162 A1 | 9/2004 |
| WO | WO 2004/078163 A2 | 9/2004 |
| WO | WO 2005/030166 A1 | 4/2005 |
| WO | WO 2005/079748 A2 | 9/2005 |
| WO | WO 2006/009403 A1 | 1/2006 |
| WO | WO-2006/075925 A2 | 7/2006 |
| WO | WO 2006/119153 A2 | 11/2006 |
| WO | WO 2007/002318 | 1/2007 |

OTHER PUBLICATIONS

Bahk et al., "Topiramate and divalproex in combination with risperidone for acute mania: a randomized open-label study," Progress in Neuropsychopharmacology & Biological Psychiatry, 2005, 29(1):115-121.

Beaumanoir, Anne, "The Landau-Kleffner syndrome", In: Roger et al., Eds. *Epileptic Syndromes in Infancy, Childhood, and Adolescence*, 2nd Ed., London, England: John Libby, pp. 231-244, 1992.

Berge et al., "Pharmaceutical Salts", J. Pharm. Sci., Jan. 1977, 66(1): 1-19.

Berlant, Jeffery L., M.D., Ph.D., "Topiramate in Posttraumatic Stress Disorder: Preliminary Clinical Observations," J. Clin. Psychiatry, 2001, 62(Suppl 17):60-63.

Brandes et al., "Topiramate for Migraine Prevention," JAMA, Feb. 25, 2004, 291(8):965-973.

Carpenter et al., "Do obese depressed patients respond to topiramate? A retrospective chart review," J. Affect. Disord., 2002, 69(1-3):251-255.

Chen et al., "Combination Treatement of Clozapine and Topiramate in Resistant Rapid-Cycling Bipolar Disorder," Clin. Neuropharmacol., May-Jun. 2005, 28(3):136-138.

Coleman et al., "Polymer reviewed: A practical guide to polymer miscibility," Jul. 1990, 31:1187-1230.

Contin et al., "Topiramate Therapeutic Monitoring in Patients with Epilepsy: Effect of Concomitant Antiepileptic Drugs," Ther. Drug Monit., 2002, 24(3):332-337.

D'Amico et al., "Topiramate in migraine prophylaxis," Neurological Sciences, 2005, 26(Suppl 2):S130-S133.

Deckers et al., "Selection of Antiepileptic Drug Polytherapy Based on Mechanisms of Action: The Evidence Reviewed," Epilepsia, 2000, 41(11):1364-1374.

Diener et al., "Topiramate in migrain prophylaxis: Results from a placebo-controlled trail with propranolol as an active control," J. Neurol., 2004, 251(8):943-950.

(56) References Cited

OTHER PUBLICATIONS

Dorado et al., "Topiramato en enfermedades comorbidas: epilepsia y migrana," Rev. Neurol., 2006, 43(4):193-196.

Duchene et al., "Pharmaceutical and Medical Aspects of Bioadhesive Systems for Drug Administration," Drug Dev. Ind. Pharm., 1988, 14(2&3):283-318.

Erfurth et al., "Bupropion as Add-On Strategy in Difficult-to-Treat Bipolar Depressive Patients," Neuropsychobiology, 2002, 45(Suppl 1):33-36.

Felmeister, Alvin Ph.D., "Powders," Remington's Pharm. Sci., 14th Ed., 1970, Chapter 86, 1626-1628.

Ferrari et al., "Influence of Dosage, Age, and Co-Medication on Plasma Topiramate Concentrations in Children and Adults with Severe Epilepsy and Preliminary Observations on Correlations with Clinical Response," Therapeutic Drug Monitoring, 2003, 25(6):700-708.

Ferrari et al., "Rizatriptan: a new milestone in migraine treatment," Cephalalgia, 2000, 20(Suppl 1):1.

Fincher, Julian H., "Particle Size of Drugs and Its Relationship to Absorption and Activity," J. Pharm. Sci., Nov. 1968, 57(11):1825-1835.

Fisher et al., "Synergism between Topiramate and Budipine in Refractory Status Epilepticus in the Rat," Epilepsia, 2004, 45(11):1300-1307.

François et al., "The combination of topiramate and diazepam is partially neuroprotective in the hippocampus but not antiepileptogenic in the lithium-pilocarpine model of temporal lobe epilepsy," Epilepsy Research, 2006, 72:147-163.

Gurny et al., "Bioadhesive intraoral release systems: design, testing and analysis," Biomaterials, Nov. 1984, 5:336-340.

Hershey et al., "Effectiveness of Topiramate in the Prevention of Childhood Headaches," Headache, Sep. 2002;42(8):810-818.

Hoes et al., "The Application of Drug-Polymer Conjugates in Chemotherapy," Drug Carrier Systems, 1989, 9:57-109.

Hollander et al., "Topiramate plus paroxetine in treatment-resistant obsessive-compulsive disorder," Int. Clin. Psychopharmacol., 2006, 21(3): 189-191.

Ioannides-Demos et al., "Pharmacotherapy for Obesity," Drugs, 2005, 65(10):1391-1418.

Johnson et al., "Oral topiramate for treatmetn of alcohol dependence: a randomised controlled trial," The Lancet, May 17, 2003, 361(9370):1677-1685.

Kellett et al., "Topiramate in clinical practice: first year's postlicensing experience in a specialist epilepsy clinic," J. Neurol. Neurosurg. and Psych., 1999;66:759-763.

Lainez et al., "Topiramate in the Prophylactic Treatment of Cluster Headache," Headache, Jul./Aug. 2003, 43(7):784-789.

Lalonde et al., "Additive effects of leptin and topiramate in reducing fat deposition in lean and obese ob/ob mice," Physiology & Behavior, 2004, 80(4):415-420.

Lee et al., "The Effects of Adjunctive Topiramate on Cognitive Function in Patients with Epilepsy," Epilepsia, 2003; 44(3):339-347.

Lehr et al., "Intestinal Transit of Bioadhesive Microspheres in an in situ Loop in the Rat—A Comparative Study with Copolymers and Blends Based on Poly(acrylic acid)," Journal of Controlled Release, 1990, 13:51-62.

Leong et al., "Polymeric controlled drug delivery," Adv. Drug Delivery Rev., 1987, 1:199-233.

Linhardt, Robert J. "Biodegradable Polymers for Controlled Release of Drugs," Controlled Release of Drugs, 1989, Chapter 2, 53-95.

Longer, Mark A., Ph.D., "Sustained-Release Drug Delivery Systems," Remington's Pharmaceutical Sciences, 18th Edition, 1990, Chapter 91, 1676-1693.

Lu et al., "Dimensionless presentation for drug release from a coated pure drug bead: 1. Analysis," Inter. J. of Pharm., 1994, 112:105-116.

Lu et al., "Dimensionless presentation for drug release from a coated pure drug bead: 2. Experiment," Inter. J. of Pharm., 1994, 112:117-124.

Luszczki et al., "Interactions of Lamotrigine with Topiramate and First-Generation Antiepileptic Drugs in the Maximal Electroshock Test in Mice: An Isobolographic Analysis," Epilepsia, 2003, 44(8):1003-1013.

Mathew et al., "Prophylaxis of Migraine, Transformed Migraine, and Cluster Headache with Topiramate," Headache, Sep. 2002, 42(8):796-803.

McElroy et al., "Topiramate in the Treatment of Binge Eating Disorder Associated with Obesity: A Randomized, Placebo-Controlled Trial," Am. J. Psychiatry, Feb. 2003, 160(2):255-261.

Meador et al., "Cognitive and behavioral effects of lamotrigine and topiramate in healthy volunteers," Neurology, Jun. 2005, 64:2108-2114.

Mikos et al., "Interaction of Polymer Microspheres with Mucin Gels as a Means of Characterizing Polymer Retention on Mucus," Journal of Colloid and Interface Science, May 1991, 143(2): 366-373.

Morton et al., "Diagnosis and treatment of epilepsy in children and adolescents", Drugs, Mar. 1996, 51(3):399-414.

Mosek et. al., "Topiramate in the treatment of refractory chronic daily headache. An open trial," Journal of Headache and Pain, 2005, 6:77-80.

O'Connor et al., "Powders," Remington's Pharmaceutical Sciences, 18th Edition, 1990, Chapter 88, 1615-1632.

Park et al., "Alternative Approaches to Oral Controlled Drug Delivery: Bioadhesives and In-Situ Systems," Recent Advances in Drug Delivery, Plenum Press, New York, 1984, 163-183.

Pascual et al., "Testing the combination beta-blocker plus topiramate in refractory migraine," Acta Neurol. Scand., 2007, 115(2):81-83.

Physicians' Desk Reference 59th edition, 2541-2548 (2005).

Physician's Desk Reference, 60$^{th}$ Edition, 2006, pp. 2438-2447, entry for TOPAMAX®.

Physician's Desk Reference, 56th ed., 2590-2595 (2002).

Pies, Ronald M.D., "Combining Lithium and Anticonvulsants in Bipolar Disorder: A Review," Annals of Clinical Psychiatry, Dec. 2002, 14(4):223-232.

Porter, Stuart C., Ph.D., "Coating of Pharmaceutical Dosage Forms," Remington's Pharmaceutical Sciences, 18th Edition, 1990, Chapter 90, 1666-1675.

Potter et al., "A Double-Blind, Randomized, Placebo-Controlled, Parallel Study to Determine the Efficacy of Topiramate in the Prophylactic Treatment of Migraine," Neurology, Apr. 2000, 54(Suppl 3):A15.

Rudnic et al., "Oral Solid Dosage Forms," Remington's Pharmaceutical Sciences, 18th Edition, 1990, Chapter 89, 1633-1665.

Silberstein et al., "Topiramate in Migraine Prevention," Arch. Neurol., Apr. 2004, 61(4):490-495.

Siniscalchi et al., "Combined topiramate and declorazepam therapy in a patient affected by essential tremor," Parkinsonism Relat. Disord., 2007, 13(2):129-130.

Smart et al., "An in-vitro investigation of mucosa-adhesive materials for use in controlled drug delivery," J. Pharm. Pharmacol., 1984, 36:295-299.

Sofuoglu et al., "Effects of topiramate in combination with intravenous nicotine in overnight abstinent smokers," Psychopharmacology, 2006, 184(3-4): 645-651.

Storey et al., "Topiramate in Migraine Prevention: A Double-Blind Placebo-Controlled Study," Headache, Nov./Dec. 2001, 41(10):968-975.

Thompson et al., "Effects of topiramate on cognitive function," J. Neurol. Neurosurg and Psych., 2000; 69:634-641.

Toplak et al., "Efficacy and safety of topiramate in combination with metformin in the teratment of obese subjects with type 2 diabetes: a randomized, double-blind placebo-controlled study," Int. J. Obes., 2007, 31(1):138-146.

Von Seggern et al., "Efficacy of Topiramate in Migraine Prophylaxis: A Retrospective Chart Analysis," Neurology, Apr. 2000, 54(Suppl 3):A267-A268.

(56) References Cited

OTHER PUBLICATIONS

Weber, Marcus Vinicius Keche, M.D., "Topiramate for Obstructive Sleep Apnea and Snoring," Am. J. Psychiatry, May 2002, 159(5):872-873.

Winkelman, John W., "Treatement of nocturnal eating syndrome and sleep-related eating disorder with topiramate," Sleep Medicine, 2003, 4(3):243-246.

* cited by examiner

1. Slow Eroding Active Core
2. Insoluble Plug
3. Enteric Polymeric Plug
4. Impermeable Polymeric Cylinder 1. Slow Eroding Active Core
3. Enteric Polymeric Plug
4. Impermeable Polymeric Cylinder 1. Slow Eroding Active Core
2. Insoluble Plug
3. Enteric Polymeric Plug
4. Impermeable Polymeric Cylinder
5. Immediate Release Active Core 6. Immediate Release Beads/Pellets 7. Controlled Release Beads/Pellets 8. Hard Gelatin Capsule 9. Enteric Coating 9. Enteric Coating
10. Immediate Release Active Layer
11. Controlled Release Active Layer 9. Enteric Coating
12. Slow Eroding or Non-eroding Active Matrix Core 9. Enteric Coating 10. Immediate Release Active Core 11. Controlled Release Active Core 13. Rate Controlling Coating 9. Enteric Coating
14. Active Core
15. Orifice
16. Semi-permeable Coating 14. Active Core
15. Orifice
16. Semi-permeable Coating
17. Push Layer
18. Time-delay Layer 6. Immediate Release Beads 7. Controlled Release Beads 19. Enteric Polymer Material - (along with compression enhancers and fillers)

6. Immediate Release Beads

20. Controlled Release Beads (Optionally Coated with Bioadhesive Polymer)

21. Bioadhesive Delayed and Extended Release Beads Release Beads

22. Compression Enhancers and Fillers

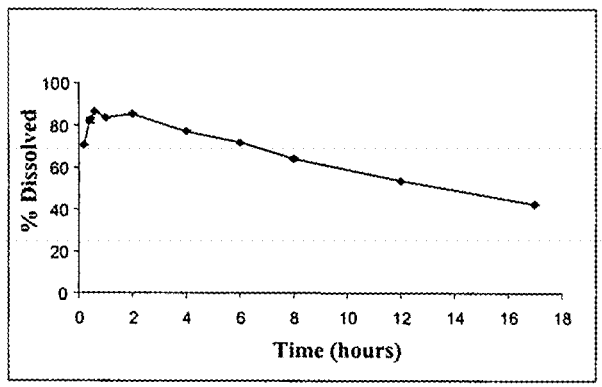
Fig. 2A. Degradation of Topamax® tablets in 0.1N HCl at 37°C
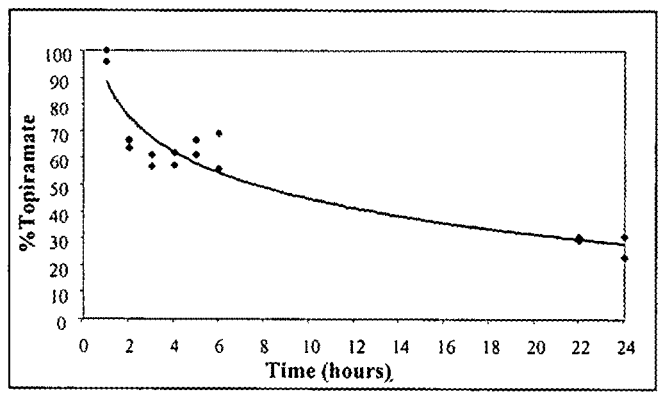
Fig. 2B. Degradation of topiramate in 0.1N HCl at 37°C
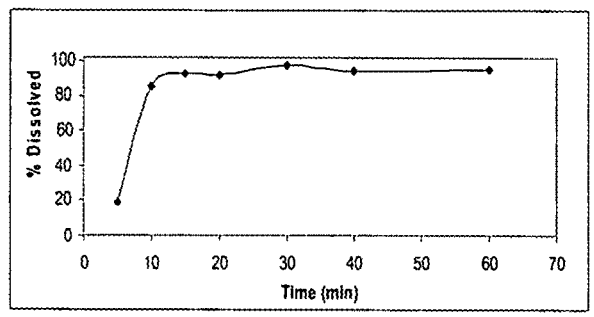
Fig. 2C. Dissolution profile of Topamax® tablets in phosphate buffer pH=6.8

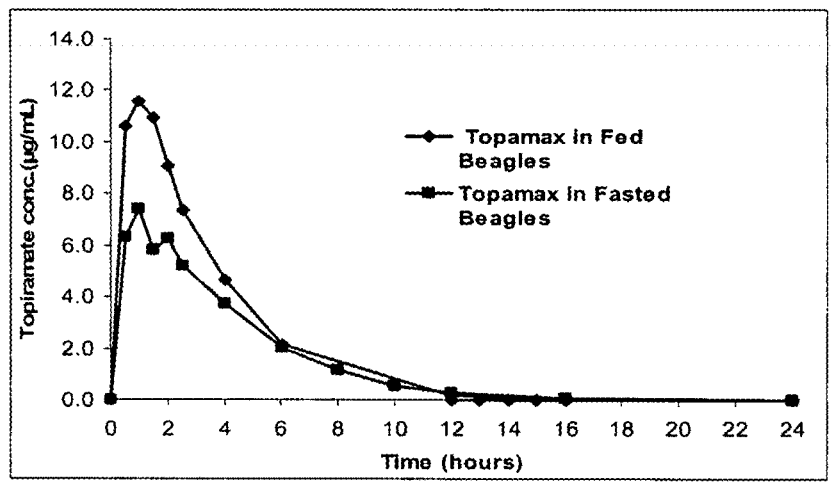
Fig. 3. Plasma concentration v time profile of Topamax® ® tablets (100 mg) in fed and fasted beagles

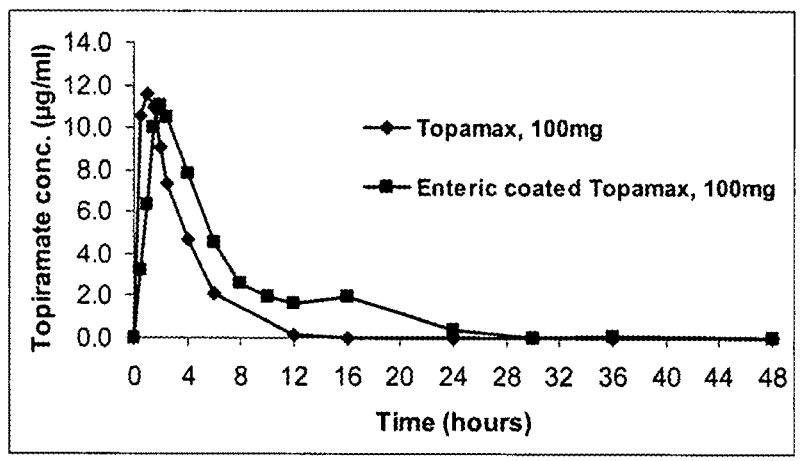
Fig. 4. Pharmacokinetic profiles of Topamax® tablets (100 mg) and enteric-coated, delayed-release Topamax® tablets (100 mg) in fed beagles

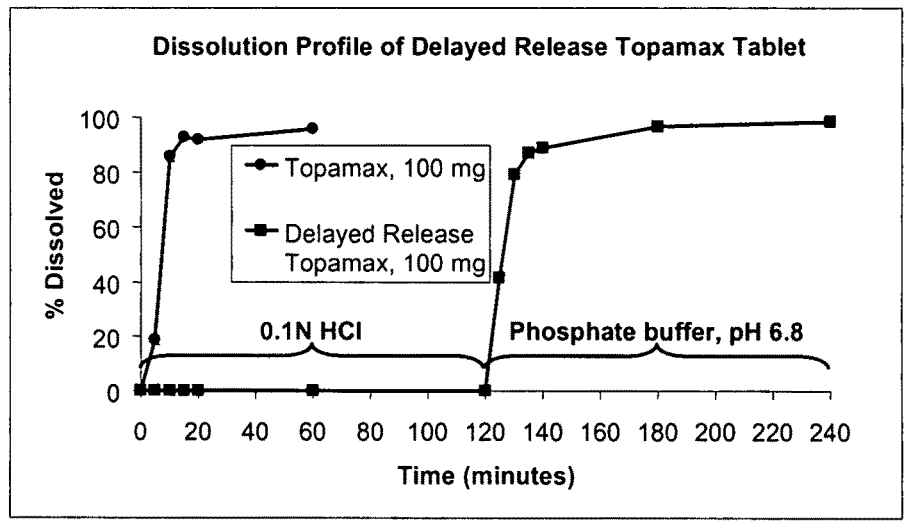
Fig. 5A. Dissolution profiles of Topamax® tablets (100 mg) and enteric-coated, delayed-release Topamax® tablets (100 mg)
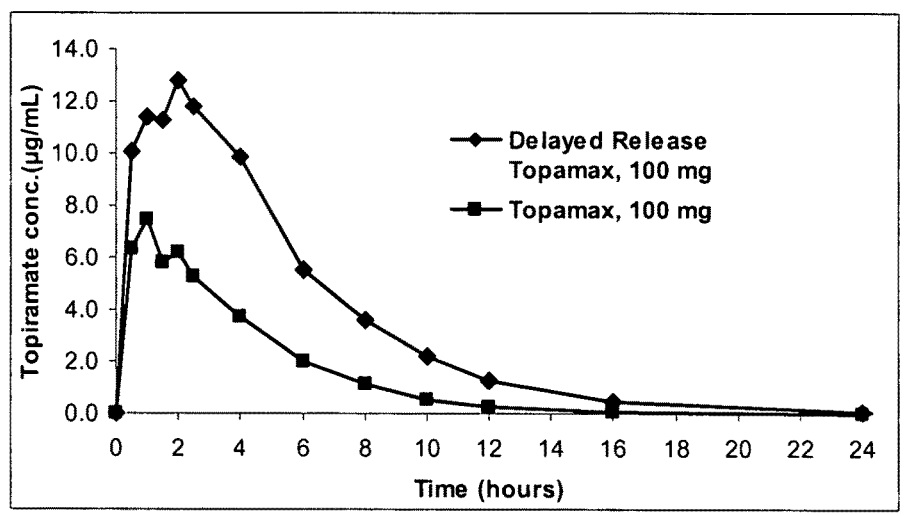
Fig. 5B. Pharmacokinetic profiles of Topamax® tablets (100 mg) and delayed-release topamax®® tablets (100 mg) in fasted beagles

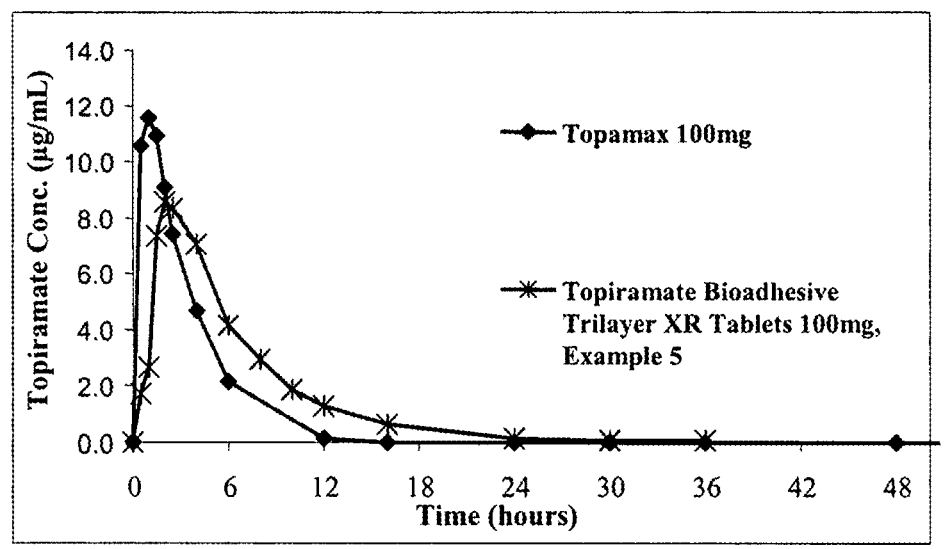
Fig. 6. Pharmacokinetic profiles of Topamax® tablets (100 mg) and topiramate bioadhesive trilayer XR tablets (100mg) Example 5, in fed beagles

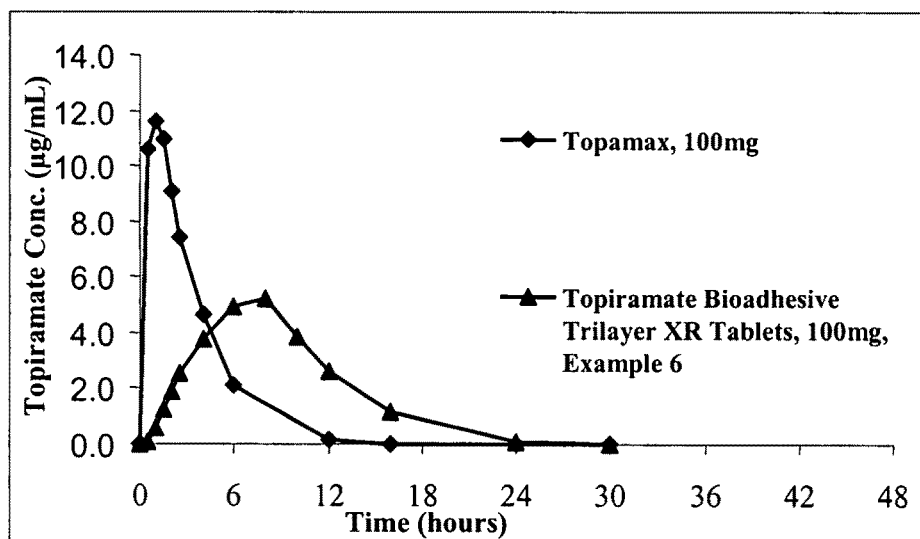
Fig. 7. Pharmacokinetic profiles of Topamax® tablets, 100 mg and topiramate bioadhesive trilayer XR tablets 100mg, Example 6, in fed beagles

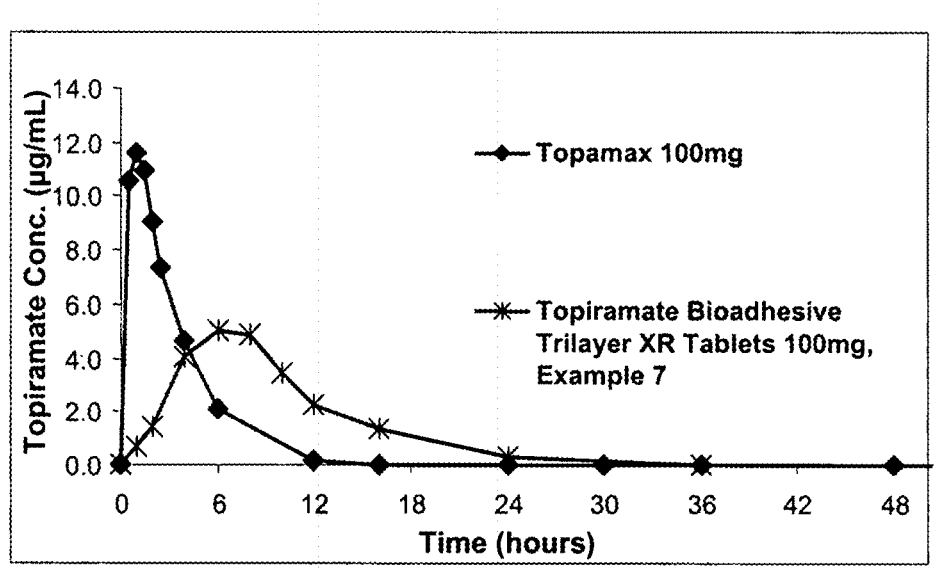
Fig. 8. Pharmacokinetics profiles of Topamax® tablets, 100 mg and topiramate bioadhesive trilayer XR tablets 100mg, Example 7, in fed beagles

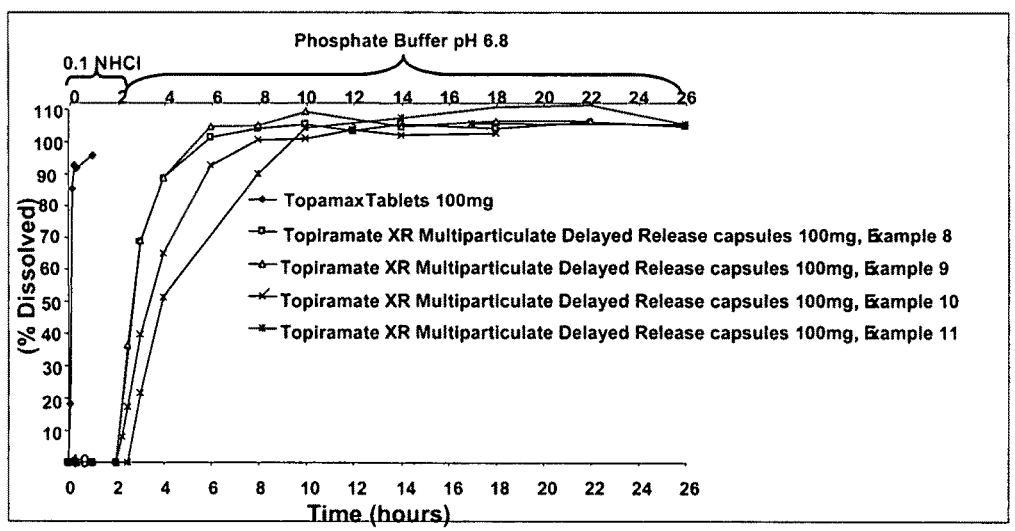
Fig. 9. Dissolution profiles of Topamax® tablets (100 mg) and topiramate bioadhesive delayed and extended-release multiparticulates formulations (100 mg) (Examples 8-11)

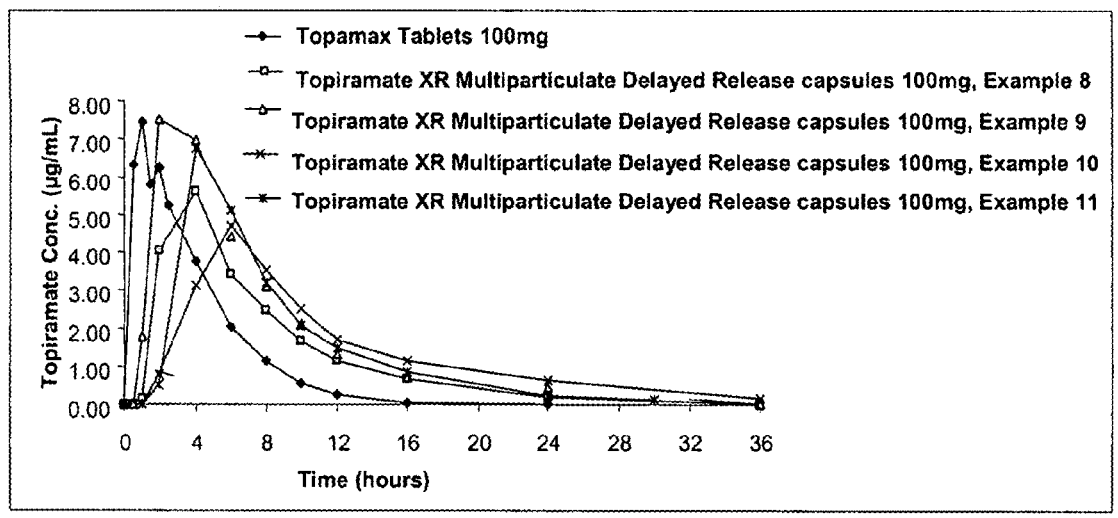
Fig. 10. Pharmacokinetic profiles of Topamax® tablets, 100 mg and topiramate bioadhesive delayed and extended release multiparticulate formulations, 100mg (Examples 8-11)

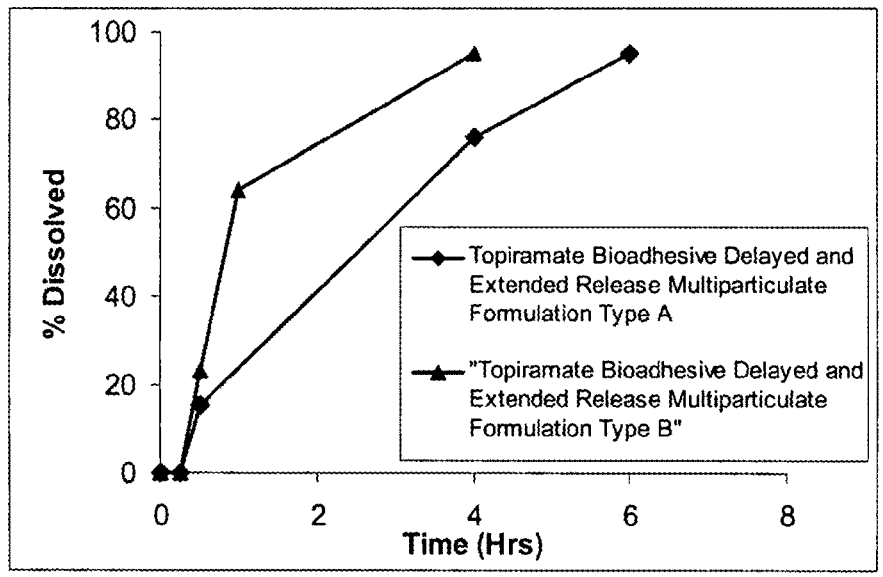

Fig. 11A. Dissolution profile of topiramate bioadhesive delayed and extended release multiparticulate capsules, 100 mg Type A and Type B in ammonium phosphate buffer, pH 6.8 at 37°C

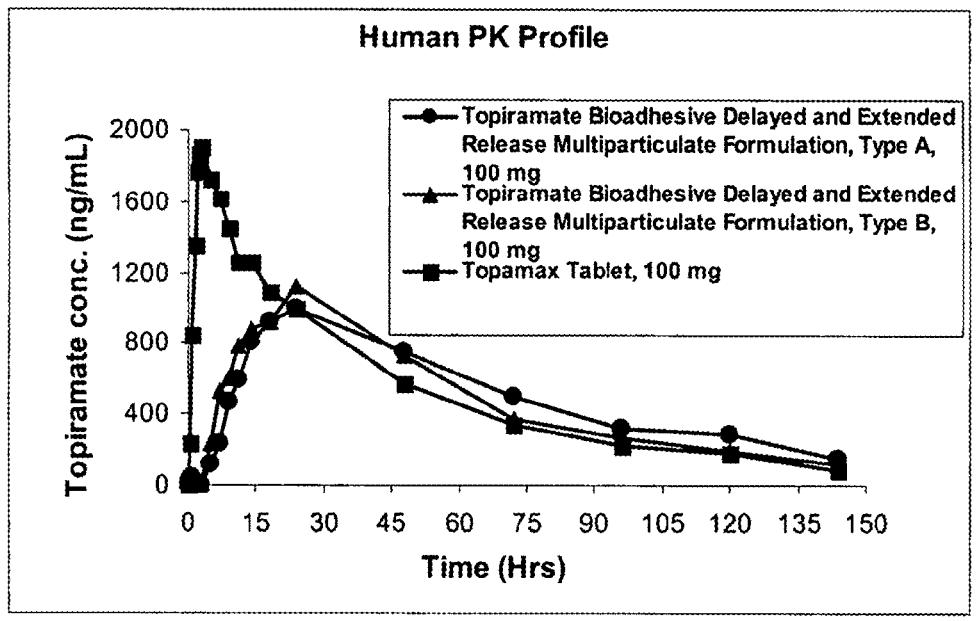

Fig. 11B. Topiramate plasma concentration time profiles after administration of a single dose of 100 mg topiramate bioadhesive delayed and extended release multiparticulate formulations Type A and Type B, and Topamax® tablets, 100 mg in healthy human volunteers

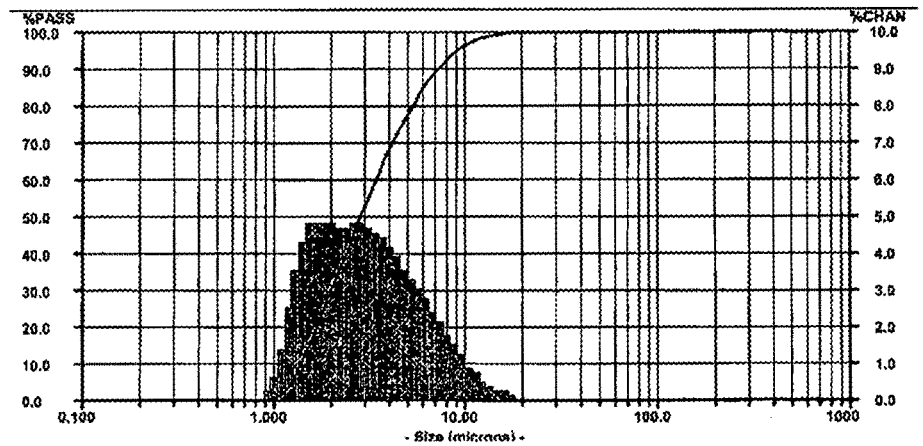
Fig. 12A. Particle size analysis of micronized topiramate.
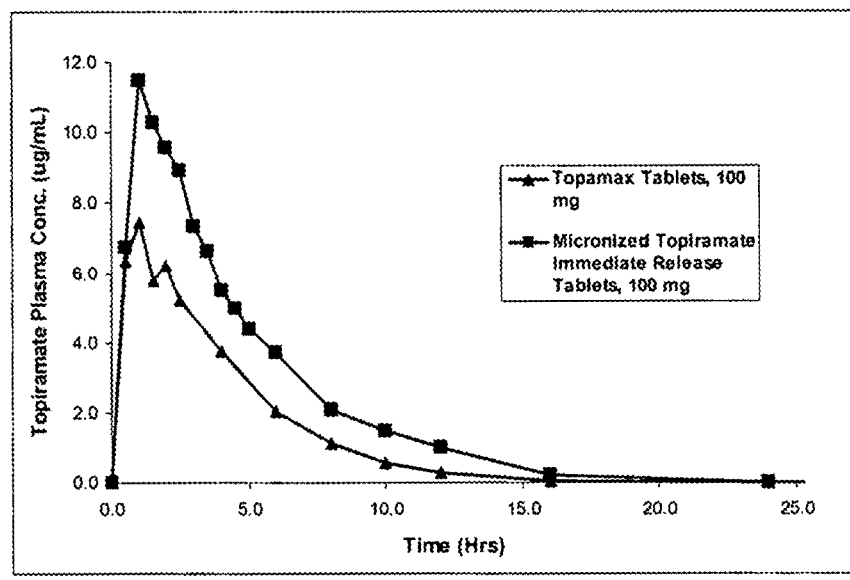
Fig. 12B. Topiramate plasma profiles of Topamax®, 100 mg and micronized topiramate immediate release tablets, 100mg in fasted beagles

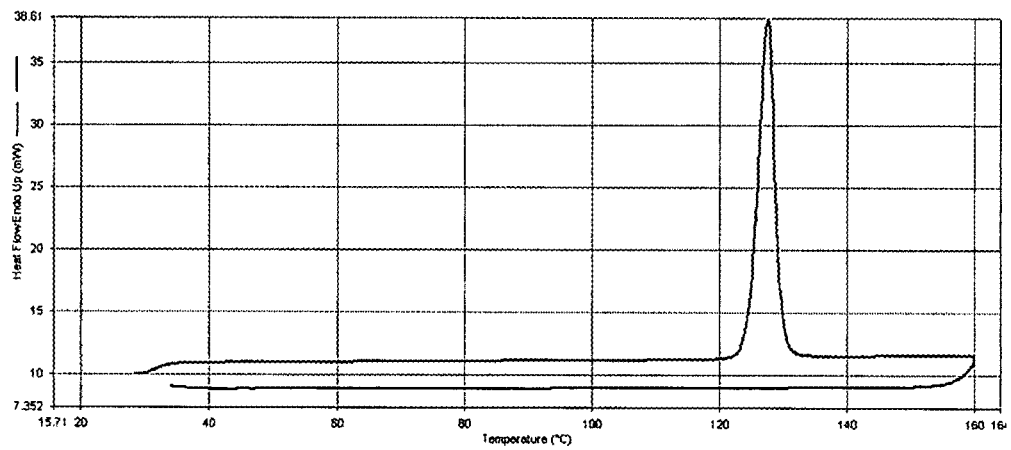
Fig. 13A. DSC scans of crystalline topiramate
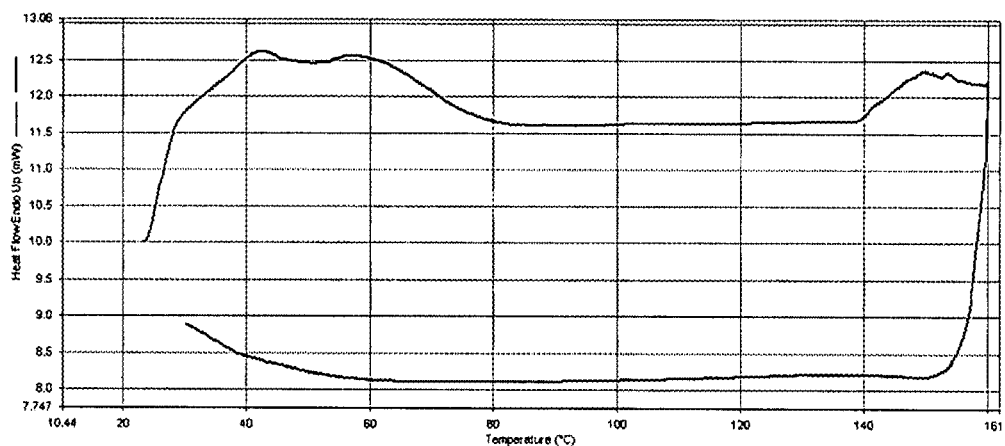
Fig. 13B. DSC scans of spray-dried amorphous topiramate

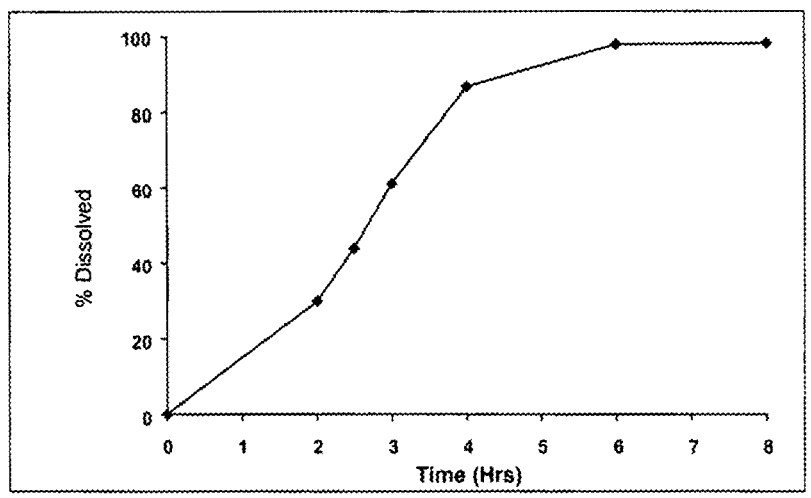
Fig. 14. Dissolution profile of topiramate rapidly disintegrating XR pelletized tablet, 100 mg, in 0.1 N HCl (0-2 hrs) followed by ammonium phosphate buffer (2-8 hrs), pH 6.8 at 37°C

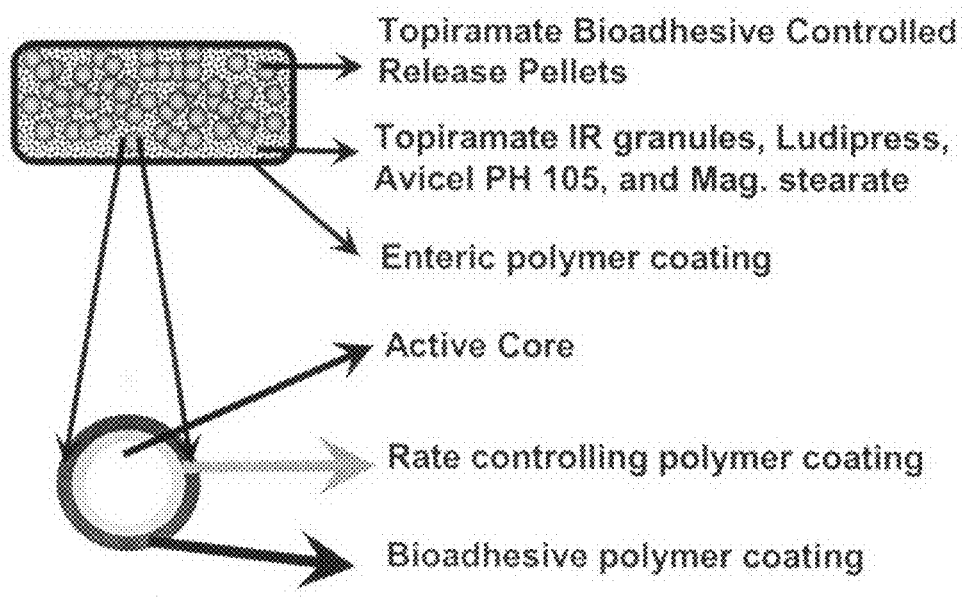
Fig. 15. Schematic design of topiramate delayed release rapidly disintegrating XR pelletized tablet

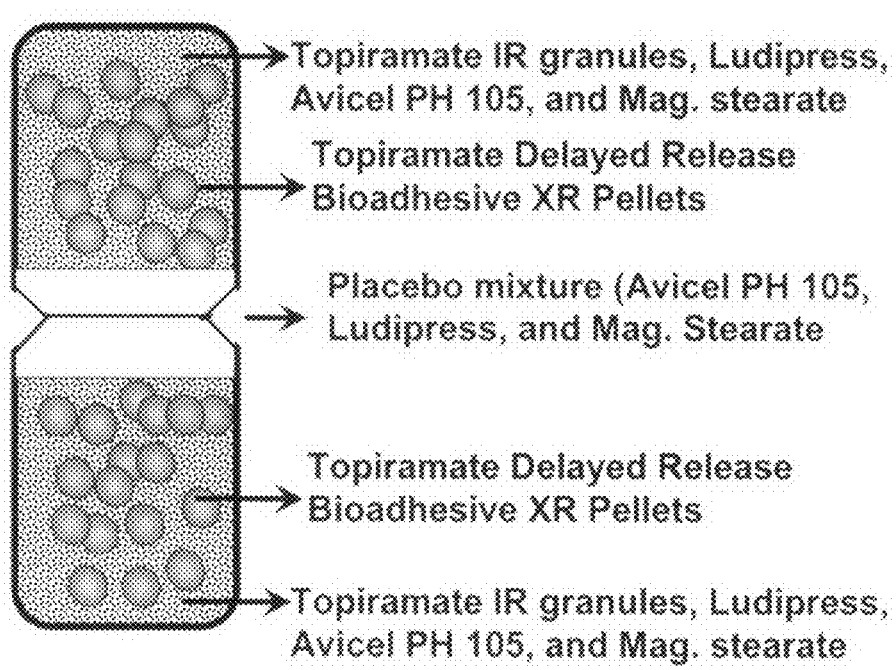
Fig. 16. Schematic design of topiramate rapidly disintegrating extended release (XR) pelletized tablets, 100 mg with split function

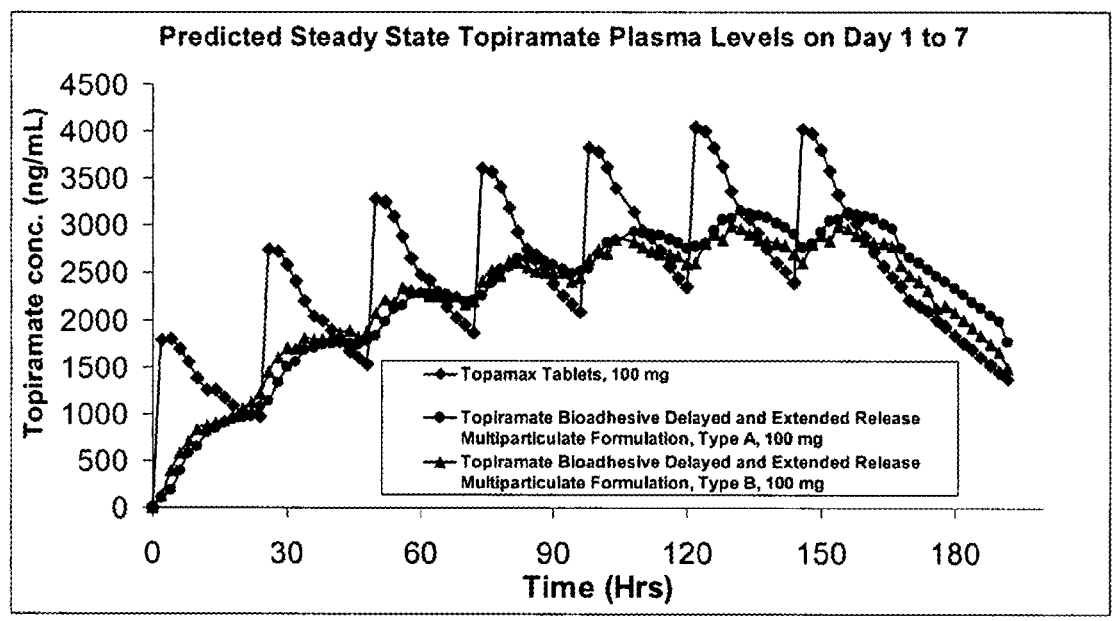
Figure 17A. Predicted steady state topiramate plasma levels in healthy volunteers from day 1 to day 7 of dosing of 100 mg bioadhesive delayed release topiramate XR multiparticulate formulations Type A and Type B and an equivalent dose of Topamax® tablets

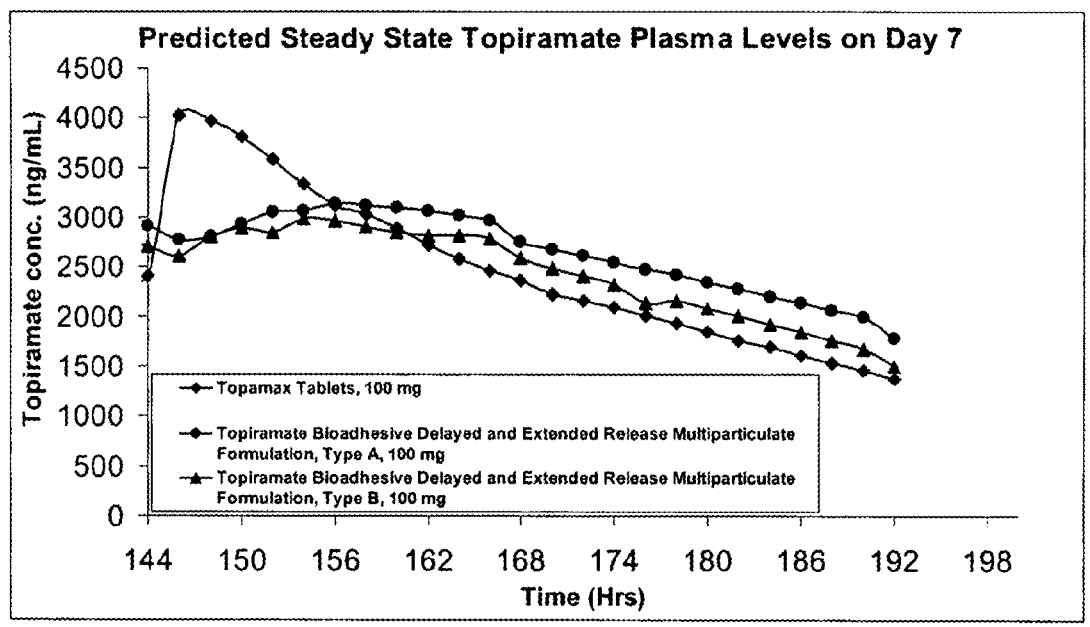
Figure 17B. Predicted steady state topiramate plasma levels in healthy volunteers following the last dose (day 7) of 100 mg bioadhesive delayed release topiramate XR multiparticulate formulations Type A and Type B and an equivalent dose of Topamax® tablets.

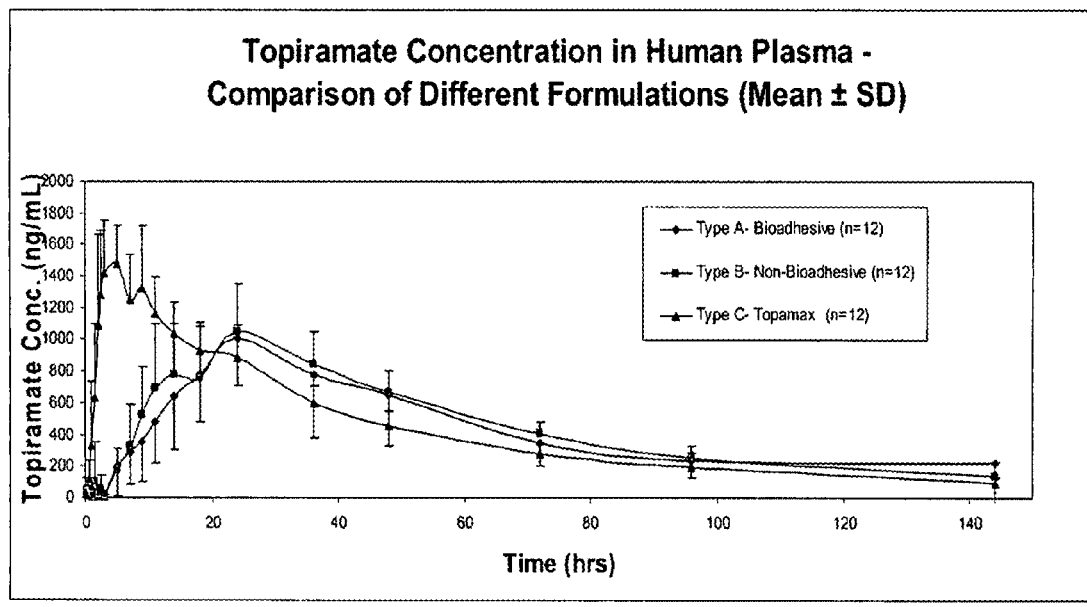
Fig. 18. Topiramate plasma concentration time profiles after administration of a single dose of 100mg topiramate bioadhesive delayed XR capsule, 100mg 100mg topiramate non-bioadhesive delayed XR capsule and Topamax tablets, 100mg in healthy human volunteers

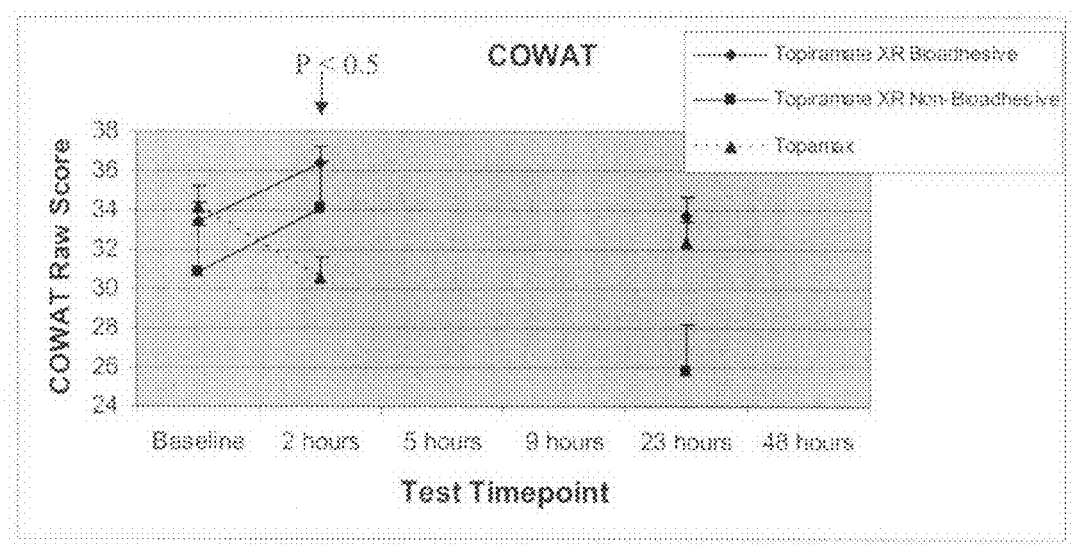
Fig. 19. Performance on the COWAT test at various time intervals after administration of a single dose of 100mg topiramate bioadhesive delayed XR capsule, 100mg 100mg topiramate non-bioadhesive delayed XR capsule and Topamax tablets, 100mg in healthy human volunteers
* 5 hour, 9 hour and 48 hour measurements were not performed to reduce practice effect.

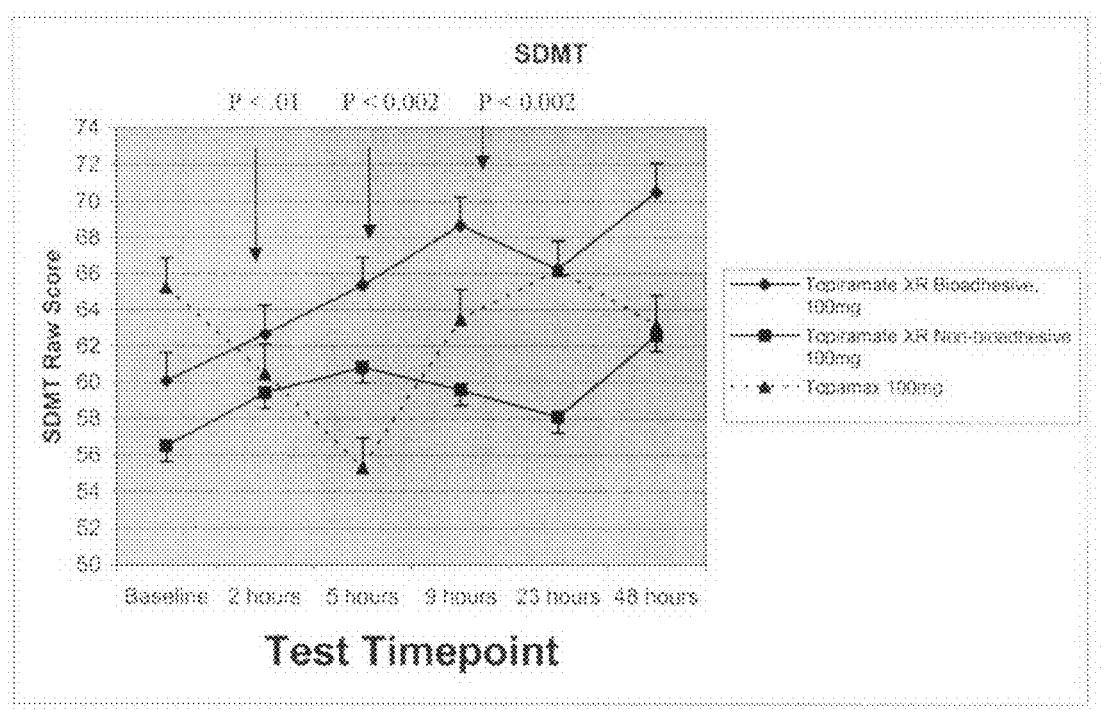
Fig. 20. Performance on the SDMT test at various time intervals after administration of a single dose of 100mg topiramate bioadhesive delayed XR capsule, 100mg 100mg topiramate non-bioadhesive delayed XR capsule and Topamax tablets, 100mg in healthy human volunteers

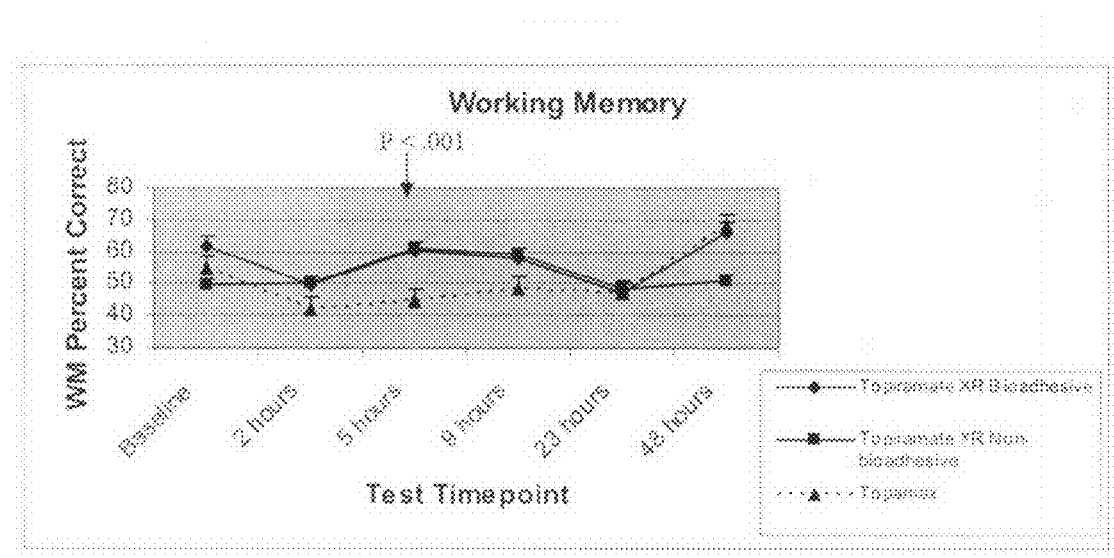
Fig. 21. Performance on the CNTB (working memory module) at various time intervals after administration of a single dose of 100mg topiramate bioadhesive delayed XR capsule, 100mg 100mg topiramate non-bioadhesive delayed XR capsule and Topamax tablets, 100mg in healthy human volunteers

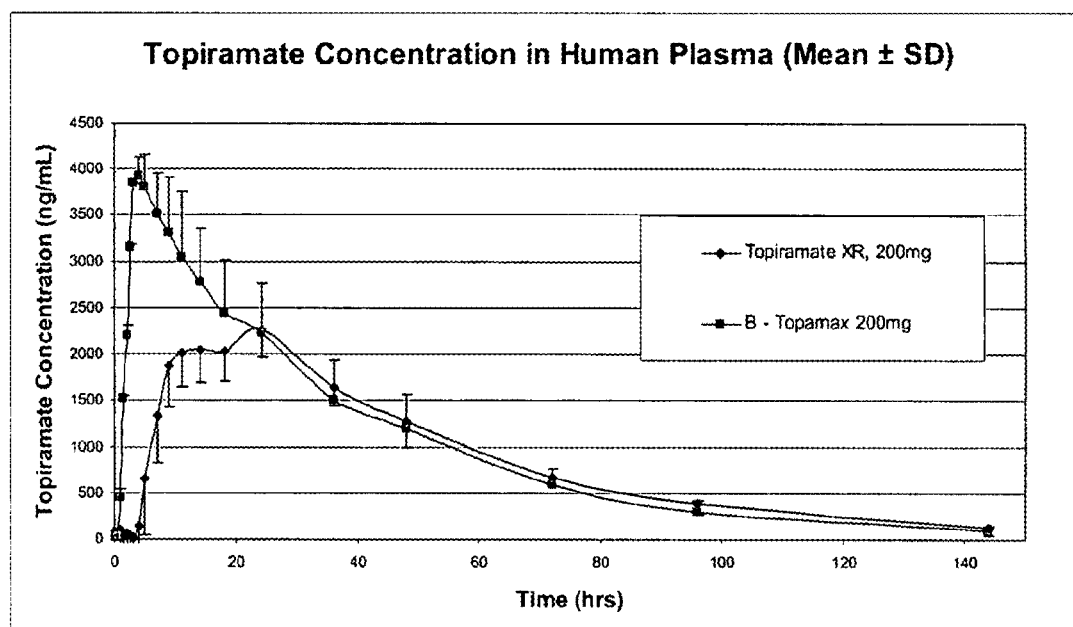
Fig. 22. Topiramate plasma concentration time profiles after administration of a single dose of 200mg (2x100mg) topiramate delayed XR capsule and Topamax tablets, 200mg (two capsules, each capsule containing 4 x 25mg tablets) in healthy human volunteers

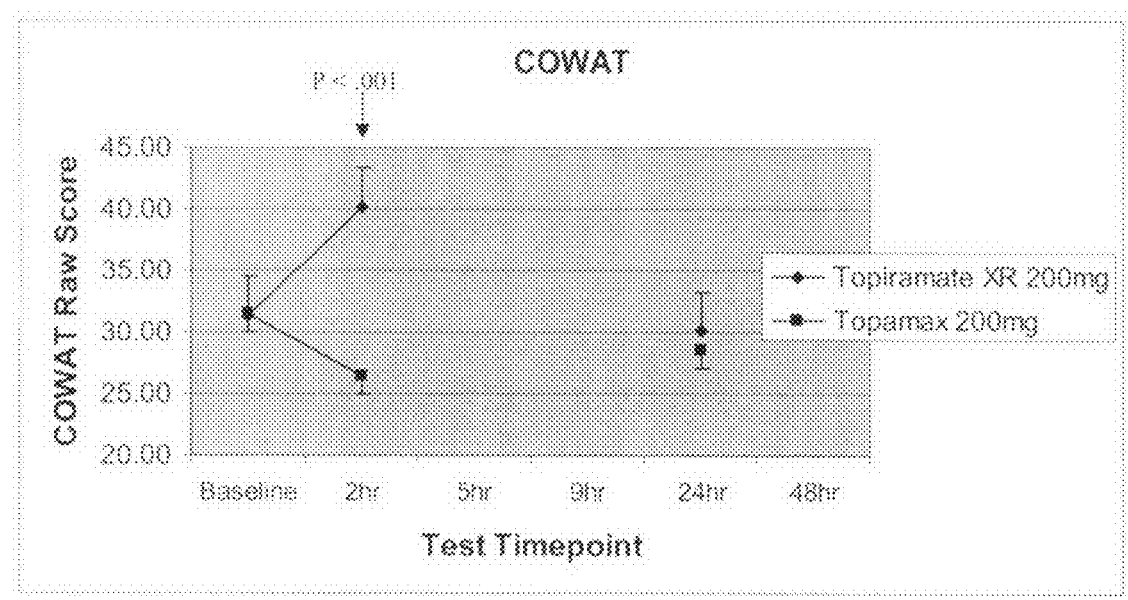
Fig. 23. Performance on the COWAT test at various time intervals after administration of a single dose of 200mg (2x100mg) topiramate delayed XR capsule and Topamax tablets, 200mg (two capsules, each capsule containing 4 x 25mg tablets) in healthy human volunteers
* 5 hour, 9 hour and 48 hour measurements were not performed to reduce practice effect.

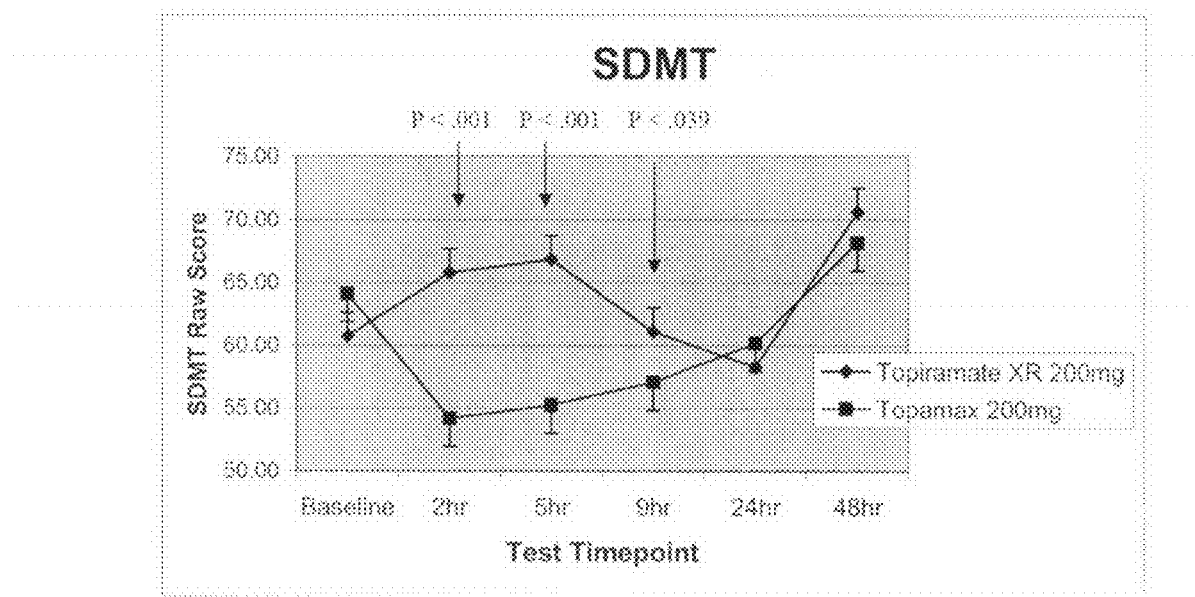
Fig. 24. Performance on the SDMT test at various time intervals after administration of a single dose of 200mg (2x100mg) topiramate delayed XR capsule and Topamax tablets, 200mg (two capsules, each capsule containing 4 x 25mg tablets) in healthy human volunteers

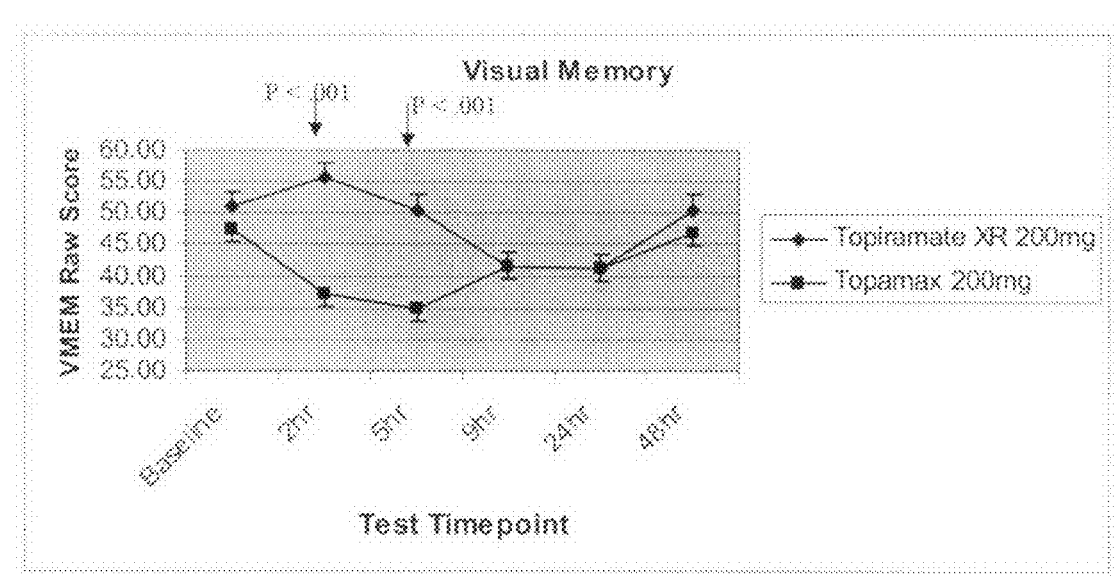
Fig. 25. Performance on the CNTB (visual memory module) at various time intervals after administration of a single dose of 200mg (2x100mg) topiramate delayed XR capsule and Topamax tablets, 200mg (two capsules, each capsule containing 4 x 25mg tablets) in healthy human volunteers

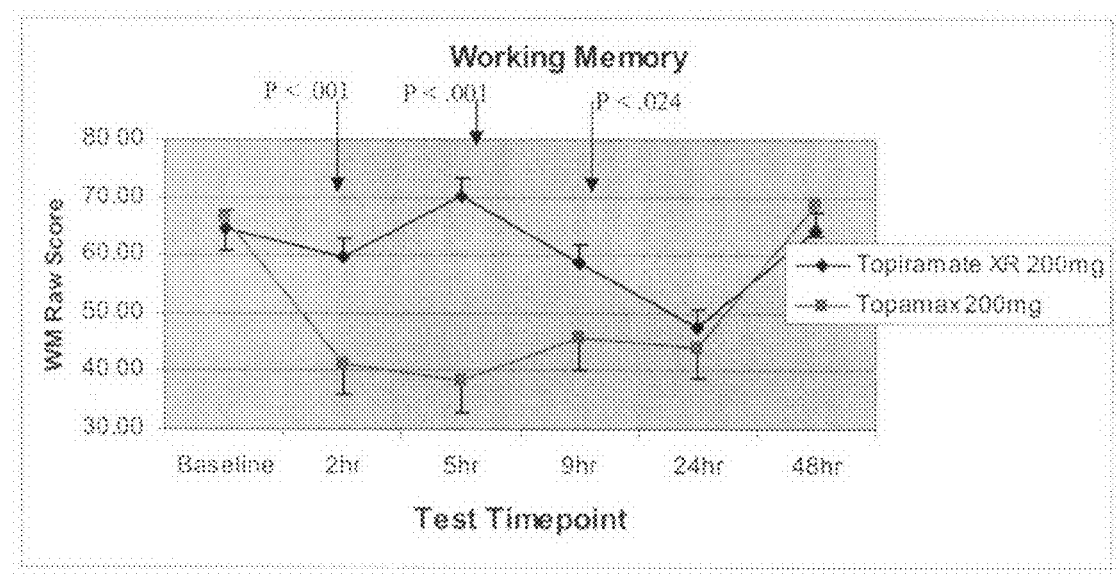
Fig. 26. Performance on the CNTB (working memory module) at various time intervals after administration of a single dose of 200mg (2x100mg) topiramate delayed XR capsule and Topamax tablets, 200mg (two capsules, each capsule containing 4 x 25mg tablets) in healthy human volunteers

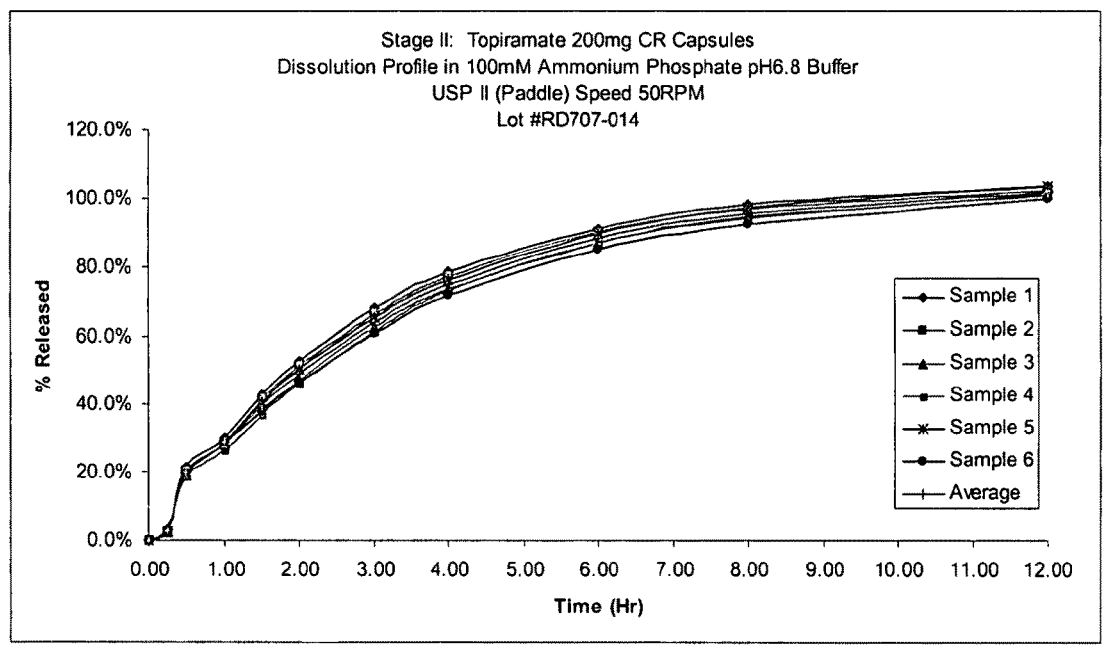
Fig. 27. Dissolution release profiles of topiramate XR capsules, 200mg (Example 21)

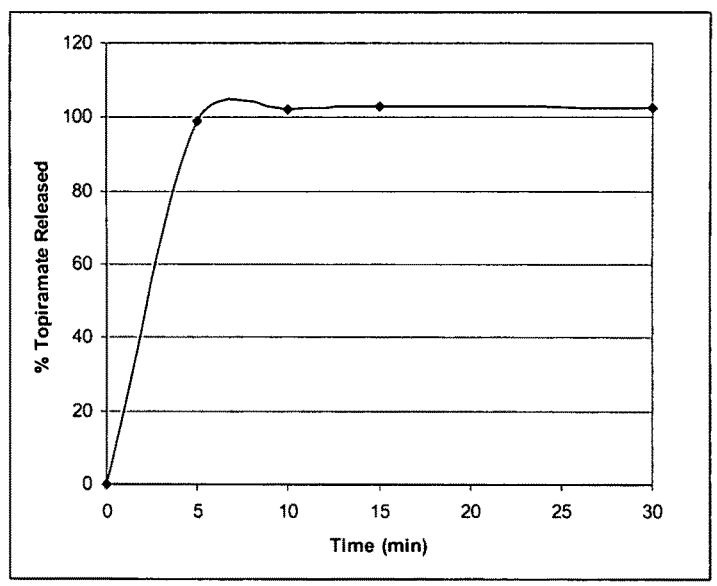
Fig. 28. Dissolution release profiles of topiramate delayed release sprinkle bead capsules (Example 22)

TOPIRAMATE COMPOSITIONS AND METHODS OF ENHANCING ITS BIOAVAILABILITY

RELATED APPLICATIONS

This application claims the benefit of priority of U.S. Provisional Application No. 60/841,924 filed Aug. 31, 2006. The entire teachings of the referenced Provisional Application are incorporated herein by reference in its entirety.

TECHNICAL FIELD OF THE INVENTION

The present invention relates to a dosage form and device for enhancing the bioavailability of topiramate. The present invention provides a composition with a topiramate-containing core and an enteric coating surrounding the core.

BACKGROUND OF THE INVENTION

Topiramate is an FDA approved anticonvulsant drug used as a monotherapy or an adjuvant therapy to treat a variety of forms of epilepsy (see Physician's Desk Reference, 56th ed., 2590-2595 (2002); disclosed in U.S. Pat. No. 4,513,006). Topiramate is used to prevent both partial onset and generalized seizures and is approved to treat simple partial seizures, complex partial seizures, and generalized tonic-clonic seizures in both children and adults. It is also indicated for treatment of Lennox-Gastaut syndrome (a disorder that causes seizures and developmental delays) in children.

There are three classifications of partial seizures: simple, complex, and secondarily generalized. A simple partial seizure usually manifests as jerking or shaking in one area of the body, which may progress to other areas. Simple partial seizures may also manifest with somatosensory, visual, auditory, olfactory, autonomic (sweating, pupillary dilation, epigastric rising), or psychiatric symptoms. In the case of complex partial seizures, the patient's consciousness may also be impaired. Patients experiencing a complex partial seizure will often exhibit a blank stare followed by automatism, which may include lip smacking, chewing, picking at clothing, or purposeless walking. Secondarily generalized seizures can evolve directly from simple partial or complex partial seizures, or progress from simple partial to complex partial to generalized (Leppik I E. Contemporary Diagnosis and Management of the Patient with Epilepsy. 4th Ed., Newtown, Pa.: Handbooks in Health Care Co (1999)).

Generalized seizures involve a loss of consciousness and may or may not be convulsive. Absence seizures (formerly called "petit mal") may be typical or atypical. The symptoms of typical absence seizures include a blank stare, eye blinking, and in some instances automatisms, and the patient may experience increased or decreased tone. These brief seizures tend to occur in groups and can occur 50 to 100 times in a day (Leppik I E. Contemporary Diagnosis and Management of the Patient with Epilepsy. 4th Ed., Newtown, Pa.: Handbooks in Health Care Co (1999)). Atypical absence seizures begin and end less abruptly than the typical absence seizures, but last longer and result in more pronounced changes in tone.

Myoclonic seizures manifest with quick, involuntary muscle jerks, which may be isolated to one part of the body or involve the entire body. Myoclonic seizures may accompany other generalized seizures and are common to specific epilepsy syndromes. Tonic seizures are generally associated with other epileptic syndromes and typically last less than a minute. Tonic seizures involve violent spasm or stiffening, and in many instances the lower extremities are extended and the upper extremities are flexed. In addition, the patient may turn the head or eyes to one side. Clonic seizures, most common in neonates and children, also exhibit repetitive muscular jerks but at a slower rate, and while clonic seizures can last as long as several minutes, brief episodes are more common (Leppik I E. Contemporary Diagnosis and Management of the Patient with Epilepsy. 4th Ed., Newtown, Pa.: Handbooks in Health Care Co (1999)).

Generalized tonic-clonic seizures (also called "grand mal") can occur at any age but are rare in very young infants (Morton et al., "Diagnosis and treatment of epilepsy in children and adolescents", *Drugs* 51: 399-414 (1996)). The seizures start with a sudden-onset tonic phase, typically lasting less than a minute, with all of the skeletal muscles contracting at once causing the patient to fall stiffly. In addition, the patient's diaphragm and chest muscles contract, forcing out air in a sigh or "epileptic cry." During the clonic phase, the patient may clench the jaws, biting the inside of the cheek or side of the tongue with the molars, and consciousness may not return for 10 to 15 minutes. The episode may result in feeling confusion, fatigue, and headache, which can last several hours to several days (Leppik I E. Contemporary Diagnosis and Management of the Patient with Epilepsy. 4th Ed., Newtown, Pa.: Handbooks in Health Care Co (1999)).

Atonic seizures result in a sudden loss of postural tone, causing the patient to fall. After a few seconds, the patient regains full consciousness. Atonic seizures are commonly associated with other seizure types and are common in Lennox-Gastaut syndrome (Leppik I E. Contemporary Diagnosis and Management of the Patient with Epilepsy. 4th Ed., Newtown, Pa.: Handbooks in Health Care Co (1999)).

Other epileptic conditions include juvenile myoclonic epilepsy and Lennox-Gastaut syndrome. Juvenile myoclonic epilepsy is a generalized, idiopathic epileptic syndrome, often exhibiting three seizure types: myoclonic, absence, and generalized tonic-clonic. Lennox-Gastaut syndrome may be symptomatic (brain lesion identified) or cryptogenic (brain lesion assumed), and the generalized syndrome may include atypical absence, tonic, atonic, and tonic-clonic seizures. Patients suffering from Lennox-Gastaut syndrome also have varying degrees of psychomotor retardation (Leppik I E. Contemporary Diagnosis and Management of the Patient with Epilepsy. 4th Ed., Newtown, Pa.: Handbooks in Health Care Co (1999); and Beaumanoir et al., "The Lennox-Gastaut syndrome", In: Roger et al., "Epileptic Syndromes in Infancy, Childhood, and Adolescence", 2.sup.nd Ed., London, England: John Libby, pp. 231-244 (1992)).

Memory impairment, mental slowing and attention deficits are the most frequently reported cognitive disorders in people with epilepsy and sometimes patients can find these cognitive consequences more debilitating than the actual seizures. Cognitive deficits in epilepsy are likely to be attributed to three key factors: the syndrome itself, the seizures, and the effect of the antiepileptic drug used for seizure control. The cognitive side effects of anti-epileptic drugs are particularly important in cognitively vulnerable populations such as children and elderly subjects. For example, side effects that manifest as minor cognitive impairments when observed in adults can cause extensive learning and cognition difficulties in children.

In addition to its use as an anticonvulsant, topiramate is most frequently prescribed for migraine prophylaxis [Brandes, et al., JAMA. 291 (8): 965-73 (2004); Silberstein et al., Arch Neurol. 61(4):490-5 (2004); Storey et al., Headache. 41(10):968-75 (2001); Mathew et al., Headache.

42(8):796-803 (2002); Diener et al., J. Neurol. 251(8):943-50 (2004); D'Amico et al Neurol Sci S130-S133 (2005); Storey J L et al. Neurology. (54) A267-A268 (2000); Edwards et al. Cephalalgia 20: S16 (2000]. Migraine is a severe form of recurrent headache typically accompanied by dizziness, nausea, vomiting or extreme sensitivity to light and sound. The classic migraine type may begin with aura, which consists of episodes of well-defined, transient focal neurological dysfunction that develops over the course of minutes and may last up to an hour.

Migraine treatment has progressed greatly over the last decade but unfortunately, prophylactic treatment of migraine has lagged behind acute care treatment. Beta-adrenergic blockers, calcium channel antagonists, antidepressant medications, and antiepileptic drugs (AEDs) have primary indications for other medical conditions but are commonly used for the prophylactic pharmacotherapy of migraine. For migraine prophylaxis preventive medications are typically selected by efficacy, adverse reactions, patient preference, co-occurrence of illness, and cost. The overall goals of prophylactic migraine therapy are to reduce the frequency and severity of migraine attacks, to make acute migraine attacks more responsive to abortive therapy and to improve the quality of life for patients. Many classes of drugs have been used but the prophylactic pharmacotherapy of migraine is less than satisfactory, because of poor efficacy, associated unacceptable side effects, tachyphylaxis and drug interactions.

Topiramate has been approved by FDA for migraine prophylaxis. Topiramate has numerous effects on the central nervous system, including neuronal excitability blockade and on excitatory amino acids, which are considered to be involved in the pathophysiology of migraine. Due to these effects, topiramate has been used for preventive management of chronic and intractable migraine.

Topiramate has been used by psychiatrists to treat bipolar disorder, although it is not FDA approved for this purpose. Because it is also one of only three AEDs that have a statistically proven propensity to induce weight loss, the drug has been investigated for use in treatment of obesity, especially to aid in the reduction of binge eating (McElroy, et al., *Am J. Psychiatry.* 160(2):255-61 (2003)). Topiramate is useful for neuropathic pain relief. In some groups of patients, diabetics for example, the potential of weight loss is desirable and may therefore be a major reason for using this medication for the treatment of diabetic neuropathic pain.

Other investigational uses of topiramate include treating alcoholism (Johnson, et al., *Lancet* 361(9370):1677-85 (2003)), cocaine and tobacco addiction (Sofuoglu, et al., *Psychopharmacology* 184(3-4): 645-51 (2006)), sleep disorders (Webber, *Am J Psychiatry* 159:872-873 (2002)), sleep-related eating disorders (Winkelman, *Sleep Med.* 4(3): 243-246 (2003)), Post traumatic stress disorder (Berlant, *J Clin Psychiatry* 62 Suppl 17:60-63 (2001)), depression (Carpenter, et al., *J Affect Disord.* 69(1-3):251-255 (2002)), and cluster headache (Lainez, *Headache.* 43(7):784-9 (2003)).

For the treatment of epilepsy, the recommended dosage of Topamax® is 400 mg/day typically taken in two divided doses (Physicians' Desk Reference, Thompson Healthcare, 56th Ed., pp. 2590-2595 (2002)). Lower doses than 400 mg/day (50-200 mg/day) are typically used for treating cluster headache and migraine prevention in non-epileptic subjects (U.S. Pat. No. 6,503,884, D'Amico., D et. al. Neurological Sciences 26, p 130, supplement 2, 2005, and Mosek, A et. al. Jr. of Headache and Pain 6, p 77, 2005).

Topiramate pharmacokinetics are linear, producing a dose-proportional increase in blood plasma concentration levels with increased dosing. Further, topiramate treatment has shown no evidence of patients developing drug tolerance with prolonged treatment over time. Following oral administration of an immediate release dosage form, topiramate is rapidly absorbed with peak plasma drug concentrations noted in approximately 2 hours. The mean elimination half life is about 21 hours. Topiramate pharmacokinetics are also not significantly affected by food.

The currently marketed immediate release topiramate formulation (Topamax®) is not ideal as it is associated with poor patient compliance as well as treatment-emergent side effects that lead to poor patient tolerance. The pharmacokinetics of the Topamax lead to high Cmax-related adverse effects including paresthesia, drowsiness, nausea, and vomiting, weight loss, ataxia, taste perversion and renal calculi. The most frequently reported adverse effects include behavioral and cognitive difficulties with an incidence of almost 50% in one retrospective review of 174 patients ((Kellet et al. *J. Neurol. Neurosurg and Psych.* 1999; 66:759-763). Similar results were also observed in various other studies (Thompson et al. *J. Neurol. Neurosurg and Psych.* 2000; 69:634-641 and Meador et al. *Neurology* 2005; 64: 2108-2114). Decline in verbal frequency, attention, processing speed and working memory were seen for Topamax in another adjunctive study of patients with epilepsy (Lee et al. *Epilepsia* 2003; 44: 339-347). The negative cognition effects of Topamax are especially important to those who require maximal cognitive efficiency in their jobs and daily activities.

The time it takes for topiramate to reach peak plasma levels (i.e., about two hours) also limits its effective use in the treatment of some conditions, such as neuropathic pain. Therefore, improved dosage forms of topiramate are needed in order to increase the safety, effectiveness, and utility of the compound.

SUMMARY OF THE INVENTION

The present invention is directed in part to topiramate pharmaceutical compositions that allow for controlled administration, preferably once-daily or even alternate day administration that releases topiramate over an extended period of time. The dosage form is preferably at least equivalent in effectiveness to the conventional immediate release, multiple-dose daily regimen, and provides average steady-state blood levels of topiramate over a course of treatment. A once-a-day administration of topiramate is advantageous over multiple-dose administration in terms of patient compliance and reduced adverse events, thus providing better treatment of the conditions for which the topiramate is indicated.

In one aspect, the invention provides an oral immediate release (IR) and/or extended release (XR) dosage form that provides continuous and stable delivery of topiramate over an extended duration and maintains the desired therapeutic effects while minimizing, if not eliminating, the undesired side effects and with improved patient compliance.

Preferably, topiramate and/or its prodrug(s) and/or stereoisomers are released at a rate that results in reduction in the frequency or severity of at least one adverse effect associated with topiramate therapy. In certain embodiments, the dosage form releases topiramate and/or its prodrug and/or stereoisomers at a rate that results in reduction in the frequency or severity of at least one adverse event associated with current topiramate therapies, or allows for a more convenient dosing regimen than current therapies.

Thus, one aspect of the invention provides a delayed-release (DR) topiramate pharmaceutical composition in an orally deliverable form, comprising an enteric coating, a topiramate core, and one or more pharmaceutically acceptable carriers and excipients.

In certain embodiments, topiramate administered using a dosage form of the invention is substantially released and/or absorbed in the lower GI tract, such as in the intestine (e.g., the small intestine, the colon, and/or the rectum).

In certain embodiments, the enteric coating delays the release of topiramate by at least about 1.5-2 hours, or 2-3 hours after ingestion.

In certain embodiments, the enteric coating is selected from: cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, co-polymerized methacrylic acid/methacrylic acid methyl esters selected from: EUDRAGIT® L12.5, L100, EUDRAGIT® S12.5, S100, EUDRAGIT® L30D55, EUDRAGIT® FS30D, EUDRAGIT® L100-55, EUDRAGIT® S100 (Rohm Pharma), KOLLICOAT® MAE30D and 30DP (BASF), ESTACRYL® 30D (Eastman Chemical), AQUATERIC® and AQUACOAT® CPD30 (FMC)), Acryl-EZE™, SPHEROMER III®, SPHEROMER IV® (Spherics Inc), or equivalents thereof.

In certain embodiments, the enteric coating becomes soluble at above pH 4.5, such as around pH 5.5-6.8

In certain embodiments, the topiramate pharmaceutical composition comprises a topiramate salt, or derivatives or stereoisomers or prodrugs thereof.

In certain embodiments, the topiramate is micronized to improve bioavailability.

In certain embodiments, the topiramate is converted to the stable amorphous form to improve bioavailability.

In certain embodiments, the topiramate formulation contains basifying agents and/or surfactants, e.g., to stabilize topiramate.

In certain embodiments, the topiramate formulation comprises topiramate, a surfactant, a basifying agent, and an enteric polymer. In certain embodiments, the topiramate formulation further comprises at least one release rate controlling polymer. In some embodiments, the topiramate formulation contains at least two release rate controlling polymers, wherein varying the ratios of the polymers varies the rate of release of the topiramate from the formulation, e.g., to adjust the release profile as desired. In certain embodiments, the topiramate formulation further comprises a glidant. In some embodiments, the topiramate formulation comprises particles encapsulated in a gelatin capsule and optionally coated with an enteric polymer. In particular embodiments, the capsules are produced without banding.

In certain embodiments, the pharmaceutical composition comprises a core formulated as a topiramate immediate release (IR) composition.

In certain embodiments, the pharmaceutical composition comprises a core formulated as a topiramate delayed release (DR) composition. In certain embodiments, the pharmaceutical composition comprises a core formulated as a topiramate extended release (XR) composition.

In certain embodiments, the pharmaceutical composition comprises an immediate release core encapsulated within an enteric polymer. In certain embodiments, the topiramate dosage form is a gelatin capsule comprising the core or cores, wherein the capsule is coated by an enteric polymer. In some embodiments, the capsules may be broken and the contents mixed with food for oral administration.

In certain embodiments, the XR composition is prepared by coating topiramate-coated inert pellets with a release-controlling polymer.

In certain embodiments, the release-controlling polymer comprises ethylcellulose.

In certain embodiments, the release-controlling polymer is selected from: EUDRAGIT® RL100; EUDRAGIT® RS 100; cellulose derivatives selected from: ethylcellulose aqueous dispersions (AQUACOAT®, SURELEASE®), hydroxyethyl cellulose, hydroxypropyl cellulose, or hydroxypropyl methylcellulose; polyvinylpyrrolidone; polyvinylpyrrolidone/vinyl acetate copolymer; KOLLICOAT® SR30D, cellulose acetate, cellulose acetate butyrate, or combinations thereof.

In another embodiment, the relative amounts of crystalline and amorphous forms of topiramate may be varied to alter the target release profile. The crystalline and amorphous forms can also be distributed in the immediate and controlled release populations in the ratio of 1:20 to 1:0.5 or 20:1 to 0.5:1, more preferably from 1:5 to 1:1.

In certain embodiments, the topiramate pharmaceutical composition is formulated to provide an effective dose over at least 4-24 hours after administration to the patient.

In certain embodiments, the topiramate pharmaceutical composition is formulated to provide an effective plasma level over at least 8-48 hours after administration to the patient.

In certain embodiments, the topiramate has a Tmax at least 12 hours, 20 hours, or even 24 hours after administration.

In certain embodiments, the pharmaceutical composition comprises an XR portion and an IR portion.

In certain embodiments, the XR portion and the IR portion are both present as multiparticulate beads or pellets embedded within a dissolvable/disintegratable matrix, e.g., an inactive dissolvable/disintegrable matrix.

In certain embodiments, the XR portion and the IR portion are each present as a section of the pharmaceutical composition. In certain embodiments, the XR portion is formulated as a plurality of particles and the IR portion is formulated as a layer disposed about the particles. In certain embodiments, the layered particles are encapsulated in a gelatin capsule and optionally coated with an enteric polymer. In particular embodiments, the capsules are produced without banding.

In certain embodiments, the XR portion is partially or completely covered by a rate-controlling coating that controls the release rate of the XR portion.

In certain embodiments, the pharmaceutical composition comprises both XR and IR pellets disposed in an enteric-coated gelatin capsule/tablet.

In certain embodiments, the topiramate pharmaceutical composition is formulated as a once-a-day composition or alternate day composition.

In certain embodiments, the once-a-day composition comprises about 15 mg, 25 mg, 50 mg, 100 mg, 200 mg or 400 mg of topiramate.

In certain embodiments, the topiramate pharmaceutical composition provides an effective plasma level between 1-10 µg/mL at steady state for epilepsy treatment.

In certain embodiments, the topiramate pharmaceutical composition provides an effective plasma level between 2-8 µg/mL at steady state for migraine treatment.

In certain embodiments, the topiramate pharmaceutical composition further comprises a bioadhesive layer, e.g., that adheres to the lower GI tract.

In certain embodiments, the bioadhesive layer comprises one or more polymeric materials selected from polyamides, polyalkylene glycols, polyalkylene oxides, polyvinyl alcohols, polyvinylpyrrolidone, polyglycolides, polyurethanes, polymers of acrylic and methacrylic esters, polylactides, poly(butyric acid), polyanhydrides, polyorthoesters, poly(fumaric acid), poly(maleic acid), polycarbonates, polyalkylenes, polyalkylene terephthalates, polyvinyl alcohols, polyvinyl ethers, polyvinyl esters, polyvinyl halides, polysiloxanes, polystyrene, poly(lactide-co-glycolide), chitosan, chitin, hyaluronic acid, hyalurronan, Carbopols, Corplex polymers, Polycarbophils-Cysteine (Thiomers), Chitosan-Thioglycolic acid copolymers (Thiomers), poly(methacrylic acid-grafted-ethylene glycol), poly(methyl vinyl ether-co-malic anhydride), cholestyramine (Duolite AP-143), sucralfate and gliadin, blends and copolymers thereof.

In certain embodiments, the topiramate pharmaceutical composition, upon administration to an individual, eliminates or reduces at least one undesirable side-effect selected from: paresthesia, drowsiness, nausea, dizziness, vomiting, weight loss, ataxia, taste perversion and renal calculi as compared to treatment with the immediate release composition of the same overall dosage.

In certain embodiments, the present invention provides methods of treating epilepsy, migraine, obesity, obsessive compulsive disorder, addiction, or bipolar disorder in an individual.

In certain embodiments, the present invention provides methods of migraine prophylaxis.

In certain embodiments, the topiramate formulation comprises at least one active agent.

In other embodiments, the topiramate formulation does not comprise additional active agents but is administered conjointly with said active agents.

In certain embodiments, the topiramate pharmaceutical composition is administered at a time such that the Tmax of the topiramate composition occurs during a patient's sleeping hours, which may improve sleep quality in the patient and/or reduce daytime side effects of the topiramate therapy relative to a patient receiving the topiramate composition at a time that results in a Tmax occurring during waking hours. In certain embodiments, the Tmax occurs at least 2, 10, 15, 20, or 24 hours after administration.

In certain embodiments, the topiramate pharmaceutical composition is administered at a time such that the plasma concentration of topiramate decreases while the patient is sleeping. In certain embodiments, the plasma concentration of topiramate decreases for at least 1, 2, 4, 6, or 8 hours while the patient is sleeping. In certain embodiments, the plasma concentration of topiramate decreases by at least 10, 25, 50, or 75 percent while the patient is sleeping.

In certain embodiments, the extended release pharmaceutical composition provides substantially reduced degree of fluctuation in plasma levels compared to immediate release pharmaceutical composition of the topiramate of the same dose administered multiple times daily.

In certain embodiments, the Cmax of the topiramate pharmaceutical composition in the first 2 hours after administration to a human is at least 25, 50, or 75 percent less than the Cmax of an IR topiramate composition in the first 2 hours after administration to a human. In certain embodiments, the Cmax of the composition in the first 5 hours after administration to a human is at least 25, 50, or 75 percent less than the Cmax of an IR topiramate composition in the first 5 hours after administration to a human. In certain embodiments, the Cmax of the composition in the first 10 hours after administration to a human is at least 25, 50, or 75 percent less than the Cmax of an IR topiramate composition in the first 10 hours after administration to a human.

In certain embodiments, administration of the topiramate pharmaceutical composition produces less cognitive impairment than administration of an IR topiramate composition. In certain embodiments, administration of the topiramate pharmaceutical composition produces less cognitive impairment as measured by the Computerized Neurophysiological Test Battery (CNTB) than administration of an IR topiramate composition. In certain embodiments, administration of the topiramate pharmaceutical composition produces less cognitive impairment as measured by the Controlled Oral Word Association Test (COWAT) than administration of an IR topiramate composition. In certain embodiments, administration of the topiramate pharmaceutical composition produces less cognitive impairment as measured by the Symbol Digital Modalities Test (SDMT) than administration of an IR topiramate composition. Preferably, the impairment by any one or more of these measures is at least 10% less, 25% less, 50% less or even at least 75% or 90% less than the impairment resulting from an IR topiramate formulation.

In certain embodiments, administration of the topiramate pharmaceutical composition produces fewer side-effects than administration of an IR topiramate composition.

In certain embodiments, the topiramate pharmaceutical composition is suitable for human treatment, or for veterinary treatment of a non-human mammal.

Another aspect of the invention provides a method of preparing a topiramate pharmaceutical composition, comprising coating a topiramate formulation with an enteric coating that reduces or substantially eliminates the release and/or absorption of topiramate in the upper gastrointestinal (GI) tract, such as in the stomach. The invention also provides a method of preparing a topiramate pharmaceutical composition, comprising a capsule wherein the capsule is sealed without banding and optionally coated with an enteric polymer.

Embodiments described herein are contemplated to be combined with each other embodiments as appropriate. Embodiments described in detail under one aspect of the invention may be equally applicable for the other aspects of the invention.

BRIEF DESCRIPTION OF THE DRAWINGS

FIG. 2A shows the degradation of Topamax® tablets (100 mg) in 0.1 N HCl at 37° C.

FIG. 2B shows the degradation of topiramate drug substance in 0.1 N HCl at 37° C.

FIG. 2C shows the dissolution profiles of Topamax® tablets (100 mg) in phosphate buffer, pH 6.8 at 37° C.

FIG. 3 shows the plasma concentration time profiles of Topamax® tablets (100 mg) in fed and fasted beagles.

FIG. 4 shows the pharmacokinetic profiles of Topamax® tablets (100 mg) and enteric-coated, delayed-release Topamax® Tablets (100 mg) in fed beagles.

FIG. 5A shows the dissolution profiles of Topamax® tablets (100 mg) and enteric-coated, delayed-release Topamax® tablets (100 mg).

FIG. 5B shows the pharmacokinetic profiles of Topamax® tablets (100 mg) and enteric-coated, delayed-release Topamax® tablets (100 mg) in fasted beagles.

FIG. 6 shows the pharmacokinetic profiles of Topamax® tablets (100 mg) and topiramate bioadhesive trilayer XR tablets (100 mg) from Example 5, in fed beagles.

FIG. 7 shows the pharmacokinetic profiles of Topamax® tablets (100 mg) and topiramate bioadhesive trilayer XR tablets (100 mg) from Example 6, in fed beagles.

FIG. 8 shows the pharmacokinetic profiles of Topamax® tablets (100 mg) and topiramate bioadhesive trilayer XR tablets (100 mg) from Example 7, in fed beagles.

FIG. 9 shows the dissolution profiles of Topamax® tablets (100 mg) and topiramate bioadhesive delayed and extended-release multiparticulates formulations (100 mg) (Examples 8-11).

FIG. 12A shows the particle size analysis of micronized topiramate.

FIG. 12B shows the topiramate plasma profiles of Topamax®, 100 mg and micronized topiramate immediate release tablets, 100 mg in fasted beagles.

FIG. 13A shows the DSC scans of crystalline topiramate.

FIG. 13B shows the DSC scans of spray-dried amorphous topiramate.

FIG. 14 shows the dissolution profiles of topiramate rapidly disintegrating XR pelletized tablet, 100 mg, in 0.1 N HCl (0-2 hrs) followed by ammonium phosphate buffer (2-8 hrs), pH 6.8 at 37° C.

FIG. 15 shows a schematic design of a topiramate delayed release rapidly disintegrating XR pelletized tablet.

FIG. 16 shows a schematic design of a topiramate rapidly disintegrating extended release (XR) pelletized tablet 100 mg with split function.

FIG. 17A shows a predicted steady state topiramate plasma levels in healthy volunteers from day 1 to day 7 of dosing of 100 mg bioadhesive delayed release topiramate XR multiparticulate formulations Type A and Type B and an equivalent dose of Topamax® tablets.

FIG. 17B shows a predicted steady state topiramate plasma levels in healthy volunteers following the last dose (day 7) of 100 mg bioadhesive delayed release topiramate XR multiparticulate formulations Type A and Type B and an equivalent dose of Topamax® tablets.

FIG. 18 shows topiramate plasma concentration time profiles after administration of a single dose of 100 mg topiramate bioadhesive delayed XR capsule, 100 mg topiramate non-bioadhesive delayed XR capsule and Topamax tablets, 100 mg in healthy human volunteers.

FIG. 19 shows performance on the COWAT test at various time intervals after administration of a single dose of 100 mg topiramate bioadhesive delayed XR capsule, 100 mg 100 mg topiramate non-bioadhesive delayed XR capsule and Topamax tablets, 100 mg in healthy human volunteers.

FIG. 20 shows performance on the SDMT test at various time intervals after administration of a single dose of 100 mg topiramate bioadhesive delayed XR capsule, 100 mg 100 mg topiramate non-bioadhesive delayed XR capsule and Topamax tablets, 100 mg in healthy human volunteers FIG. 21 shows performance on the CNTB (working memory module) at various time intervals after administration of a single dose of 100 mg topiramate bioadhesive delayed XR capsule, 100 mg topiramate non-bioadhesive delayed XR capsule and Topamax tablets, 100 mg in healthy human volunteers.

FIG. 22 shows topiramate plasma concentration time profiles after administration of a single dose of 200 mg (2×100 mg) topiramate delayed XR capsule and Topamax tablets, 200 mg (two capsules, each capsule containing 4×25 mg tablets) in healthy human volunteers.

FIG. 23 shows performance on the COWAT test at various time intervals after administration of a single dose of 200 mg (2×100 mg) topiramate delayed XR capsule and Topamax tablets, 200 mg (two capsules, each capsule containing 4×25 mg tablets) in healthy human volunteers.

FIG. 24 shows performance on the SDMT test at various time intervals after administration of a single dose of 200 mg (2×100 mg) topiramate delayed XR capsule and Topaniax tablets, 200 mg (two capsules, each capsule containing 4×25 mg tablets) in healthy human volunteers.

FIG. 25 shows performance on the CNTB (visual memory module) at various time intervals after administration of a single dose of 200 mg (2×100 mg) topiramate delayed XR capsule and Topamax tablets, 200 mg (two capsules, each capsule containing 4×25 mg tablets) in healthy human volunteers.

FIG. 26 shows performance on the CNTB (working memory module) at various time intervals after administration of a single dose of 200 mg (2×100 mg) topiramate delayed XR capsule and Topamax tablets, 200 mg (two capsules, each capsule containing 4×25 mg tablets) in healthy human volunteers.

FIG. 27 shows dissolution release profiles of topiramate XR capsules, 200 mg (Example 21).

FIG. 28 shows dissolution release profiles of topiramate delayed release sprinkle bead capsules (Example 22).

DETAILED DESCRIPTION OF THE INVENTION

I. Overview

Figure 1A:
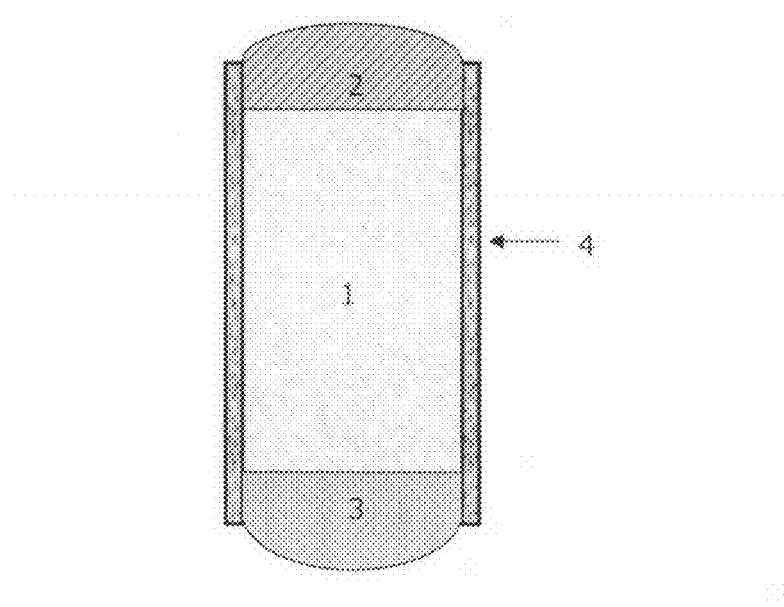
FIGS. 1A-1Q are schematic drawings (not to scale) illustrating cross-sectional views of exemplary designs for the subject delivery device.

In general, the present invention relates to pharmaceutical compositions and methods for the prophylaxis or treatment of disorders for which topiramate is administered. Such disorders include seizure disorders and headache, such as migraine. Other such disorders may also include, but are not limited to, obesity; alcohol, cocaine, and/or tobacco dependence; bipolar disorder; and other central nervous system disorders. The pharmaceutical compositions and methods of the invention relate to the use of topiramate either alone or in combination with other active agents or pharmaceutical compositions suitable for the treatment of such diseases.

In certain embodiments, the topiramate formulation comprises additional active agents. The topiramate formulation may comprise one or more anti-convulsants, calcium channel blockers, beta-blockers, anti-depressants, anti-inflammatories, or other drugs. Suitable active agents for the treatment of epilepsy include budipine (see, e.g., Fisher et al., *Epilepsia* 45(11):1300-7 (2004)), diazepam (see, e.g., Francoise et al., *Epilepsy Research* 72:147-63 (2006), lamotrigine (see, e.g., Luszczki et al., *Epilepsia* 44(8):1003-13 (2003), phenyloin, phenobarbital, carbamazepine, oxcarbazepine, valproate, ethosuximide, clonazepam, lamotrigine, vigabatrin, tiagabine, gabapentin, and felbamate (reviewed in Deckers et al., *Epilepsia* 41(11):1364-74 (2000). Suitable active agents for the treatment of migrane include beta-blockers (see, e.g., Pascual et al., *Acta Neurol. Scand* 115 (2):81-3 (2007)) and almotriptan malate. Suitable active agents for the treatment of Parkinsonism include declorazepam (see, e.g., Siniscalchi et al., *Parkinsonism Relat Disord* 13(2): 129-30 (2007)). Suitable active agents for the treatment of obesity include metformin (see, e.g., Toplak et al., *Int J Obes* 31(1)138-46 (2007), leptin (see, e.g., Lalonde et al., *Physiol Behav* 80(4):415-20 (2004), ephedrine, fluoextine, bupropion, zonisamide, phentermine, amphetamines, amfepramone, phenylpropanolamine, mazindol, fenfluramines, sibutramine, and orlistat (reviewed in Ioannides-Demos et al., *Drugs* 65(10): 1391-418 (2005). Suitable active agents for the treatment of obsessive compulsive disorder include paroxetine (see, e.g., Hollander et al., *Int Clin Psychopharmacol* 21(3): 189-91 (2006). Suitable active agents for the treatment of bipolar disorder include clozapine (see, e.g., Chen et al., *Clin Neuropharmacol* 28(3):136-8 (2005), risperidone (see, e.g., Bahk et al., *Prog Neuropsychopharmacol Biol Psychiatry* 29(1):115-21 (2005), lithium (see, e.g., Pies, *Ann Clin Psychiatry* 14(4):223-32 (2002), and bupropion (see, e.g., Erfurth et al., *Neuropsychobiology* 45 Suppl 1:33-6 (2002). Topiramate formulations described herein may include one or more of the above compounds.

In other embodiments, the topiramate formulation does not comprise additional active agents but is administered conjointly with said active agents. The present invention also provides methods of administering the topiramate formulations of the present invention conjointly with other active agents.

In some embodiments, the combination therapies of the invention may have additive or synergestic effects. In other embodiments, the combinations are selected to reduce side-effects of a therapeutic regime (e.g., weight gain).

In certain embodiments, the present invention provides a kit comprising a first pharmaceutical formulation comprising a topiramate formulation as described herein; a second pharmaceutical formulation comprising at least one pharmaceutically active agent; and instructions for the administration of the first and second pharmaceutical formulations.

In certain embodiments, the present invention provides a kit comprising a topiramate formulation as described herein and instructions for the administration of the topiramate formulation conjointly with another compound as discussed above.

In certain embodiments, the invention relates to particular topiramate dosage forms (e.g., a delayed release, preferably once-a-day dosage form or alternate day dosage form) that provide release profiles that are effective for the intended therapeutic use (e.g., ameliorating or overcoming symptoms of epilepsy or migraine or migraine prophylaxis), while reducing or avoiding at least one undesirable side-effect associated with conventional topiramate treatment. In some embodiments, the undesirable side-effects are reduced by administering a dosage form with an ascending release rate. In particular embodiments, cognitive-impairments associated with Topamax therapy are reduced.

Applicants have observed that topiramate is unstable under acidic conditions and degrades. Due to its acid-sensitive nature, topiramate may benefit from protection from the relative acidic environment of the upper GI tract, which would otherwise lead to degradation of the drug. Thus, according to one aspect of the invention, the release of topiramate is delayed until the drug is in the lower GI tract, such as in the intestine (e.g., the small intestine, the colon, and/or the rectum), or only a portion of the topiramate in the formulation is released in the stomach for immediate pharmacological action while the remaining topiramate is released in the proximal and/or distal gastro-intestinal tract. One way to reduce or eliminate the release of topiramate in the stomach is to utilize an enteric coating, such that topiramate is not substantially released in the acidic environment of the stomach. In certain embodiments, the enteric coating delays the release of topiramate by at least about 0.1-8 hours after administration based on the fasted state of the subject. In certain embodiments, the enteric coating delays the release of topiramate by at least about 0.1-16 hours after administration based on the fed state of the subject.

Once inside the intestine, where the local pH environment is higher, topiramate is released immediately, e.g., from an immediate release (IR) dosage portion, or gradually from an extended release (XR) dosage portion, or a combination thereof. Since such dosage forms are also delayed-release dosage forms, they are referred to as delayed immediate release (DIR or DR) or delayed extended release (DXR) dosage forms, respectively.

In a preferred embodiment, the DXR dosage form achieves the therapeutic benefit of a conventional multiple-dose topiramate regimen and yet is administered as a single daily administration, e.g., yet releases the drug in a controlled manner and over an extended period of time, thus improving patient compliance, and alleviating and/or eliminating the undesirable daily "peak and trough" blood levels produced by multiple daily doses. The amount of drug contained in the single dose formulation may be equivalent to the amount of drug administered in the multiple dosing regimen. The amount of drug contained in the single dose formulation may also be less than the amount of drug administered in the multiple dose regimen because the controlled-release formulation eliminates the high peaks caused by the multiple daily doses and provides drug concentrations at therapeutic levels for increased periods of time.

In certain embodiments, the dosage form may include a bioadhesive composition that adheres to the lower GI tract, such as intestinal walls, to prolong the release of topiramate in the lower GI tract. The bioadhesive layer may be inside or outside the enteric coating. In the former case, the presence of the bioadhesive layer (e.g., as a partial coating that is continuous or discontinuous) preferably does not substantially impede the release of topiramate. In the latter case, the presence of the bioadhesive layer (e.g., as a partial coating that is continuous or discontinuous) does not substantially impede the degradation of the enteric layer in the neutral pH environment of the intestine and/or delay passage of the dosage form from the stomach into the intestine.

In vivo profiles for topiramate that provide the appropriate blood (or, more particularly, plasma) concentration levels over time in order to meet the therapeutic requirements for once daily or even alternate day administration are provided in the present invention. These profiles are such that the mean blood topiramate levels provide an effective amount of the drug for the treatment of such conditions epilepsy or migraine, yet below levels that induce adverse side effects typically associated with spikes in the plasma concentration that follow the multiple administration of presently available immediate-release formulations.

Thus, the present dosage forms can achieve an effective blood topiramate concentration at relatively steady state. These dosage forms may be delayed release, immediate release, extended release, or a combination thereof.

In some embodiments, the Cmax of the dosage formulation is less than the Cmax of Topamax® when the same dosage is administered to a patient or beagle dog. In certain embodiments, the Cmax of the dosage form is at least 10% less than the Cmax of Topamax® when the same dosage is administered to a patient or beagle dog. In certain embodiments, the Cmax of the dosage form is at least 20% less than the Cmax of Topamax® when the same dosage is administered to a patient or beagle dog.

In some embodiments, the Cmax of the dosage formulation occurs about 1 to about 30 hours after administration to a patient or beagle dog. In some embodiments, the Cmax occurs about 10 to about 20 hours after administration to a patient or beagle dog.

In some embodiments, the Tmax of the dosage formulation is later than the Tmax of Topamax® when the same dosage is administered to a patient or beagle dog. In some embodiments, the Tmax of the dosage form is about 1 to about 25 hours later than the Tmax of Topamax® when the same dosage is administered to a patient or beagle dog. In some embodiments, the Tmax of the dosage form occurs about 1 to about 30 hours after administration to a patient or beagle dog. In some embodiments, the Tmax occurs about 10 to about 20 hours after administration to a patient or beagle dog. In certain other embodiments, the Tmax of the dosage formulation is earlier than the Tmax of Topamax® when the same dosage is administered to a patient or beagle dog. Such dosage forms may be useful for episodic treatment rather than prophylactic treatment and may be in micronized form.

In some embodiments, the AUC of the dosage formulation is greater than the AUC of Topamax® when the same dosage is administered to a patient or beagle dog. The AUC of the dosage form is preferably at least 10% greater than the AUC of Topamax® when the same dosage is administered to a patient or beagle dog. The AUC of the dosage form is most preferably at least 20%, or even 25% more than the AUC of Topamax® when the same dosage is administered to a patient or beagle dog.

In certain embodiments, the AUC of the dosage formulation in the plasma of a fed beagle dog is at least about 5, about 10, about 20, or even about 25% greater than the AUC of an immediate-release formulation of an identical dose of topiramate when measured for 36 hours after administration of a single dose of said composition to the fed beagle.

One aspect of the invention relates to a topiramate pharmaceutical composition, comprising three regions: a) first and second regions, each comprising a controlled or extended release (CR/XR) topiramate component and an immediate release (IR) topiramate component; and b) a third region substantially free of topiramate and comprising a pharmaceutical excipient; wherein the third region separates the first region from the second region. In certain such embodiments, the first and second regions each have equal quantities of topiramate controlled or extended release component and equal quantities of topiramate immediate release component. In certain embodiments, the topiramate pharmaceutical composition may be shaped as shown in FIG. 16.

In certain embodiments, the third region comprises a visual indicator at a location within the third region. In certain such embodiments, the third region is configured to be cleaved at a location between the first and second regions to form two portions, one portion comprising the first region and a fragment of the third region, and the other portion comprising the second region and a fragment of the third region. In certain such embodiments, the third region is scored to facilitate cleavage into two portions.

In certain embodiments, the third region is configured to be cleaved at location that is selected such that upon cleavage, a first face and a second face are exposed, wherein the first and second face intersect neither the first region nor the second region. Such a face may be substantially flat or may be textured or jagged.

In certain embodiments, each of the first and second regions comprises a dose of topiramate. In certain alternative embodiments, the first and second regions together comprise a dose of topiramate. In certain embodiments, entire pharmaceutical composition comprises a dose of topiramate.

In certain embodiments, the controlled or extended release component comprises a plurality of pellets, comprising topiramate and a release rate-controlling polymer. In certain such embodiments, at least a portion of the controlled or extended release pellets further comprise a bioadhesive polymer. In certain such embodiments, at least a portion of the controlled or extended release pellets are individually coated with the bioadhesive polymer. In certain such embodiments, at least a portion of the pellets are individually coated with an enteric coating.

In certain embodiments, at least a portion of the pellets are individually coated with both the bioadhesive polymer and the enteric coating.

In certain embodiments, a first portion of the controlled or extended release pellets are coated with an enteric coating and a bioadhesive polymer and a second portion of the controlled or extended release pellets are coated with a release rate-controlling polymer and a bioadhesive polymer.

In certain embodiments, the pellets are disposed in a matrix.

In certain embodiments, the immediate release component is in the form of granules.

In certain embodiments, the first, second, and third regions are all covered with an enteric coating and a bioadhesive coating.

Another aspect of the invention provides a method for making the pharmaceutical compositions with one or more features as described above.

Another aspect of the invention provides a method for using the pharmaceutical compositions with one or more features as described above in treating a disorder such as epilepsy and migraine or prophylaxis of migraine.

Another aspect of the invention provides the use of a pharmaceutical composition with one or more features as described above in manufacturing medicaments for the treatment of a disorder such as epilepsy and migraine or prophylaxis of migraine.

The subject preparations and methods can be used as part of treatments for human and/or other animal subjects. In addition to humans, other animal subjects to which the invention is applicable include domestic animals and livestock, raised either as laboratory animals, pets or zoo animals, or for commercial purposes. Examples are rodents such as mice, rats, hamsters, or rabbits; dogs; cats; cattle; horses; sheep; hogs; and goats.

Certain general features of the invention are further elaborated in the sections below.

II. Exemplary Uses of the Dosage Forms

In various embodiments, the present invention contemplates modes of treatment and/or prophylaxis (e.g., treating or preventing the development of symptoms in high-risk populations), which utilize one or more of the subject dosage forms for decreasing or overcoming the incidence of seizures in a patient.

In various embodiments, the present invention also contemplates modes of treatment and/or prophylaxis, which utilize one or more of the subject dosage forms for decreasing or overcoming the symptoms of a migraine patient. Formulations containing an IR component may be beneficial for acute treatment while extended-release formulations are appropriate for prophylactic treatment.

The present invention provides topiramate compositions which release the drug at a constant slow rate without evidence of dose dumping and maintain effective plasma topiramate concentration profile over a 24-hour duration. These formulations may can be optimally dosed to treat other conditions that are ameliorated by topiramate including, but not limited to, eating disorders, obesity, high blood pressure, bipolar disease, post traumatic stress disorder, cluster headaches, and neuropathic pain.

The various embodiments of the present invention can be used in chronic dosing. In certain embodiments, the pharmaceutical can be used for once-daily administration or alternate day administration. In some embodiments, the dosage form is a pharmaceutical taken at night before sleeping to reduce side effects associated with peak plasma concentrations.

III. Definitions

For convenience, certain terms employed in the specification, examples, and appended claims are collected here. All other terms have their ordinary meanings as understood by a skilled artisan.

As used herein, "about" means within the pharmaceutically acceptable limits found in the United States Pharmacopeia (USP-NF 21), 2003 Annual Edition, or available at the USP website, for amount of active pharmaceutical ingredients. With respect to blood levels, "about" means within FDA acceptable guidelines.

The term "water-soluble" herein means having solubility in water of at least about 10 mg/mL. Unless otherwise specified, "solubility" herein means solubility in water at 20-25° C. at any physiologically acceptable pH, for example at any pH in the range of about 1.2 to about 8. In the case of a salt, reference herein to solubility in water pertains to the salt, not to the free base form of topiramate.

The term "orally deliverable" herein means suitable for oral, including peroral and intra-oral (e.g., sublingual or buccal) administration, but tablets of the present invention are adapted primarily for peroral administration, i.e., for swallowing, typically whole (or, in certain embodiments, broken), with the aid of water or other drinkable fluid.

A "subject" herein is an animal of any species, preferably mammalian, most preferably human. Conditions and disorders in a subject for which a particular agent is said herein to be "indicated" are not restricted to conditions and disorders for which the agent has been expressly approved by a regulatory authority, but also include other conditions and disorders known or believed by a physician to be amenable to treatment with the agent.

"Treatment" herein embraces prophylactic treatment unless the context requires otherwise.

The term "$ED_{50}$" means the dose of a drug which produces 50% of its maximum response or effect.

An "effective amount" of, e.g., a movement disorder pharmaceutical composition, with respect to the subject method of treatment, refers to an amount of the pharmaceutical composition in a preparation which, when applied as part of the subject dosage regimen brings about the desired correction according to clinically acceptable standards.

The term "$LD_{50}$" means the dose of a drug which is lethal in 50% of test subjects.

The term "lethal therapeutic index" refers to the therapeutic index of a drug defined as $LD_{50}/ED_{50}$.

The term "metabolites" refers to active derivatives produced upon introduction of a compound into a biological milieu, such as a patient.

The term "particle" refers to particles that comprise topiramate or a pharmaceutically acceptable salt thereof in any suitable size and shape. Typically, particles have a diameter in the range of about 1 micron to about 0.3 mm. Examples of different particle shapes include rods, granules, planar structures and other regular or irregular shapes.

The terms "bead," "beadlet," multiparticulate, and "pellet" are used interchangably herein to refer to a formulation that comprises topiramante or a pharmaceutically acceptable salt thereof and has a diameter of about 0.1 to 2 mm or even from 0.3 to 1.5 mm.

The term "minitablet" as used herein refers to a formulation that comprises topiramate and has a diameter of 1.5 to 4 mm, or even 2 to 4 mm.

Embodiments described herein that refer to pellets, particles, microparticles, or minitablets may be adapted to use pellets, particles, microparticles, minitablets or any combination thereof.

The term "core" as used herein is any solid material that comprises topiramate. A core may be a tablet, minitablet, granule, particle, pellet, bead, or beadlet, or even multiple minitablets, granules, particles, pellets, beads, or beadlets, or any combination thereof. The core may be coated completely or partially with a coating, which may be functional (e.g., release-controlling or enteric) or non-functional. When the term "core" refers to a plurality of individual smaller elements, the elements in the core have substantially similar or identical formulations. For example, if a formulation comprises some particles that have an enteric coating and some particles that have both an enteric coating and a bioadhesive coating, the formulation comprises two cores: one core that has an enteric coating, and a second core that has an enteric coating and a bioadhesive coating. If a formulation is a particle comprising an IR topiramate composition layered over a XR topiramate pellet, the formulation comprises two cores: a first core containing XR topiramate and a second core present as an IR topiramate coating disposed on the first core.

A "patient," "individual," or "subject" to be treated by the subject method can mean either a human or non-human animal, preferably a mammal.

The term "prevent," "preventing," or "prevention" as used herein means reducing the probability/risk of developing a condition in a subject (e.g., a human), or delaying the onset of a condition in the subject, or lessening the severity of one or more symptoms of a condition (e.g., a movement disorder) that may develop in the subject, or any combination thereof.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "$SeD_{50}$" means the dose of a drug which produces a particular side-effect in 50% of test subjects.

The term "side-effect therapeutic index" refers to the therapeutic index of a drug defined as $SeD_{50}/ED_{50}$.

The term "treat," "treating," or "treatment" as used herein means to counteract a medical condition (e.g., a movement disorder) to the extent that the medical condition is improved according to clinically acceptable standard(s). For example, "to treat a movement disorder" means to improve the movement disorder or relieve symptoms of the particular movement disorder in a patient, wherein the improvement and relief are evaluated with a clinically acceptable standardized test (e.g., a patient self-assessment scale) and/or an empirical test (e.g., PET scan). "Treat," "treating," or "treatment" as used herein includes prophylactic treatment unless the context requires otherwise.

The term "decreased incidence of side effects" refers to a reduced incidence of side effects in a patent population and not to a total absence of side effects, when measured in a comparable population.

The term "delayed release" refers to an enteric coated dosage form containing topiramate configured to delay the release of medication until the dosage form has passed through the stomach.

The term "Cmax" as used herein means maximum plasma concentration of topiramate achieved by the ingestion of a composition.

The term "Cmin" as used herein means minimum plasma concentration of topiramate achieved by the ingestion of a composition of the invention.

The term "Cavg" as used herein means average plasma concentration of topiramate achieved by the ingestion of a composition. Cavg is calculated by AUC over a 24, 48, 72, 96, 120, or 144 hr period divided by 24, 48, 72, 96, 120, or 144 hr respectively.

The term "Tmax" as used herein means the time to achieve maximum plasma concentrations produced by ingestion of a composition.

The term "AUC" as used herein means the area under the plasma concentration-time curve, as calculated by the trapezoidal rule over the 24 hr or 48 hr or 72 hr or 96 hr or 120 hr interval for all the formulations.

The term "Degree of Fluctuation (DFL)" as used herein is expressed as:

DFL=(Cmax−Cmin)/Cavg produced by ingestion of a composition.

As used in this application, the term "Cmin" and "trough levels" should be considered synonyms. Likewise, "Cmax" and "peak levels" should be considered synonyms.

IV. Dosage Forms

The effective ingredient of the various dosage forms of the invention is 2,3:4,5-Di-O-isopropylidene-beta-D-fructopyranose sulfamate (topiramate, structure depicted below). Topiramate is commercially available in the United States as Topamax® tablets of Ortho-McNeil, a division of Johnson & Johnson. Topamax® is marketed as immediate-release tablets in 25 mg, 50 mg, 100 mg and 200 mg strengths and also 15 mg and 25 mg sprinkle beads. The recommended Topamax® dose for epilepsy monotherapy in adult and children is 400 mg daily in two divided doses. The recommended total daily dose of Topamax® as an adjunctive therapy in adults with partial seizures is 200-400 mg/day in two divided doses, and 400 mg/day in two divided doses as adjunctive treatment in adults with primary generalized tonic-clonic seizures. The recommended total daily dose of Topamax® as adjunctive therapy for pediatric patients with partial seizures, primary generalized tonic-clonic seizures, or seizures associated with Lennox-Gastaut Syndrome is approximately 5 to 9 mg/kg/day in two divided doses. The recommended starting total daily dose of Topamax® as treatment for prophylaxis of migraine headache is 100 mg/day administered in two divided doses. Dosage adjustment may be necessary, especially in elderly patients with impaired renal function. (See *Physicians' Desk Reference* 59th edition, 2541-2548 (2005) and Dosage and Administration in the Topamax® package insert.)

At present, information on the relationship between plasma topiramate concentration and clinical response is relatively scarce, and no clear-cut indications for therapeutic drug monitoring have emerged. In patients receiving therapeutic doses as adjunctive therapy for epilepsy, the plasma concentration of topiramate is usually in the range of 2 to 8 µg/mL. In one study, the plasma topiramate concentration of 9 patients who became seizure-free was 5.3±2.6 µg/mL (Ferrari, et al. Ther Drug Monit 2003; 25:700-708). Another study reported mean topiramate plasma concentrations around 7 µg/mL in positive responders and 9 µg/mL in seizure-free patients (Contin, et al. Ther Drug Monit, Vol. 24, No. 3, 2002, 332-337). In a monotherapy study in 215 patients suffering from partial epilepsy, the time leading up to the first seizure (median seizure-free duration) increased from 84 days at topiramate serum concentrations<1.8 mg/L to 194 days at concentrations between 1.8 and 9.9 mg/L and to 451 days at concentrations above 9.9 mg/L, but the lower or upper limits of the therapeutic range were not established. A weak correlation was found between the plasma topiramate concentration and the percentage reduction in the average monthly rate of all generalized seizures. A tentative target range of 3 to 5 mg/L has been proposed, but a greater control of seizures may be achieved at concentrations of 10 mg/L or more (see Adin, et al. Ther Drug Monit 2004; 26:251-257). For migraine prophylaxis the plasma levels range from 1.2-4.4 µg/mL at steady state levels (Hershey, et al. Headache 2002; 42(8):810-818). In a pediatric migraine study, ninety-seven children were treated with topiramate, and 75 were reevaluated 88.7+/−35.7 days later, 41 were seen at a second follow-up, and 17 were seen at a third follow-up evaluation. The daily dose reached at second evaluation was 84.0+/−38.6 mg/day or 1.42+/−0.74 mg/kg/day. This corresponded to a mean serum level of 2.8+/−1.6 µg/mL (Hershey, et al. Headache 2002; 42(8):810-818).

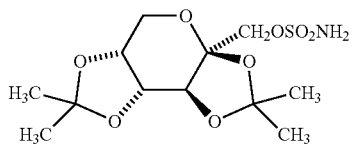

Topiramate ($C_{12}H_{21}NO_8S$)

It should be understood that mention of topiramate or a salt thereof herein embraces racemates, enantiomers, polymorphs, hydrates and solvates thereof, and topiramate may be replaced in whole or in part by a prodrug of topiramate in any of the embodiments of the invention discussed herein. Topiramate compositions of the invention are preferably suitable for administration no more than once daily. Such compositions are useful in treatment of any condition or disorder for which topiramate has therapeutic utility, but especially epilepsy and migraine.

Topiramate and its salts useful herein can be prepared by known processes, including processes disclosed in patents and other literature pertaining to topiramate.

The amount of the topiramate salt present in a composition of the invention is sufficient to provide a daily dose in one to a small plurality, for example one to about 4, of tablets to be administered at one time. Preferably, the full daily dose is delivered in a single dosage form. An amount of topiramate of about 15 to about 400 mg per tablet will generally be suitable. Preferably an amount of about 75 to about 300 mg, more preferably an amount of about 100 to about 200 mg, per tablet is desirable. Although many examples of this application use 100 mg topiramate for beagle dogs and healthy human volunteers, specific dosage amounts per tablet contemplated herein include about 15, 25, 50, 100, 150, 200, 300, and 400 mg topiramate.

A. Immediate Release (IR) Composition

By "immediate release composition" is meant a dosage form that is formulated to release substantially all the active ingredient on administration with no enhanced or extended release effect. Such a composition may be in the form of a pellet. The immediate release pellet can serve as a precursor to an extended or delayed release pellet, or be used with an extended or delayed release pellet.

The non-active ingredients and processes for preparing such immediate release pellets are well known in the art, and the present invention is not limited in these respects. See, for example, Remington's Pharmaceutical Sciences, 18th Edition, A. Gennaro, Ed., Mack Pub. Co. (Easton, Pa. 1990), Chapters 88-91, the entire disclosures of which are hereby incorporated by reference.

For instance, an immediate release pellet can be prepared by mixing topiramate with a bulking agent (filler). Additionally, one can add binding agents, disintegrating agents, antiadherents, colorants, and/or glidants to the formulation.

Bulking agents employable in these compositions may be chosen from, among others: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; dextrates; directly compressible sugars; silicates, silicon dioxide; and polyethylene glycols (CARBOWAX®). Such bulking agents are typically present in the range of about 5% to about 75% (w/w), with a preferred range of about 25% to about 50% (w/w).

Suitable disintegrants include, but are not limited to: crosslinked sodium carboxymethyl cellulose (AC-DI-SOL®), sodium starch glycolate (EXPLOTAB®, PRIMO-JEL®) and crosslinked polyvinylpolypyrrolidone (PLA-SONE-XL®). Disintegrants are used to facilitate disintegration of the pellet upon administration and are typically present in an amount of about 3% to about 15% (w/w), with a preferred range of about 5% to about 10% (w/w).

Antiadherents and glidants employable in such formulations can include talc, cornstarch, silicon dioxide, sodium lauryl sulfate, colloidal silica dioxide, glyceryl monostearate, and metallic stearates, among others.

In addition, the immediate release composition may contain one or more binders to give the pellets cohesiveness. Such binders are well known in the art, and include such substances as polyvinyl pyrrolidone, hydroxypropyl cellulose, sodium carboxymethyl cellulose, starch, maltrin, methylcellulose, hydroxypropyl methylcellulose, carboxymethyl cellulose, sucrose solution, polyvinyl alcohol, polyox, dextrose solution, acacia, tragacanth, xanthum, and locust bean gum, which may be applied wet. The binding agent may be present in the composition in an amount of from about 0.2 wt % to about 40 wt %, preferably from about 5 wt % to about 30 wt %, or from about 10 wt % to about 15 wt %.

The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the drug and other additives are granulated by addition of a binder solution. The wet mass is passed through an extruder equipped with a certain size screen, and the extrudates are spheronized in a marumerizer. The resulting pellets are dried and sieved for further applications.

One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications.

Immediate release topiramate may also be prepared by micronization. Reduced particle size, e.g. less than 5 microns, may improve bioavailability of topiramate and improve extent of exposure. Micronized topiramate can be prepared using known methods including jet milling and supercritical fluid precipitation. For example, a jet mill (Glenn Mills Inc.) can be used to micronize topiramate. Particle size analysis of the milled topiramate can be performed using a Microtrac-S3000 particle size analyzer. Typical d10, d50, and d90 sizes of a micronized topiramate sample include 1.4, 2.9, and 7.3 microns, respectively.

Alternatively, and preferably, the immediate release beadlets or pellets are prepared by solution or suspension layering, whereby a drug solution or dispersion, with or without a binder and optionally an anti-tacking agent such as talc or glyceryl mono stearate, is sprayed onto a core or starting seed (either prepared or a commercially available product) in a fluid bed processor or other suitable equipment. The cores or starting seeds can be, for example, sugar spheres or spheres made from microcrystalline cellulose or silicon dioxide or various salt crystals such as sodium citrate. The binder in the formula can be present in amounts ranging from about 0% to about 5% by weight, and preferably about 0.5% to about 2% by weight. The amount of anti-tacking agent used can be from about 0% to about 5%, preferably about 0.5% to about 2% by weight. The drug thus is coated on the surface of the starting seeds. The drug may also be layered onto the drug-containing pellets described above, if desired. Following drug layering, the resulting drug-loaded pellets are dried for further applications.

A protective layer, or overcoating, may be desired to ensure that the drug-loaded pellets do not aggregate during processing or upon storage. The protective coating layer may be applied immediately outside the core, either a drug-containing core or a drug-layered core, by conventional coating techniques such as pan coating or fluid bed coating using solutions of polymers in water or suitable organic solvents or by using aqueous polymer dispersions. OPADRY®, OPADRY II® (Colorcon) and corresponding color and colorless grades from Colorcon can be used to protect the pellets from being tacky and provide colors to the product. Different anhydride based polymers (e.g., SPHEROMER I® ((p[FA:SA] 1:4), described in U.S. Pat. No. 5,955,096 to Mathiowitz et al.) or SPHEROMER II® (described in U.S. Pat. No. 5,985,312 to Jacob et al.), both from Spherics Inc.) may also be used as protective layer. The suggested levels of protective or color coating are from about 1% to about 6%, preferably about 2% to about 3% (w/w). In certain embodiments, many ingredients can be incorporated into the overcoating formula, for example to provide a quicker immediate release, such as plasticizers: acetyltriethyl citrate, triethyl citrate, acetyltributyl citrate; dibutylsebacate, triacetin, polyethylene glycols, propylene glycol, poloxamers, and others; lubricants: talc, colloidal silica dioxide, magnesium stearate, calcium stearate, titanium dioxide, magnesium silicate, and the like.

In certain embodiments, the immediate release composition may be prepared as an uncoated tablet, or a tablet core prior to coating, comprising starch and a hydrophilic polymer acting as a matrix for a water-soluble drug or prodrug requires to have a certain minimum hardness in order to be able to resist breakage and/or attrition due to mechanical stresses imposed during a high-speed tableting operation (including all steps up to and including filling of the tablets into containers). The minimum acceptable hardness will depend on a number of factors, including the severity of the mechanical stresses, but is typically at least about 20 SCU, preferably at least about 22 SCU, more preferably at least about 24 SCU (about 17 kp).

Hardness can be increased by increasing the compression force applied by the tablet press, but only up to a certain level. At least in the case of tablets as described herein, above a certain compression force, further increases in compression force give little or no further increase in tablet hardness. There is, in other words, a maximum hardness achievable by compression of a particular starch/hydrophilic polymer/active agent composition. A starch providing a maximum hardness inadequate to withstand the mechanical stresses of a high-speed tableting operation is unsuitable for the present purpose. Certain pregelatinized starches provide a maximum hardness of 20 SCU or less; these are starches having low tensile strength (0.1 kN cm$^{-2}$ or less). Even if a maximum hardness of at least about 20 SCU is achievable, with a starch of low tensile strength it may be achievable only by use of extremely high compression forces. A requirement for such forces reduces speed and efficiency and increases cost of a tableting operation and is undesirable for these reasons.

The immediate release pellets are contemplated as being used in combination with extended release pellets and/or delayed release pellets in a single dosage form, and/or being modified to generate extended release (XR) pellets, delayed release (DR) pellets, and/or delayed and extended release (DXR) pellets in a single dosage form.

B. Delayed Release Composition (DR)

The delayed-release component has a coating that delays the release of the drug from the pellet after administration for a certain period of time. This delayed release can be accomplished by applying a coating of enteric materials to topiramate pellets or to the surface of the dosage form.

In some embodiments, topiramate pellets (e.g., IR pellets, XR pellets, or pellets with both IR and XR portions) are coated with enteric materials. The IR pellet may be a topiramate core. The IR pellet may also comprise an inert core coated with a topiramate layer. The topiramate is optionally micronized or amorphous. In specific embodiments, the enteric-coated pellets may be encapsulated to form a delayed-release sprinkle bead formulation. The coating protects the drug from breakdown in the stomach, acts as a moisture barrier coating to improve stability during storage, and masks the taste of the drug. The contents of the capsule may be sprinkled onto food for oral administration. Such compositions may be particularly useful for pediatric or geriatric use.

"Enteric materials" are polymers that are substantially insoluble in the acidic environment of the stomach, but are predominantly soluble in intestinal fluids at various specific pHs, such as 4.5 or higher. The enteric materials are non-toxic, pharmaceutically acceptable polymers, and include, for example, cellulose acetate trimellitate, shellac, polyvinyl acetal diethyl amino acetate, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, co-polymerized methacrylic acid/methacrylic acid methyl esters such as, for instance, materials known under the trade name EUDRAGIT® L12.5, L100, or EUDRAGIT® S12.5, S100, and several commercially available enteric dispersion systems (e.g., EUDRAGIT® L30D55, EUDRAGIT® FS30D, EUDRAGIT® L100-55, EUDRAGIT® S100 (Rohm Pharma), KOLLICOAT®MAE30D and 30DP (BASF), ESTACRYL® 30D (Eastman Chemical), AQUATERIC® and AQUACOAT® CPD30 (FMC)), Acryl-EZE™ (Colorcon), SPHEROMER III® (Spherics, Inc., L-DOPA grafted onto butadiene maleic anhydride, described in U.S. patent application Ser. No. 11/009,237), and Spheromer IV (Spherics, Inc., carbidopa grafted onto butadiene maleic anhydride, described in PCT/US06/24352).

The foregoing is merely a list of possible enteric coating materials, but one of skill in the art would appreciate that there are other such materials that would meet the objectives of the present invention of providing for a delayed release profile, including tailoring release based on the ambient pH environment, temporal considerations and/or other factors.

These coating materials can be employed in coating the surfaces in a range of from about 1.0% (w/w) to about 50% (w/w) of the pellet composition. Preferably, these coating materials are in the range of from about 10-20% (w/w). The pellets may be coated in a fluidized bed apparatus or pan coating, for example, in a conventional manner.

With enteric-coated pellets or tablets, there is no substantial release of topiramate in the acidic stomach environment of below about pH 4.5. The topiramate becomes available when the pH-sensitive enteric layer dissolves at a higher pH in the GI tract, after a certain delay, or after the unit passes through the stomach. The preferred delay time is in the range of about 0.5 to about 6 hours, but more preferable is about 0.5 to about 4 hours.

For example, certain DR pellets may be coated with EUDRAGIT® L30D-55, which dissolves at about pH 5.5-6.0, i.e., in the upper intestines. In other embodiments, the DR pellets may be coated with EUDRAGIT®FS30D, which dissolves at about pH 7.0, e.g., in the lower intestine and colon. Alternatively or additionally, the surface of the dosage form containing the topiramate pellets (e.g., gelatin capsule) may be coated.

Alternatively, if the dosage form comprises a solid topiramate core, the entire dosage form may be covered with an enteric coating which prevents release of the topiramate in the acidic stomach environment.

An XR pellet as described below may be additionally coated with the enteric material to generate delayed and extended release (DXR) pellets. Such a dosage form is delayed release until the drug reaches non-acidic environment, such as the upper and/or lower intestine, and thereupon releasing drugs over an extended period of time.

C. Extended Release Composition (XR)

Topiramate extended release compositions can be prepared in many different ways to achieve an extended release profile. Extended release compositions comprise at least one release rate controlling polymer. In some embodiments, the topiramate formulation contains at least two release rate controlling polymers. The ratios of the release rate controlling polymers can be adjusted to achieve the desired release profile. For example, in certain embodiments, the subject topiramate XR pellets can be prepared by coating drug layered inert pellets with release-controlling polymers. First, the inert pellet is coated with the drug layer, or a drug loaded granule is prepared, as described above. Then the active (drug loaded) pellet is coated with a release-controlling polymeric membrane. The release-controlling coating layer may be applied immediately outside the core (such as a drug-containing core or a drug-layered core), by conventional coating techniques, such as pan coating or fluid bed coating, using solutions of polymers in water or suitable organic solvents, or by using aqueous polymer dispersions. As an alternative embodiment, the release controlling membrane can separate additional drug layers on the core; for instance, after coating with the release controlling substance, another drug layer can be applied, which is followed by another release controlling layer, etc. The additional drug layers may comprise topiramate or another active agent. Suitable materials for the release-controlling layer include EUDRAGIT® RL100, EUDRAGIT® RS100, cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®), and the like. The thickness of the coating affects the release profile, and so this parameter can be used to customize the profile. The suggested coating levels are from about 1% to about 40%, about 5% to about 30% (w/w), or about 20% or about 25% in other embodiments.

For example, for topiramate salts of high water solubility as specified herein, a hydrophilic polymer matrix core can be inadequate to provide sustained release of sufficiently long duration to permit once daily administration. It is believed that such salts are readily leached out of the hydrophilic matrix when contacted by an aqueous medium such as gastrointestinal fluid. Thus in certain embodiments, it is desirable to further slow the process of drug release by providing a release-controlling coating around the tablet to produce an extended-release (XR) tablet. Such a coating may comprise a hydrophobic or water-insoluble polymer component such as ethylcellulose together with a hydrophilic or water-soluble pore-forming component such as HPMC. In addition, where tablets are to be subjected to an additional process step after compression, in particular a coating step, exposure to mechanical stresses is also greatly increased.

Alternatives to ethylcellulose and HPMC as components of a release coating layer include other cellulosic polymers (e.g., methylcellulose, hydroxypropylcellulose, hydroxyethylcellulose, carboxymethylcellulose sodium, cellulose esters such as cellulose acetate, etc.), polyvinyl acetate, polyvinyl pyrrolidone, polymers and copolymers of acrylic acid and methacrylic acid and esters thereof, polyethylene glycol, carrageenan and other gums, etc.

A release-controlling layer, if present, typically constitutes about 1% to about 15%, preferably about 2.5% to about 10%, by weight of the tablet as a whole. The hydrophobic or water-insoluble component, preferably comprising ethylcellulose, typically constitutes about 1% to about 10%, preferably about 2% to about 7%, by weight of the tablet as a whole. The pore-forming component, preferably comprising HPMC, is typically present in an amount of about 5% to about 50%, preferably about 10% to about 40%, by weight of the water-insoluble or hydrophobic component.

The coating, if present, can optionally contain additional pharmaceutically acceptable excipients such as plasticizers, dyes, etc. Illustratively, a release-controlling layer in an amount of about 2.5% to about 5% by weight of the tablet core (i.e., the tablet weight excluding the coating) comprises an ethylcellulose-based material (e.g., SURELEASE® of Colorcon) and an HPMC-based pore-forming material (e.g., OPADRY® of Colorcon) in a weight ratio of about 3:1 to about 4:1. A release-controlling layer or coating is preferably applied at a relatively uniform thickness to provide even control of release rate of the topiramate.

Alternatively or in addition, the sustained-release tablet of the invention comprises a nonfunctional coating. A nonfunctional coating can comprise a polymer component, for example HPMC, optionally with other ingredients, for example one or more plasticizers, colorants, etc. The term "nonfunctional" in the present context means having no substantial effect on release properties of the tablet, and does not imply that the coating serves no useful purpose. For example, such a coating can impart a distinctive appearance to the tablet, provide protection against attrition during packaging and transportation, improve ease of swallowing, and/or have other benefits. A nonfunctional coating should be applied in an amount sufficient to provide complete coverage of the tablet. Typically an amount of about 1% to about 10%, more typically an amount of about 2.5% to about 5%, by weight of the tablet as a whole, will be found suitable.

Uncoated tablets and cores of coated tablets of the invention can optionally contain one or more pharmaceutically acceptable excipients in addition to the starch and hydrophilic polymer components described above. Such excipients include without limitation pigments, glidants, and lubricants. Other conventional excipients known in the art can also be included. A glidant can be used to improve powder flow properties prior to and during tableting and to reduce caking. Suitable glidants include colloidal silicon dioxide, magnesium trisilicate, powdered cellulose, starch, talc, tribasic calcium phosphate and the like. In certain embodiments, colloidal silicon dioxide is included as a glidant in an amount up to about 2%, preferably about 0.2% to about 0.6%, by weight of the tablet. A lubricant can be used to enhance release of a tablet from apparatus on which it is formed, for example by preventing adherence to the face of an upper punch ("picking") or lower punch ("sticking"). Suitable lubricants include magnesium stearate, calcium stearate, canola oil, glyceryl palmitostearate, hydrogenated vegetable oil, magnesium oxide, mineral oil, Poloxamer 188, polyethylene glycol, polyvinyl alcohol sodium benzoate, sodium lauryl sulfate, sodium stearyl fumarate, stearic acid, talc, hydrogenated vegetable oil, zinc stearate and the like. In certain embodiments, magnesium stearate is included as a lubricant in an amount of about 0.1% to about 1.5%, preferably about 0.3% to about 1%, by weight of the tablet.

D. Amorphous Topiramate

Amorphous solids consist of disordered arrangements of molecules and do not possess a distinguishable crystal lattice. Topiramate may be prepared in such a way that substantially the entire active agent is present in amorphous form or in crystalline form. The amorphous topiramate has a faster release rate than crystalline topiramate, so the form affects the release profile of the dosage form. The crystalline and amorphous forms of topiramate may be mixed to generate the target release profile, and increasing the amount of amorphous topiramate increases the IR profile of the mixture. The crystalline and amorphous forms can also be distributed in the immediate and controlled release populations in the ratio of 1:20 to 1:0.5 or 20:1 to 0.5:1, more preferably from 1:5 to 1:1.

Amorphous topiramate may be prepared by known methods including, but not limited to, Phase Inversion Nanotechnology ("PIN") process (disclosed in U.S. Ser. No. 10/316,128, Ser. No. 10/696,829, Ser. No. 10/954,423 which are incorporated herein by reference), solid dispersion and milling/grinding and supercritical fluid precipitation.

A process for preparing solid, amorphous topiramate comprises mixing active agent free base or a pharmaceutically acceptable salt thereof with a solvent, such as water and methanol, and a pharmaceutically acceptable polymeric carrier; and drying to form a composition comprising amorphous active agent and polymeric carrier.

In another aspect, a pharmaceutical composition comprises active agent salt in amorphous, solid form, and polymeric carrier, prepared by the aforementioned process.

Suitable pharmaceutically acceptable polymeric carriers include, for example, hydroxypropyl cellulose, hydroxypropyl methyl cellulose methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-beta-cyclodextrin, chitosan, co(lactic/glycolid) copolymers, poly(orthoester), poly(anhydrides), polyvinyl chloride, polyvinyl acetate, ethylene vinyl acetate, lectins, carbopols, silicon elastomers, polyacrylic polymers, maltodextrins, polyvinylpyrrolidone (PVP), polyethylene glycol (PEG), and alpha-, beta-, and gamma-cyclodextrins, and combinations comprising one or more of the foregoing carriers.

Preferred polymeric carriers are one or more of polyvinylpyrrolidone, hydroxypropylmethyl cellulose, hydroxypropyl cellulose, methyl cellulose, block co-polymers of ethylene oxide and propylene oxide, and polyethylene glycol, wherein a more preferred polymeric carrier is polyvinylpyrrolidone (PVP) having an average molecular weight of about 2,500 to about 3,000,000. A most preferred polymeric carrier is polyvinylpyrrolidone having an average molecular weight of from about 10,000 to about 450,000. The more preferred polymeric carrier is hydroxypropylmethyl cellulose (HPMC) having an average molecular weight of about 2,500 to about 100,000. A most preferred polymeric carrier is hydroxypropylmethyl cellulose having an average molecular weight of from about 5,000 to about 50,000.

The polymeric carrier is preferably miscible with both the active agent free base and the salt, capable of keeping the salt in a homogeneous noncrystalline solid state dispersion after the solvent has been removed by evaporation and chemically inert with respect to the free base of the active ingredient, the salt of the free base, and the acid solution.

The active agent may be added in either free base or salt form. When the active agent is added in free base form, the process comprises adding an acid corresponding to a pharmaceutically acceptable salt of the active agent to the mixture or solution of the free base. The free base is then converted to a salt in situ, for example by addition of an inorganic or an organic acid. The acid may be added either as a gas, a liquid or as a solid dissolved into the solvent. A preferred acid is hydrogen bromide and the molar quantity of acid added to the solution of active agent free base and carrier may either be in stoichiometric proportion to the active agent free base or be in excess of the molar quantity of the active agent free base, especially when added as a gas.

The preferred range of acid added is about 1.0 to about 1.8 times the molar quantity of topiramate free base. Preferred molar ratios of active agent to hydrogen bromide are about 1:1 to 1:1.8, more preferably about 1:1.1. Although hydrogen bromide may be added as a gas, the preferred method to add the hydrogen bromide is in the form of hydrogen bromide dissolved into a solvent. It is understood that upon addition of the acid, the formed free base salt remains dissolved in solution with the polymeric carrier.

Topiramate, polymeric carrier, and solvent may be combined in any order. It is preferred that they be combined in a manner so as to form a solution of active agent salt and the polymeric carrier.

In forming a solution of polymeric carrier and solvent, heating of the solution is not necessary at lower concentrations but is strongly preferred at higher concentrations, provided that the temperature does not result in decomposition or degradation of any materials. It is preferred to add the active agent free base or active agent salt after dissolving the polymeric carrier in the solvent, suitably at about 25° C. to about 100° C., preferably at about 80° C. to about 100° C. When the active agent is added as a free base, it is preferred to form a salt at a temperature at which the final solution is clear. For the most preferred embodiments, a temperature of at least about 90° C. may result in a clear solution of the active agent salt being formed, although for other concentrations and embodiments, clear solutions are formed at other temperatures. It is preferred to add only enough heat to form a clear solution.

The ratio of active agent to the polymeric carrier can be varied over a wide range and depends on the concentration of active agent required in the pharmaceutical dosage form ultimately administered. The ratio by weight of polymeric carrier to active agent salt is about 1:20 to about 1:0.5; preferably about 1:4 to about 1:1; most preferably about 1:4.

Preferably a clear solution is formed. Upon formation of the clear solution, the process proceeds by recovering the solvent to form a solid state dispersion of the free base salt in the polymeric carrier. Any method of removal of the solvent which renders a homogeneous solid state dispersion is intended, although preferred are methods of evaporation under vacuum or spray drying. Methods of evaporation under vacuum include rotary evaporation, static vacuum drying and the combination thereof. It is understood that one skilled in the art of pharmaceutical formulations can determine a reasonable temperature at which the solvent can be removed, provided the temperature is not so high as to cause degradation or decomposition of the materials; however, it is preferred that evaporation occurs at about 90° C. to about 100° C. Evaporation of the solvent should render a solid state dispersion which is homogeneous and substantially free of solvent. By substantially free it is meant that the solid state dispersion contains less than 20% by weight of residual solvent, preferably less than 10%, more preferably less than 5%, most preferably less than 1%.

The ratio of topiramate to the polymeric carrier can be varied over a wide range and depends on the concentration of active agent required in the pharmaceutical dosage form ultimately administered. However, the preferred range of active agent in the solid dispersion is about 10% to about 50% of the total solid dispersion weight, more preferable is about 20% to about 50%, even more preferable is about 25% to about 40%, most preferable is about 33% of the total dispersion weight. In terms of weight ratio of polymeric carrier to active agent, a preferred range is about 0.4:1 to 20:1

V. Exemplary Delivery Devices

A. General Considerations

As noted previously herein, the compositions of the present invention can be in a number of different forms, such as tablets, powders, suspensions, solutions, etc. The composition is preferably in pellet/beadlet form, which can be incorporated into hard gelatin or other kinds of capsules, either with additional excipients, or alone.

The dosage formulations described herein, e.g., the cores of tablets and drug eluting devices of the invention, may contain one or more excipients, carriers or diluents. These excipients, carriers or diluents can be selected, for example, to control the disintegration rate of a tablet or drug eluting device to fit the desired release profile according to the instant invention. In addition, the one or more carriers (additives) and/or diluents may be pharmaceutically acceptable.

The phrase "pharmaceutically acceptable carrier" as used herein means a pharmaceutically acceptable material, composition or vehicle, such as a liquid or solid filter, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other materials that impart good flow properties. A lubricant can also be added if desired, such as polyethylene glycol, leucine, glyceryl behenate, magnesium stearate or calcium stearate.

The formulations can conveniently be presented in unit dosage form and can be prepared by any of the methods well known in the art of pharmacy. All methods include bringing into association the drug with the carrier or diluent which constitutes one or more accessory ingredients. In general, the formulations are prepared by uniformly and intimately bringing into association the agent with the carriers and then, if necessary, dividing the product into unit dosages thereof. It will be understood by those skilled in the art that any vehicle or carrier conventionally employed and which is inert with respect to the active agent, and preferably does not interfere with bioadhesion in embodiments employing a bioadhesive coating, may be utilized for preparing and administering the pharmaceutical compositions of the present invention. Illustrative of such vehicles and carriers are those described, for example, in *Remington's Pharmaceutical Sciences,* 18th ed. (1990), the disclosure of which is incorporated herein by reference.

Examples of carriers and diluents include pharmaceutically accepted hydrogels such as alginate, chitosan, methylmethacrylates, cellulose and derivatives thereof (microcrystalline cellulose, hydroxypropyl cellulose, hydroxypropyl methyl cellulose, carboxymethylcellulose, ethylcellulose), agarose and POVIDONE™, kaolin, magnesium stearate, starch, lactose, sucrose, density-controlling agents such as barium sulfate and oils, dissolution enhancers such as aspartic acid, citric acid, glutamic acid, tartartic acid, sodium bicarbonate, sodium carbonate, sodium phosphate, glycine, tricine, tromethamine, and TRIS.

The excipients, carriers or diluents can also be selected to control the time until a dosage form detaches from a mucosal membrane. In particular, the addition of one or more disintegrating agents will reduce the time until a tablet or drug eluting device detaches. Alternatively or in combination with the disintegrating agents, an agent that interferes with the mucosa-tablet/device adhesion can be used to control the time until detachment occurs.

As set out above, certain components, such as topiramate, of the present pharmaceutical compositions may contain a basic functional group, such as amino or alkylamino, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include but are not limited to following: 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, fumarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphate/diphosphate, picrate, pivalate, polygalacturonate, propionate, p-toluenesulfonate, salicylate, stearate, subacetate, succinate, sulfate, sulfosaliculate, suramate, tannate, tartrate, teoclate, thiocyanate, tosylate, triethiodide, undecanoate, and valerate salts, and the like. (See, for example, Berge et al., "Pharmaceutical Salts", *J. Pharm. Sci.* 66: 1-19, 1977).

In certain embodiments, the pharmaceutically acceptable salts of compounds, such as topiramate, include the conventional non-toxic salts of the compounds, e.g., from non-toxic organic or inorganic acids. Particularly suitable are salts of weak acids. For example, such conventional non-toxic salts include those derived from inorganic acids such as hydrochloric, hydrobromic, hydriodic, cinnamic, gluconic, sulfuric, sulfamic, phosphoric, nitric, and the like; and the salts prepared from organic acids such as acetic, propionic, succinic, glycolic, stearic, lactic, maleic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the components of formulations of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, and magnesium salts and the like. Representative organic amines useful for the formation of base addition salts include ethylamine, diethylamine, ethylenediamine, trometamin, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, opacifying agents, pigments, antifoaming agents, thickners, sweetening, flavoring and perfuming agents, preservatives and antioxidants can also be present in the compositions.

Pharmaceutically acceptable antioxidants may also be included. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In certain embodiments, the disintegration time of a composition (e.g., XR or DXR) may be formulated to effect a substantially zero-order release, over a period of 2, 4, 6, 8, 12, 24 or 48 hours, for instance.

In certain embodiments, multiparticulate capsules are preferred because they provide an increased surface area as opposed to a tablet or matrix, and thus allow for better release profiles and bioavailability.

However, the pellets described above can be incorporated into a tablet, in particular by incorporation into a tablet matrix, which rapidly disperses the particles after ingestion. In order to incorporate these particles into such a tablet, a filler/binder/cushioning agents must be used in the tableting process that will inhibit the destruction of the pellets during the tableting process. Materials that are suitable for this purpose include, but are not limited to, microcrystalline cellulose (AVICEL®), soy polysaccharide (EMCOSOY®), pre-gelatinized starches (STARCH 1500', NATIONAL1551®), and polyethylene glycols (CARBOWAX®). These materials should be present in the range of about 5%-75% (w/w), and preferably between about 25%-50% (w/w).

In addition, cushioning agents may be added to maintain the integrity of the beads upon compression into a tablet. Suitable cushioning agents include, but are not limited to: glyceryl mono stearate, Avicel, lactoses, and starches. These materials should be present in the range of about 5%-25% (w/w), with a preferred range of about 7%-20% (w/w).

In addition, disintegrants may be added to the tablets in order to disperse the beads once the tablet is ingested. Suitable disintegrants include, but are not limited to: cross-linked sodium carboxymethyl cellulose (AC-DI-SOL®), sodium starch glycolate (EXPLOTAB®, PRIMOJEL®), and crosslinked polyvinylpolypyrrolidone (Plasdone-XL). These materials should be present in the range of about 3%-15% (w/w), with a preferred range of about 5%-10% (w/w).

Lubricants may also be added to assure proper tableting, and these can include, but are not limited to: magnesium stearate, calcium stearate, stearic acid, polyethylene glycol, leucine, glyceryl behenate, and hydrogenated vegetable oil. These lubricants should be present in amounts from about 0.1%-10% (w/w), with a preferred range of about 0.3%-3.0% (w/w).

Tablets are formed, for example, as follows. The pellets are introduced into a blender along with AVICEL®, disintegrants and lubricant, mixed for a set number of minutes to provide a homogeneous blend which is then put in the hopper of a tablet press with which tablets are compressed.

The compression force used is adequate to form a tablet; however, it is not so great as to significantly fracture or erode the beadlets or coatings.

The subject dosage forms of topiramate may contain the same total amount of therapeutically effective amount of topiramate that is administered to a patient during a conventional topiramate treatment. In some embodiments, these dosage forms provide an effective dose over at least about 1 to about 48 hours. In other embodiments, the dosage forms provide an effective dose over about 36, about 30, about 24, about 18, or about 12 hours. For example, for the treatment of epilepsy, one conventional regimen comprises 2 times a day of 200 mg topiramate each (other dosages are available as 25, 50, 100 and 200 mg, etc.). Thus for this embodiment, the total amount of topiramate is about 400 mg (2×200 mg) in the subject once-a-day dosage forms. However, in certain embodiments, the total amount of topiramate used may be adjusted upward or downward by, for example, 5-30%, or 10-20%, etc., depending on specific patient's age, weight, gender, race, health condition, and other considerations. The altered pharmacokinetic profile of the once-a-day dosage form may also allow for lower dosages due to increased Cavg and Tmax values as compared to Topamax® tablets.

In certain embodiments, the subject pharmaceutical composition is formulated for variable dosing, such as customized dosing for individual patients (individualized therapy).

Dosage forms of the invention typically weigh at least about 400 mg. Dosage forms (such as the various shell designs of the invention) can also weigh at least 500 mg, at least 750 mg, at least 1000 mg, or at least 1250 mg, etc.

Dosage forms of the invention may be a tablet that can be of any suitable size and shape, for example, round, oval, polygonal or pillow-shaped, and optionally bear nonfunctional surface markings. Especially in the case of coated tablets, they are preferably designed to be swallowed whole and as broken into uniform pieces through breaking lines (FIG. 16). Tablets of the invention can be packaged in a container, e.g., accompanied by a package insert providing pertinent information such as, for example, dosage and administration information, contraindications, precautions, drug interactions and adverse reactions.

To produce a dosage form that can release topiramate at two or three different rates, and with preprogrammed delays, special dosage forms are used. For example, in the embodiments of the invention wherein different dosage forms of topiramate (e.g., IR, DR, XR, DXR, etc.) are designed to be released at different rates, the drugs may be formulated as bilayer (or other multilayer) tablets or shells (e.g., stacked layer of cakes, each may represent an independent formulation). Alternatively, the drugs may be formulated as a tablet within a tablet or bead (not limited to two nested layers). Optionally, a bioadhesive layer may be coated over part or all of a gel capsule (or other forms of delivery device) to enhance the stay of the device within a certain area of the GI tract, such as the intestine.

B. Exemplary Delivery Devices/Forms

Some specific tablets or gel capsules designed are described below for illustration purpose. These designs are by no means limiting, and a skilled artisan can readily envision other equivalent designs based on the general teachings described herein.

In certain embodiments, the drugs may be formulated into a core tablet held in a recessed fashion within an annular ring of drug material. Such a dosage form is described in U.S. patent application Ser. No. 10/419,536 entitled "Dosage Form with a Core Tablet of Active Ingredient Sheathed in a Compressed Angular Body of Powder or Granular Material, and Process and Tooling for Producing It," filed on Apr. 21, 2003 and Ser. No. 10/379,338 entitled "Controlled Release Dosage Forms," filed on Mar. 3, 2003 and are incorporated herein by reference. This design may be used for many embodiments of the subject dosage forms. For example, the outer annular ring is formulated for either immediate release (IR) or extended release (XR) delivery for a desired amount of time. The inner core(s) of the dosage form may be released after a delay which may be formulated for the desired release profile. The enteric coating covers the tablet to delay drug delivery until the tablet enters a non-acidic environment.

Other embodiments of the invention use the dosage form described in U.S. patent application Ser. No. 10/191,298 entitled "Drug Delivery System for Zero-Order, Zero-Order Biphasic, Ascending or Descending Drug Delivery," filed on Jul. 10, 2002, incorporated herein by reference.

In other embodiments, the tablet is a compressed tablet. In a certain embodiment, the core of the tablet is a slow-eroding active core containing topiramate and other pharmaceutical excipients. The core is coated with a bioadhesive polymer layer and/or an enteric polymer. Once the enteric polymer layer is dissolved, the active core starts to release its contents. The bioadhesive layer is selectively adhesive to intestine or colon, such that the content of the active core may be released over a prolonged period of time.

Alternatively, the IR portion of the dosage form is formulated as a matrix for embedding one or more other portions of the same dosage form (DR, XR, DXR, etc.). The IR may be coated by enteric layer to avoid release in upper GI tract. Each controlled release portion (DR, XR, DXR, etc.) is optionally coated by a bioadhesive coat and/or a delayed release coat. Each CR portion may be formed as microparticles (e.g., beads) suspended in the first portion (e.g., IR portion) matrix. The disintegration of the matrix leads to the release of the embedded microparticles, which may re-adhere to the gut or other tissues (if coated by bioadhesive layer), and provided for sustained release.

Another embodiment of this invention may be achieved by formulating the drug as different pellets/beads, with different release profiles and delays, and delivering the mixture of the pellets (e.g., IR, DR, DXR, etc.) in a shell using methods commonly known in the art. With this combination, the IR pellets are designed to provide an effective blood level soon after the start of the drug release, which is subsequently maintained by the DR and/or XR combinations. The DR portion provides an immediate release after a delay. If XR pellets are also used, the XR portion provides an extended release profile that maintains the effective blood level of topiramate throughout the remaining course of the day. Furthermore, the proportions of the different types of pellets/beads may be altered or customized by a skilled artisan (e.g., qualified physician or pharmacologist), based on an individual patient's characteristics, such as weight, age, gender, ethnicity, and/or specific genetic backgrounds. Such customization may be effected with the aid of, or automatically executed by, a computer program based on relevant parameters such as those described above.

In certain embodiments of the invention, the drug is formulated as a single population of pellets/beads comprising multiple layers on each pellet/bead with different release profiles. For example, a CR bead/pellet may be further layered with an IR topiramate layer. Such pellets provide an effective blood level soon after the start of the drug release, which is subsequently maintained by the inner XR layer or layers. The pellets may be provided in capsule. The capsule is optionally coated with an enteric coating.

In certain embodiments, the drug-releasing beads are characterized by a dissolution profile wherein 0 to 20% (e.g., 1-20%) of the beads undergo dissolution and release the drug in 0 to 2 hours, 20 to 40% undergo dissolution and release the drug in 2 to 4 hours, 40 to 60% exhibit dissolution and release in 4 to 6 hours, 60 to 80% in 6 to 8 hours, and 80 to 100% in 8 to 10 hours or longer. The drug-releasing beads can include a central composition or core comprising a drug and pharmaceutically acceptable composition forming ingredients including a lubricant, antioxidant, absorption enhancers, and buffer. The beads comprise increasing doses of drug, for example, 0.1 mg, 0.2 mg, 0.5 mg, and so forth to a high dose. For sustained release embodiments, the beads may be coated with a release rate-controlling polymer that can be selected utilizing the dissolution profile disclosed above. The manufacture of the beads can be adapted from, for example, Liu et al., *Inter. J. of Pharm.* 112: 105-116, 1994; Liu et al., *Inter. J. of Pharm.* 112: 117-124, 1994; *Pharm. Sci.*, by Remington, 14th Ed. pp. 1626-1628 (1970); Fincher et al., *J. Pharm. Sci.* 57: 1825-1835, 1968; and U.S. Pat. No. 4,083,949.

Thus according to this aspect of the invention, any drug to be delivered (e.g., topiramate), optionally including a bioadhesive polymer composition, and/or pharmaceutically acceptable excipients, may be formulated using the subject granulation-extrusion-spheronization process into multiparticulate pellets, which in turn may be dispersed in certain matrix materials, or simply encapsulated in capsules, e.g., according to the various embodiments disclosed above.

Specifically, appropriate amounts of the different ingredients are first weighed and mixed.

Suitable excipients for use in the subject granulation-extrusion-spheronization process include: Starcap-1500, starch-1500, and glyceryl monostearate. In certain embodiments, the mixture is substantially free of microcrystalline cellulose.

In an exemplary embodiment, about 10-90%, about 20-80%, about 50-80% (v/v), or even about 70-of the mixture (and the pellets formed therefrom) is topiramate or a salt thereof, rather than excipients or polymers. Such loadings can be achieved using any drug or combination of drugs that are suitably cohesive, plastic, and engage in hydrogen bonding. It has been observed that topiramate is an example of such a drug, though others will be known to or can be easily identified by those of skill in the art.

These different ingredients can then be blended together in any suitable device, such as a planetary type mixer (e.g., Hobart Mixer with a 5-qt mixing bowl, operating at the speed setting #1, for about 5-15 min.). Optionally, the blending process is done in small volume to reduce any possible loss of the ingredients due to their non-specific adherence to the blending device. The blending step is typically done to ensure the formation of a uniform dry mix of the ingredients, typically over a period of, e.g., 5-15 min.

The dry mix is then granulated, e.g., under low shear with a granulation fluid, so as to form a wet granulation. Granulation fluids may be purified water, an aqueous solution of a mineral or organic acid, an aqueous solution of a polymeric composition, a pharmaceutically acceptable alcohol, a ketone or a chlorinated solvent, a hydro-alcoholic mixture, an alcoholic or hydro-alcoholic solution of a polymeric composition, a solution of a polymeric composition in a chlorinated solvent or in a ketone, etc. or any suitable mixture thereof.

In certain embodiments, the granulation process is conducted in a small volume, such as in a 500-mL cylindrical vessel.

In certain embodiments, the granulation process is conducted with manual mixing, or conducted mechanically, e.g., in a planetary type mixer (such as a Hobart Mixer with a 5-qt mixing bowl) or high shear mixer. If the Hobart Mixer is used, it can be operated at its speed setting #1, depending on the batch size. Other types of mechanical mixers may also be used, with their respective appropriate settings, to achieve substantially the same result.

Once the wet granulation is formed, it is extruded through the screen of a screen-type extruder. In certain embodiments, a Caleva Model 20 (or Model 25) Extruder may be used, operating at 10-20 rpm, and forming breakable wet strands ("the extrudate"). The screen aperture may be set at 0.8, 1, or 1.5 mm. Other types of extruders may be used to achieve substantially the same result.

The extrudate is then spheronized in a spheronizer. For example, a Caleva Model 250 spheronizer equipped with a 2.5-mm spheronization plate may be used, which may be operated at a speed of about 1000-2000 rpm, typically for 5-10 min., in order to form spheronized pellets. Other types of spheronizers may be used to achieve substantially the same result.

The spheronized pellets are then dried. The drying may be conducted in a fluidized bed drier, such as a Vector MFL.01 Micro Batch Fluid Bed System. If the Vector drier is used, it may be operated at an inlet air flow rate of 100-300 lpm (liters per minute) and an inlet air temperature of about 50° C. Alternatively, the pellets may be dried in an ACT (Applied Chemical Technology) fluidized bed drier, operating at an inlet air flow rate of 140-150 fpm (foot per minute) and an inlet air temperature of 104° F. Other types of driers may also be used to achieve substantially the same result. Depending on the specific type of drugs/compositions, the drying temperature for a drier similar to the Vector drier may be between 35-70° C., or 40-65° C., or 45-60° C., or 45-55° C., etc. The drying temperature for a drier similar to the ACT drier may be between 70-140° F., or 80-130° F., or 90-120° F., or 100-110° F., etc.

In yet another embodiment, the spheronized pellets may be dried in an oven, such as a Precision gravity oven, operating at about 50° C., for 4-48 hrs, or 8-24 hrs. Depending on the specific type of drugs/compositions, the oven drying temperature for a drier similar to the Precision gravity oven may be between 35-70° C., or 40-65° C., or 45-60° C., or 45-55° C., etc.

The dried pellets are then screened and/or classified. This can be done by using a stack of sieves, such as stainless steel sieves U.S. standard mesh sizes 8, 10, 12, 14, 16, 18, 20, 25, 30, 40, 45, or 60, etc., and using a mechanical sieve shaker (e.g., W. S. Tyler Sieve Shaker Ro-Tap Rx-29, operated for 5 min.). Particle size and distribution of pellet formulations can then be analyzed, and the classified pellets ranging from 0.25 mm (mesh # 60) to 2 mm (mesh # 10) may be selected for use or future formulation, such as additional film coating or other experimentation.

In certain embodiments, 0.6 to 1.4 mm topiramate pellets are produced by granulation, extrusion, spheronization, and drying.

In certain embodiments, the pellets are granulated with at least one release-rate controlling polymer (see polymers described and listed above in connection with the Extended Release Composition (XR) and below for the CR coating).

In certain embodiments, the selected pellets may be film-coated, e.g., with a delayed-release coating (such as an enteric coating), a controlled-release (CR) coating, a bioadhesive polymeric composition, and/or a dispersion-promoting coating, etc. The selected pellets may also be coated with other drug layers.

For example, the pellet core may be optionally surrounded by a CR coating, such as polymeric substance based on acrylates and/or methacrylates, e.g., a EUDRAGIT™ polymer (sold by Rohm America, Inc.). Specific EUDRAGIT™ polymers can be selected having various permeability and water solubility, which properties can be pH dependent or pH independent. For example, EUDRAGIT™ RL100, EUDRAGIT™ NE, and EUDRAGIT™ RS100 are acrylic resins comprising copolymers of acrylic and methacrylic acid esters with a low content of quaternary ammonium groups, which are present as salts and give rise to the permeability of the lacquer films. EUDRAGIT™ RL100 is freely permeable and EUDRAGIT™ RS 100 is slightly permeable, independent of pH. In contrast, the permeability of EUDRAGIT™ L is pH dependent. EUDRAGIT™ L is an anionic polymer synthesized from methacrylic acid and methacrylic acid methyl ester. It is insoluble in acids and pure water, but becomes increasingly soluble in a neutral to weakly alkaline solution by forming salts with alkalis. Above pH 5.0, the polymer becomes increasingly permeable. If desired, two or more types of polymeric substances may be mixed for use as the CR coating. Other polymers suitable for CR coatings, such as ethyl cellulose and cellulose acetate, polyvinyl acetate, and cellulose acetate butyrate can also be used. In certain embodiments, the CR coating may comprise one or more suitable polymers, such as a combination of two or more of the polymers discussed above. In particular embodiments, at least one further drug-containing layers is applied over the CR coating. These drug layers may be CR layers or IR layers.

Optionally, the pellets may also be coated by a bioadhesive polymeric composition. The adhesive material may facilitate the adhesion of the pellets to a desired surface, such as a preferred GI tract surface. For example, the pellets/beads may be coated by a top-layer of a bioadhesive polymer such as Carbopols, Gantrez, Chitin, SPHEROMER™ I [p(FASA)], SPHEROMER II® (described in U.S. Pat. No. 5,985,312 to Jacob et al.), SPHEROMER™ III (L-DOPA grafted onto butadiene maleic anhydride, described U.S. patent application Ser. No. 11/009,237), SPHEROMER™ IV (carbidopa grafted onto butadiene maleic anhydride, described in PCT/US06/24352), or mixtures thereof.

In certain embodiments, the functions of a CR coating and bioadhesive coating can be combined in a single layer by using a mixture of polymers including a bioadhesive polymer and a polymer suitable for controlled release, i.e., a single layer may be both the CR layer and the bioadhesive layer of a particle.

Optionally, the pellets can also be film-coated with an additional layer of a so-called "non-functional polymer," such as OPADRY™ II, EUDRAGIT™ E, hydroxypropylmethyl cellulose, hydroxypropyl cellulose, polyvinyl alcohol, polyvinylacetate, polyanhydride, waxes, talc, glyceryl monostearate, magnesium stearate etc. This layer may serve as a dispersion-promoting coating that inhibits clumping and aggregation of the particles during dispersion. In embodiments wherein the pellets are further compressed with excipients to form tablets, this layer is preferably sufficiently strong or resilient to remain substantially intact during the compression process. This layer may also be protected by including a cushioning material among the excipients of the tablet matrix.

The coating material (such as bioadhesive polymers and/or functional/nonfunctional polymers) may be dissolved in an appropriate solvent, such as methylene chloride (e.g., for SPHEROMER™ I), methanol (e.g., for SPHEROMER™ III), a binary mixture of methanol and methylene chloride (e.g., for SPHEROMER™ I and SPHEROMER™ III), methanol or a binary mixture of ethanol and water (3:1 v/v) (e.g., for SPHEROMER™ IV), or methanol, ethanol, or isopropanol, or their binary mixture with acetone (e.g., functional or non-functional polymer).

The film coating may be performed in a fluidized bed coater, such as a Vector MFL.01 Micro Batch Fluid Bed System, equipped with a Wurster insert, operating at an inlet air flow rate of 100-300 lpm (liters per minute), and an inlet air temperature of about 25-45° C., or about 30-40° C., depending on the specific drugs and coatings (e.g., 25-30° C. for SPHEROMER™ I-coated topiramate; about 35° C. for SPHEROMER™ III-coated topiramate, etc.). If the Vector System is used, the pellets may be pre-warmed at 35° C. for 2-5 min., and after film-coating, post-dried at about 30° C. for about 15-30 min.

Alternatively, pellets may be coated in a fluid bed processor, such as a Fluid Air Model 5 fluid bed processor equipped with a Wurster insert, operating at an inlet air flow rate of about 70 cfm (cubic foot per minute) and an inlet air temperature of about 35° C. For this type of fluid bed processor, the pellets may be pre-warmed at 40° C. for 5-7 min., and after film-coating, post-dried at about 35° C. for about 30 min.

Other types of coaters (pan coaters) may also be used to achieve substantially the same result.

Different lots of the same pellets produced using the subject method may optionally be mixed, e.g., by using a blender (such as a GlobePharma Maxiblend Blender equipped with an 8-qt stainless steel V-shell).

In certain embodiments, different types of pellets may be mixed. For example, some pellets may have no coating other than a core comprising the effective ingredients. Other pellets, such as those identically made, may have additionally been coated by one or more types of coatings, e.g., bioadhesive coating, delayed-release coating, controlled-release coating, and/or dispersion-promoting coating, etc.

In certain embodiments, pellets produced using the methods of the invention may be encapsulated in capsules, such as hard gelatin capsules or pullulan capsules (NPcaps™), each with a predetermined amount of effective ingredients.

In particular embodiments, the dosage form is a capsule containing only one type of pellet.

In certain embodiments, pellets produced using the methods of the invention may be dispersed in a matrix material to assist the delivery of the effective ingredients of the pellets.

In an alternative embodiment, the particles are not embedded within the inactive material, but are instead disposed loose in a capsule that dissolves and releases the particles in the GI tract.

In an alternative embodiment, the particles described herein above are disposed on the surface of a bioadhesive film. The film may optionally be dried or cured, e.g., without disrupting the particle adhesion. The film may then be folded and placed in a capsule for administration to a patient. If needed the capsule containing the active containing bioadhesive film is coated with delayed release coating to allow the film to adhere to the proximal part of the GI tract. If needed, the film may first be folded or cut to a suitable shape or size. Once administered to a patient, the capsule releases the film, which then rehydrates (if necessary) and adheres to a mucosal surface, allowing the particles adhered thereto to release the active components.

According to a related aspect of the invention, any drug to be delivered (e.g., topiramate), optionally including a bioadhesive polymer composition, and/or pharmaceutically acceptable excipients, may also be formulated as a multi-layer tablet.

Specifically, different ingredients (such as those described above) are weighed and mixed. These ingredients, possibly with the exception of any lubricants, can then be blended together in any suitable device, such as an end-over-end ATR rotator (e.g., model RKVS), or a planetary type mixer (e.g., Hobart Mixer). Optionally, the blending process is done in small volume to reduce any possible loss of the ingredients due to their non-specific adherence to the blending device. The blending step is typically done to ensure the formation of a uniform dry mix of the ingredients, typically over a period of, e.g., 5-15 min.

Once the wet granulation is formed, it is dried. In certain embodiments, the wet granulation is dried in an oven (e.g., a Precision gravity oven, operating at about 50° C., for 8-24 hrs; or similar appropriate conditions for other types of ovens). Alternatively, the granulation may be dried in a fluidized bed drier, such as a Vector MFL.01 Micro Batch Fluid Bed System, operating at an inlet air flow rate of 100-300 lpm (liters per minute) and an inlet air temperature of about 50° C. The drying temperature is generally around 50° C. However, depending on different types of drugs/compositions, the temperature may be 35-70° C., or 40-65° C., or 45-60° C., or 45-55° C., etc.

The dried granulation is then grinded, e.g., by using a pestle in a mortar, optionally followed by sieving the ground material, e.g., through an appropriate-sized screen (such as a U.S. Std. mesh # 60 screen), depending on the desired size of the granules.

At this point, the sieved granulation may be blended with a lubricant. In certain embodiments, the blending is conducted using an end-over-end ATR rotator (e.g., model RKVS). In certain embodiments, the blending is conducted using a planetary type mixer (e.g., Hobart Mixer, operating at the speed setting #1, for 5-15 min.). As a result, a uniformly lubricated dry mix is formed, which is then ready for compression.

Optionally, before compression, the lubricated dry mix may be passed through a sieve or screen, e.g., a U.S. Std. mesh # 60 screen.

Different components of the pharmaceutical composition (e.g., the effective ingredients, any bioadhesive polymers, or other coatings, etc.) may be prepared as a mixture or separately using the subject methods. Once the dry mixes are formed, they can be compressed into single layer or multi-layer tablets. For example, the lubricated dry mix may be pressed into tablets, such as by using a single-station manual tablet press (e.g., GlobePharma Manual Tablet Compaction Machine MTCM-I, equipped with adequate die and punch set). If the GlobePharma machine is used, tablets may be prepared, e.g., at a pressure ranging from 250 to 4000 pounds per square inch (psi), and a compression time of, e.g., 1 to 8 seconds. Other machines may also be used to achieve substantially the same result.

Alternatively, in certain embodiments, tablets may be produced with wet granulation of active ingredients followed by direct compression.

In certain embodiments, multilayer tablets may be produced. In these embodiments, a single-station manual tablet press (e.g., GlobePharma Manual Tablet Compaction Machine MTCM-I, equipped with adequate die and punch set or Korsch multilayers tablet machine) may be used in several steps to produce the multilayer tablets. For example, for a bilayer tablet, the compression process may include:

(1) adding the first layer blend into the die cavity, optionally followed by manually tapping it using a stainless steel spatula;

(2) adding the second layer blend into the die cavity;

(3) pre-compressing the two layers together, e.g., at a pressure ranging from 250 to 500 pounds per square inch (psi) and a compression time of, e.g., 1 to 5 seconds.

(4) compressing the pre-compacted layers together, e.g., at a pressure ranging from 1000 to 4000 pounds per square inch (psi) and a compression time of, e.g., 1 to 8 seconds.

The process can be repeated or modified if more than two layers of ingredients are to be used.

In certain embodiments, the individual layers of the multilayer tablet are formulated with different release rates, thereby providing a drug concentration gradient within the tablet. In some embodiments, about 70% of the drug is present in a central core layer and about 30% of the drug is present in one or more peripheral layers. In other embodiments, about 10-80%, about 20-70%, or even about 30 to about 60% of the drug is present in a central core layer and the remaining portion of the drug is present in one or more peripheral layers.

In certain embodiments, the tablets containing beads may be biconvex, oval, capsule shape (LCT, Longitudinally compressed tablet), or any other suitable shape.

In certain embodiments, the tablet can be made with a pre-compressed insert with effective ingredients. Such pre-compressed inserts may be produced with direct compression. The same press machine may be used for this process. For example, if using the GlobePharma Manual Tablet Compaction Machine MTCM-I machine, tablet inserts may be prepared, e.g., at a pressure ranging from 500 to 1000 pounds per square inch (psi), and a compression time of, e.g., 1 to 2 seconds. Other machines may also be used to achieve substantially the same result. The pre-compressed insert may be used as one of the layers (e.g., the second layer) in the tablet, or embedded in the middle of another layer (e.g., the second layer).

Optionally, the tablets may be coated with one or more coating compositions, such as in the form of successive layers. The coating compositions may include bioadhesive layers, delayed release layers, controlled-release layers, and/or other functional/non-functional polymers etc. For example, tablets may be film-coated for this purpose, using a pan coater (e.g., O'Hara Labcoat, operating at an inlet air flow rate of about 60 cfm (cubic foot per minute) and an inlet air temperature of about 35° C.). The tablets may be pre-warmed at 35° C. for 5-10 min., and after film coating, may be post-dried at about 30° C. for about 15-30 min. Other coaters may also be used to achieve substantially the same result.

Additional details of the granulation-extrusion-spheronization process are described (with examples) in the co-pending U.S. application Ser. No. 11/474,134, filed on Jun. 23, 2006 (the teachings of the entire referenced application are incorporated herein by reference).

These various embodiments are only a sample of numerous possible configurations to deliver the subject dosage forms. Other variations may be readily envisioned based on the principles and teachings of the instant specification. For example, various other drug-eluting devices are described in U.S. Pat. Nos. 4,290,426, 5,256,440, 5,378,475, 5,773,019 and 6,797,283, the contents of which are incorporated herein by reference.

In these and other embodiments of the invention, the various bioadhesive coatings that can be used are described in detail in the section below.

Many of the different embodiments described above may be implemented by using biodegradable devices. Various slow release polymeric devices have been developed and tested in vivo in recent years for the controlled delivery of drugs. A variety of biocompatible polymers (including hydrogels), including both biodegradable and non-degradable polymers, can be used to form an implant for the sustained release of a subject pharmaceutical composition at a particular target site. The biodegradable polymers undergo chemical decomposition to form soluble monomers or soluble polymer units. The biodegradation of polymers usually involves chemically or enzymatically catalyzed hydrolysis. Representative biodegradable polymers comprise a member selected from biodegradable poly(amides), poly(amino acids), poly(esters), poly(lactic acid), poly(glycolic acid), poly(orthoesters), poly(anhydrides), biodegradable poly(dehydropyrans), and poly(dioxinones). The polymers are known to the art in Controlled Release of Drugs, by Rosoff, Ch. 2, pp. 53-95 (1989); and in U.S. Pat. Nos. 3,811,444; 3,962,414; 4,066,747; 4,070,347; 4,079,038; and 4,093,709.

In certain embodiments, representative dosage forms include hydrogel matrix containing a plurality of tiny pills or other particles. The hydrogel matrix comprises a hydrophilic polymer, such as selected from a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, polyethylene oxide, alginates, xanthum gum, guar gum, gelatin and a hydrophilic colloid. The hydrogel matrix comprises a plurality of tiny pills or particles (such as 4 to 50), each tiny pill or particle may comprise a different portion of the subject topiramate compositions (e.g., IR, XR, DR, DXR, etc.). Representative of wall-forming materials include a triglyceryl ester selected from glyceryl tristearate, glyceryl monostearate, glyceryl dipalmitate, glyceryl laureate, glyceryl didecenoate and glyceryl tridecenoate. Other wall forming materials comprise polyvinyl acetate phthalate, methylcellulose phthalate, and microporous vinyl olefins. Procedures for manufacturing tiny pills are disclosed in U.S. Pat. Nos. 4,434,153; 4,721,613; 4,853,229; 2,996,431; 3,139,383 and 4,752,470, which are incorporated by reference herein.

In still other embodiments, the invention employs a dosage form comprising a polymer that releases a drug by diffusion, flux through pores, or by rupture of a polymer matrix. The dosage form matrix can be made by procedures known to the polymer art. An example of providing a dosage form comprises blending a pharmaceutically acceptable carrier, like polyethylene glycol, with a known dose of the subject pharmaceutical composition, and adding it to a silastic medical grade elastomer with a cross-linking agent, like stannous octanoate, followed by casting in a mold. The step is repeated for each successive layer. The system is allowed to set, e.g., for 1 hour, to provide the dosage form. Representative polymers suitable for manufacturing the dosage form include olefin and vinyl polymers, condensation polymers, carbohydrate polymers, and silicon polymers as represented by poly(ethylene), poly(propylene), poly(vinyl acetate), poly(methyl acrylate), poly(isobutyl methacrylate), poly(alginate), poly(amide), and poly(silicone). The polymers and manufacturing procedures are known in Polymers, by Coleman et al., Vol. 31, pp. 1187-1230 (1990); Drug Carrier Systems, by Roerdink et al., Vol. 9, pp. 57-109 (1989); Adv. Drug Delivery Rev., by Leong et al., Vol. 1, pp. 199-233 (1987); Handbook of Common Polymers, Compiled by Roff et al., (1971) published by CRC Press; and U.S. Pat. No. 3,992,518.

In some embodiments, the invention employs a dosage form comprising a capsule. The capsules generally include two prefabricated cylindrical shells (a cap and a body), one end of each of which is closed, and the other end of which is open. The shells are telescopically joined so that they have a partial overlap of the cap-side wall with the body-side wall. The topiramate composition is loaded into the body of the capsule which is then joined with a cap to close the capsule. Such capsules are generally prepared from an edible natural substance such as gelatin or hydroxypropylmethyl cellulose.

In some capsule formulations, the joined cap and body of each capsule is banded at their seam of overlap with a gelatin band or film to prevent reopening after filling.

In some capsule formulations, the capsules are not banded at their seam of overlap.

In some embodiments, an unbanded capsule is sealed with a sufficient amount of sealing composition. Such sealing compositions comprise a film-forming material, a plasticizer and a filler. The sealed capsule may be further coated with at least one other coating as described herein.

Suitable film-forming materials include hydrophilic materials such as starch, water-soluble chemical derivatives of starch, gelatin, phthalated gelatin, gelatin succinate, cross linked gelatin, shellac, sunflower protein, soybean protein, cotton seed proteins, peanut proteins, rape seed proteins, blood proteins, egg proteins, acrylated proteins and other vegetable proteins, carrageenans, guar gum, agar-agar, gum arabic and related gums, pectin and other water-soluble polysaccharides, water-soluble derivatives of cellulose, alkylcelluloses, hydroxyalkylcelluloses and hydroxyalkylalkylcelluloses, methylcellulose, hydroxymethylcellulose, hydroxyethylcelulose, hydroxypropylcellulose, hydroxyethylmethylcellulose, hydroxypropylmethylcellulose and hydroxybutylmethylcellulose, cellulose esters and hydroxyalkylcellulose, esters including cellulose acetylphthalate (CAP), and hydroxypropylmethylcellulosephthalate (HPMCP), carboxyalkylcelluloses, carboxyalkylalkylcelluloses, and carboxyalkylcellulose esters including carboxymethylcellulose, and their alkali metal salts, water-soluble synthetic polymers including polyacrylic acids and polyacrylic acid esters, polymethacrylic acids and polymethacrylic acid esters, polyvinyl acetates, polyvinyl alcohols, polyvinyl acetate phthalates (PVAP), polyvinyl pyrrolidone, polycrotonic acids, cationically modified acrylates and methacrylates; and any combination thereof. The film-forming material may be present in the sealing material at a concentration of about 50-98%, preferably about 75-95%, based on the weight of all the components.

Suitable plasticizers are compatible with the capsule and with the film former. Examples of suitable plasticizers include polyalkylene oxides, such as polyethylene glycols, polypropylene glycols, polyethylene-propylene glycols; poloxamers, organic plasticizers with lower molecular weights, such as glycerol, glycerol monoacetate, diacetate or triacetate; propylene glycol, sorbitol, sodium diethylsulfosuccinate, triethyl citrate, acetyltriethyl citrate, tributyl citrate, acetyltributyl citrate, dibutylsebacate, triacetin, etc. In certain embodiments, a plasticizer may be present in the sealing composition in concentrations ranging from about 0.5% to about 15%, preferably ranging from about 0.5% to about 5%, based on the weight of all the components.

Suitable fillers are typically particulate materials that are non-swellable in water, in that they preferably swell in volume by less than 20%, 10%, 5%, 3%, 2% or 1% after exposure to water for an hour at room temperature. Examples of such fillers include metal oxides, such as magnesium, aluminum, silicon, titanium oxides (e.g., silicon dioxide), as well as various grades of talc, microtalc and other micronized materials. The filler may be present in the sealing composition at concentrations of up to 50%, may be used, preferably in the range from about 3% to about 20%, based on the weight of all the components.

In certain embodiments, the ratio of film-forming material to plasticizer to filler is selected such that sealing composition is pliable and does not crack. Preferably, the sealing composition is compatible with the capsule itself (e.g., with gelatin or HPMC).

A particularly preferred sealing composition is Opadry Clear 03K19229.

In certain embodiments, coloring agents may be added in concentrations ranging from about 0.001% to about 10%, preferably from about 0.5% to about 3%, based on the weight of all the components.

A sufficient amount of the sealing composition is applied such that the capsule remains sealed over time, particularly with changes in temperature and humidity. Preferably, enough sealing composition is applied to inhibit cracking of the sealing layer with expansion and contraction (e.g., from physical contact, changes in environmental humidity and/or temperature, etc.).

Prior to application to a capsule, a sealing composition may be diluted in alcoholic and/or aqueous solvent for ease of application. Preferably, the solvent comprises one or more alcohols. Suitable alcohols include methanol, ethanol, n-propanol, i-propanol and butanol. Typically, the diluent solution comprises at least 50%, at least 60%, at least 70%, at least 80%, at least 85%, at least 90% or at least 95% by volume of alcohol. When water is present in the diluent, it typically comprises 5-20% or 5-15% by volume of the diluent.

Sealing compositions are applied under conditions such that the sealing composition can sufficiently dry before one or more coatings are applied. In certain embodiments, the temperature ranges from 20° C. to 100° C., but typically ranges from 30° C. to 60° C. or from 35° C. to 50° C. Independently or in addition to the temperature, sufficient air flow is maintained over the capsules to facilitate drying of the sealing composition (e.g., 50-100 cfm, 60-80 cfm). Other parameters such as application rate (pump speed), atomization air pressure and pan speed are controlled so as to be compatible with the temperature and air flow.

In certain embodiments, one or more of the coatings described herein is applied after the sealing composition is applied. Typically, less than 30 minutes, 25 minutes, 20 minutes, 15 minutes, 10 minutes, 7 minutes, 5 minutes, 4 minutes, 3 minutes, 2 minutes or even 1 minute elapse after the sealing composition is applied and before the additional coatings are applied In some embodiments, the invention also provides methods of forming a capsule comprising topiramate, comprising loading a capsule body with an active agent, joining the capsule body with a cap to form a capsule, sealing the capsule body and the cap with a sufficient amount of the sealing composition and optionally coating the capsule.

Some specific tablets or gel capsules forms are described below for illustration purpose. These designs are by no means limiting, and a skilled artisan can readily envision other equivalent designs based on the general teachings herein.

In one example, as shown in the schematic drawing of FIG. 1A (not necessarily to scale), the tablet is a longitudinally compressed tablet. The core of the tablet is a slow-eroding active core 1 with topiramate and other pharmaceutical excipients. The sides of the core are coated with an impermeable polymer layer 4, while the two ends of the core are coated with an insoluble plug 2 and an enteric polymer plug 3, respectively. The enteric polymer plug 3 will only dissolve in a pH environment of about pH 4.5 and higher, such as those found in intestine or colon. Once the enteric polymer layer 3 is dissolved, the active core 1 starts to release its contents. The impermeable polymer layer 4 encases the core, such that the content of the active core 1 may be released over a prolonged period of time.

Figure 1B:
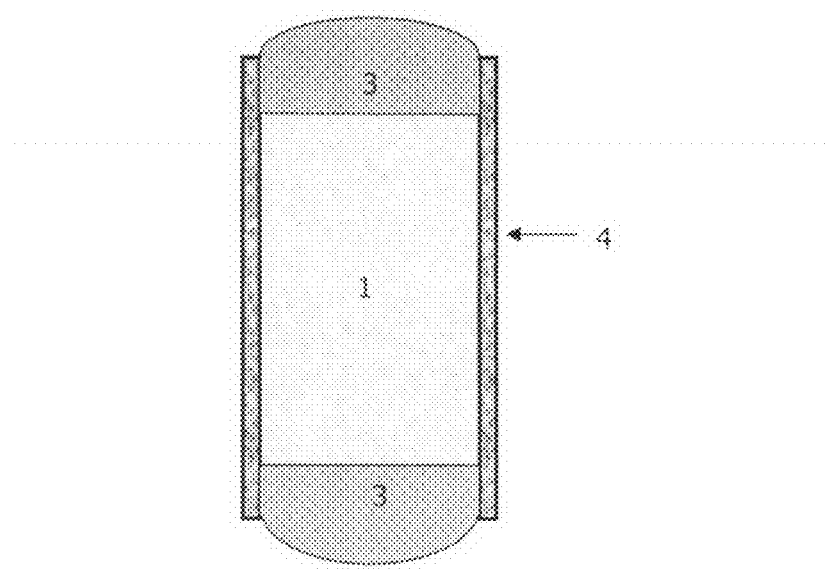

FIG. 1B shows a slight variation of the device depicted in FIG. 1A, in that the insoluble plug 2 in replaced by a second enteric polymer plug 3. According to this embodiment, both enteric polymer plugs 3 will dissolve in relatively higher pH environments, either substantially simultaneously, or at different time, such that the rate of release from the slow-eroding active core 1 may be regulated.

Figure 1C:
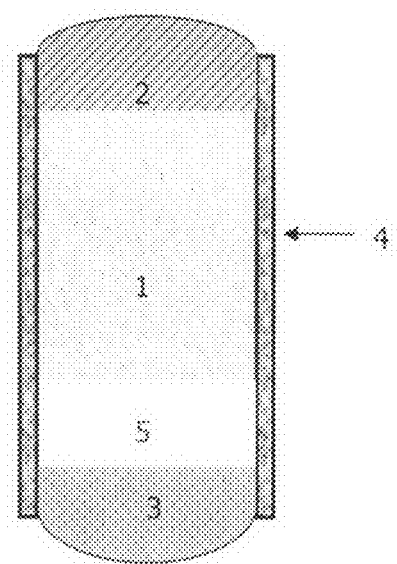

FIG. 1C shows yet another alternative embodiment, in that the slow eroding active core 1 in FIG. 1A becomes two consecutive layers—an immediate release active core layer 5, followed by a slow-eroding active core layer 1. As a result, once the enteric polymer plug 3 is dissolved, the immediate release layer 5 provides rapid drug release, which is maintained by more sustained drug release from the slow-eroding active core 1.

Figure 1D:
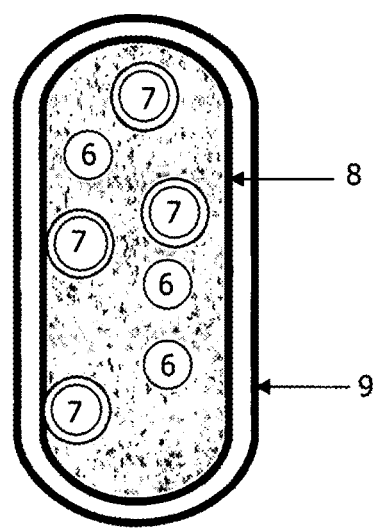

FIG. 1D shows a schematic (not necessarily to scale) drawing of another embodiment of the delivery device containing multiparticulate beads/pellets. The multiparticulate dosage form combines two types of pellets—the immediate release pellets 6 and the controlled release active pellets (XR and/or DR and/or DXR) 7—both embedded in an appropriate matrix of excipients (e.g., HPMC, MCC, glyceryl monostearate, lactose). The matrix is inside a capsule 8, which in turn is coated by enteric material 9. This type of dosage form will provide multiple pulses of drug release, with the effect being a more or less sustained blood level of drug within the target range. The release is delayed by the enteric coating 9 in order to by-pass the upper GI tract.

With this combination, the IR pellets are designed to provide an effective blood level soon after the start of the drug release, which is subsequently maintained by the DR and/or XR combinations. The DR portion provides an immediate release after a delay. If XR pellets are also used, the XR portion provides an extended release profile that maintains the effective blood level of topiramate throughout the remaining course of the day. In some embodiments, the IR pellets comprise about ⅓ of the total topiramate, while the remaining ⅔ of the topiramate is provided by the DR and/or XR.

Figure 1E:
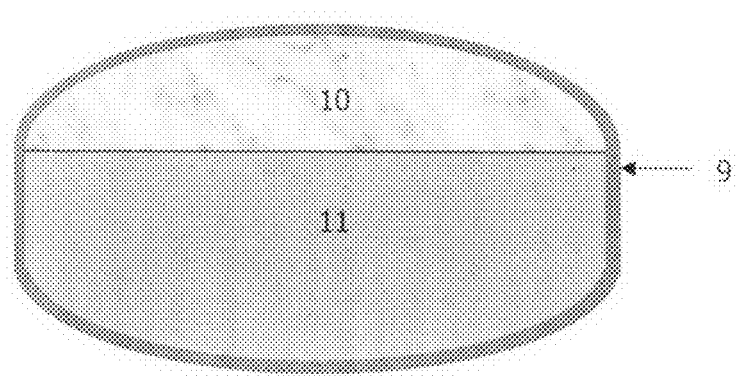

A similar effect may be achieved by a device as depicted in FIG. 1E, where an enteric coating 9 covers an inner core with two (asymmetric) portions—the immediate release active layer (IR) 10 and the controlled release active layer (DR or XR) 11. The ratio of IR to DR/XR may be anywhere between 1:10 to 2:1. In a preferred embodiment, the ratio may be 1:2.

Figure 1F:
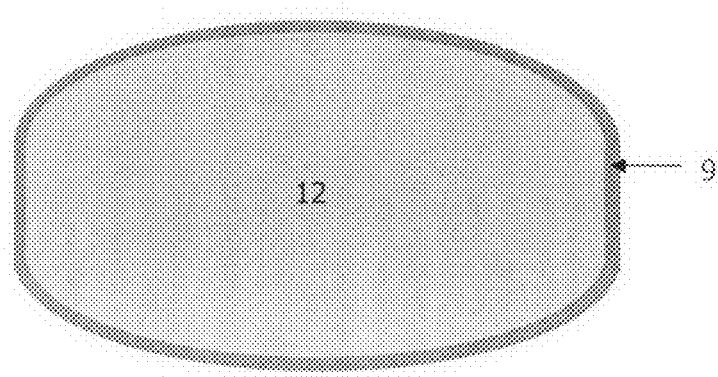

In FIG. 1F, the complex core of FIG. 1E is replaced with a uniform slow-eroding or non-eroding active matrix core 12, from which topiramate is released after the enteric coating 9 is dissolved.

Figure 1G:
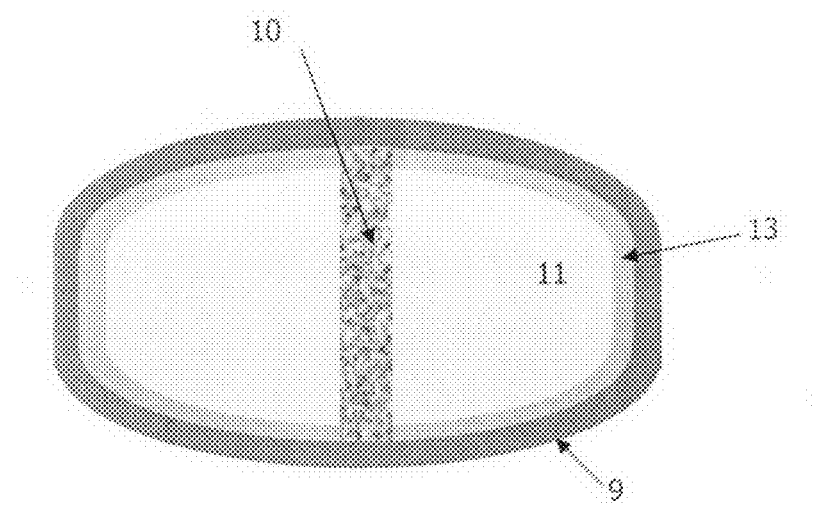

FIG. 1G presents yet another embodiment, wherein an enteric coating 9 delays the release of the drug. Upon degradation of the enteric coating 9, the immediate release active core portion 10 is quickly dissolved, effectively splitting the remaining core into two portions of controlled-release active core 11, each coated by a layer of rate-controlling coating 13 at surfaces not in contact with the immediate release active core 10. Thus the release of the drug content from the controlled-release active core 11 is only through the rate-controlling coating 13 (comparatively slow) before the immediate release active core 10 is dissolved. The rate gradually increases as the immediate release active core 10 dissolves, exposing more surface area of the two controlled-release active cores 11 not coated by the rate-controlling coating 13. The release profile may be controlled by, for example, the amount of the immediate release active core 10, the thickness and material of the rate-controlling coating 13, the geometric shape/surface area of the controlled-release active core 11 directly in contact with the immediate release active core 10, etc.

Figure 1H:
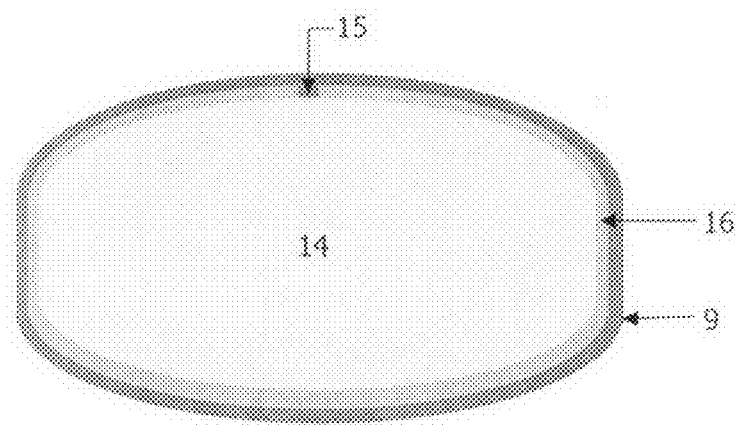

In FIG. 1H, the active core 14 is substantially covered by a layer of semi-permeable coating 16, which contains one or more small openings/orifices 15. The outermost portion of the whole device is further coated with a layer of enteric coating 9. Once coating 9 is dissolved, the orifice(s) is exposed, allowing direct release of the active core 14 through the orifice(s) 15. Different release profiles may be obtained, for example, by controlling the number and/or size of the orifice(s) 15, or the thickness and/or material of the semi-permeable coating 16.

An alternative embodiment is shown in FIG. 1I. Although the enteric coating outside the semi-permeable coating 16 is not shown, the enteric coating may be added in certain embodiments. For the depicted embodiment in FIG. 1I, the core comprises three layers, with the middle layer being the active core 14. Underneath the active core 14 is a push layer 17 that will swell after the tablet comes into contact with body fluid as fluid enters the tablet through the semi-permeable coating 16. Above the active core is a time-delay layer 18, which has access to one or more orifice(s) 15 for drug release. The swelling push layer 17 will cause first the time-delay layer 18 and then the active core 14 to be released through the orifice 15. The time-delay layer may also contain an IR component or an IR layer in between the time-delay and active core layer.

Figure 1J:
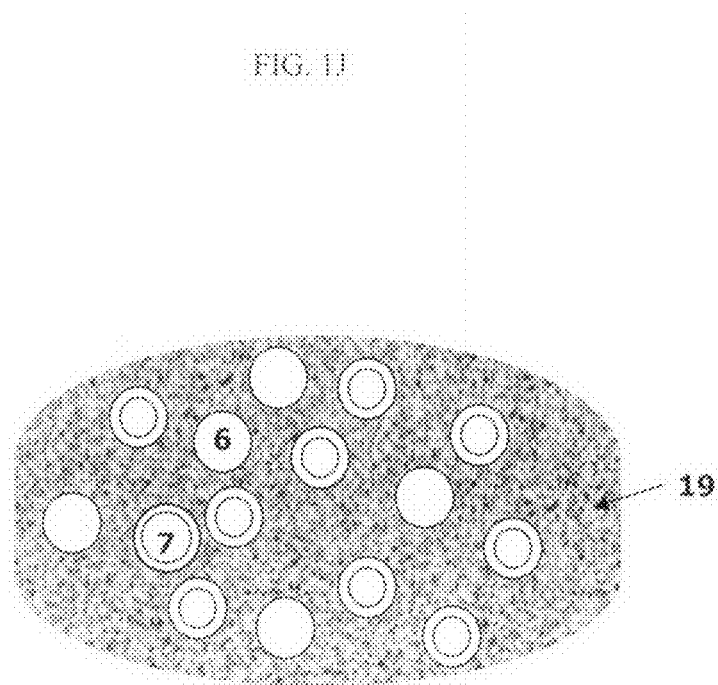

In yet another embodiment shown in FIG. 1J, the immediate release beads/pellets 6 and the controlled-release (XR and/or DR and/or DXR) beads/pellets 7 are embedded within the enteric polymer matrix 19 as multiparticulate beads/pellets. The enteric polymer matrix 19 may additionally comprise compression enhancers or fillers, or any other materials described herein that are customarily used in tablet production.

Alternatively, the IR portion of the dosage form is formulated as a matrix for embedding one or more other portions of the same dosage form (DR, XR, DXR, etc.). The IR may be coated by enteric layer to avoid release in upper GI tract. Each controlled release portion (DR, XR, DXR, etc.) is optionally coated by a bioadhesive coat and/or a delayed release coat. Each CR portion may be formed as microparticles (e.g., beads) suspended in the first portion (e.g., IR portion) matrix. The disintegration of the matrix leads to the release of the embedded microparticles, which may re-adhere to the gut or other tissues (if coated by bioadhesive layer), and provided for sustained release.

Figure 1K:
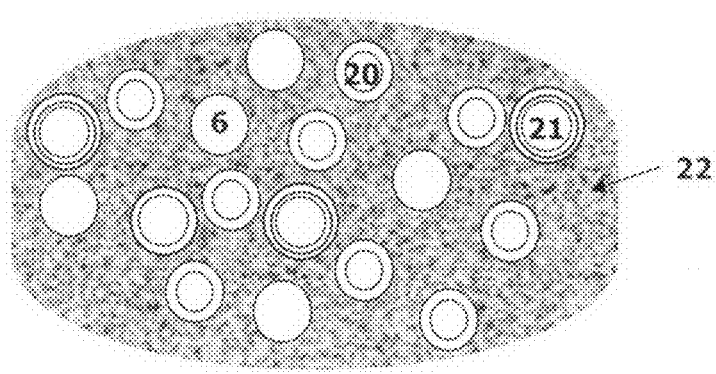

FIG. 1K features an embodiment of the delivery device which is similar to the device featured in FIG. 1J but additionally contains beads coated with a bioadhesive polymer. Some of the beads 21 are coated with release rate controlling polymer, followed by bioadhesive polymer coating, and finally an enteric polymer or delayed release polymer coating.

Figure 1L:
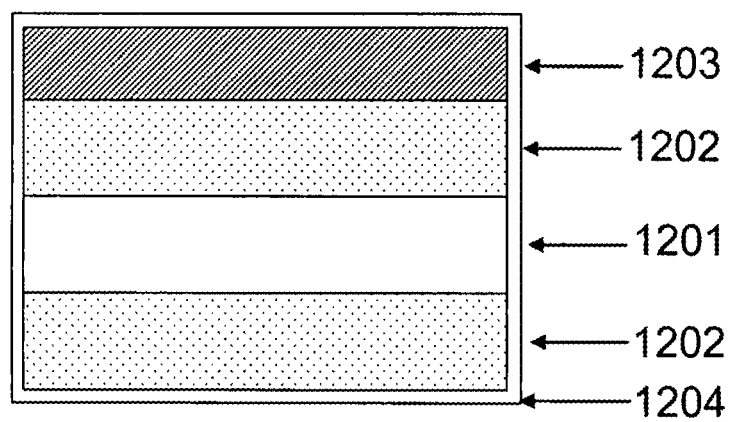

FIG. 1L features a configuration of the delivery device in which a drug portion 1201 is sandwiched between two adhesive layers 1202 (e.g., a layered cross section) or inside one continuous adhesive layer 1202 (e.g., configured as a filled tube). SPHEROMER™ I [p(FASA)] and SPHEROMER™ III (L-DOPA grafted onto butadiene maleic anhydride) layers are exemplary bioadhesive layers. The portion/layer can (but need not) be substantially flat. In certain embodiments, there are two substantially flat adhesive layers 1202 sandwiching one drug layer 1201. Components of the drug can be either released from surfaces not in contact with the adhesive parts 1202, and/or through the adhesive materials if such materials are at least partially permeable.

In certain embodiments, an immediate release portion IR 1203 may be present, and is coated over all or a part of the adhesive layer 1202. In certain embodiments, the rapid dissolution of the IR portion exposes a drug surface not in contact with the adhesive material. In another embodiment, the dissolution of the IR portion does not substantially change the release rate of the drug portion. This multilayer configuration is finally applied with an enteric or delayed release coating 1204. In certain embodiments, the delivery device is coated with an enteric polymer layer 1204, which dissolves at and above pH 4.5.

In certain embodiments, pellets produced using the methods of the invention may be dispersed in a matrix material to assist the delivery of the effective ingredients of the pellets. There are at least two preferred configurations according to this embodiment of the invention.

Figure 1M:
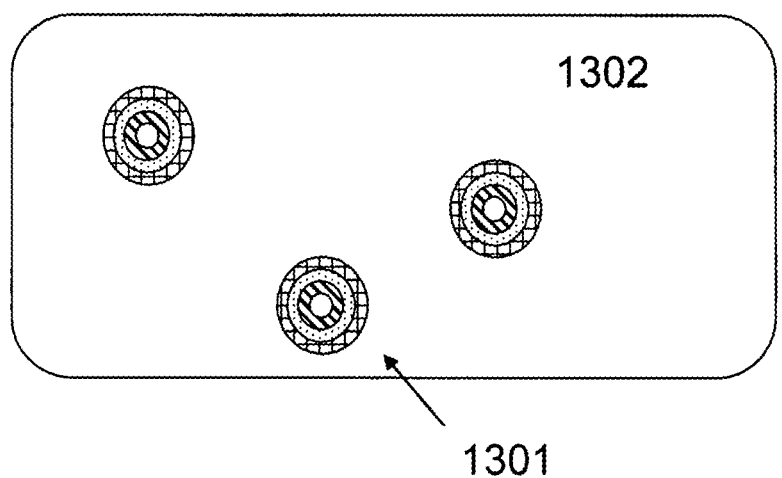

FIG. 1M shows a schematic drawing (not to scale) of one such configuration. In FIG. 1M, the active components 1301 (such as the pellets produced using the subject method, which are not necessarily round in shape) are embedded/dispersed within an inactive material or carrier matrix 1302. The carrier matrix 1302 can rapidly disintegrate, e.g., dissolve substantially completely (superdisintegrant) within about 15 minutes, 10 minutes, 8 minutes, 7 minutes, 6 minutes, 5 minutes, 3 minutes, 2 minutes, or about 1 minute or less.

The inactive material 1302 may additionally comprise one or more cushioning material(s) dispersed throughout, e.g., sufficient to protect the active components 1301 when preparing the delivery device, by substantially absorbing the impact of compacting, and/or reducing friction on the surface of the particles 1301 (to prevent damaging the substructure of the particles, see below).

The particles 1301 may be in any suitable size and shape (rods, beads, or other regular or irregular shapes). In certain embodiments, the particles are beads with a diameter of less than about 2 mm, about 1.5 mm, about 1 mm, about 0.8 mm, about 0.5 mm, about 0.3 mm, or about 0.1 mm. In certain embodiments, for pellets with topiramate as effective ingredient, the pellet size is about 0.8-1.5 mm. In other embodiments, the topiramate is micronized and the pellet size is less than 5 microns. Particles are formulated to these sizes in order to enable high drug loading when needed.

As described above, particles 1301 may have substructures, such as various coating layers surrounding a drug/ prodrug core. The core by itself may be an immediate release portion, or may have release-controlling components (e.g., CR portion), and preferably, the core is made by extrusion, such as the granulation-extrusion-spheronization process. The core is optionally surrounded by a CR coating, such as polymeric substance based on acrylates and/or methacrylates, e.g., a EUDRAGIT™ polymer (sold by Rohm America, Inc.). Specific EUDRAGIT™ polymers can be selected having various permeability and water solubility, which properties can be pH dependent or pH independent. For example, EUDRAGIT™ RL 100, EUDRAGIT™ NE, and EUDRAGIT™ RS100 are acrylic resins comprising copolymers of acrylic and methacrylic acid esters with a low content of quaternary ammonium groups, which are present as salts and give rise to the permeability of the lacquer films. EUDRAGIT™ RL100 is freely permeable and EUDRAGIT™ RS100 is slightly permeable, independent of pH. In contrast, the permeability of EUDRAGIT™ L is pH dependent. EUDRAGIT™ L is an anionic polymer synthesized from methacrylic acid and methacrylic acid methyl ester. It is insoluble in acids and pure water, but becomes increasingly soluble in a neutral to weakly alkaline solution by forming salts with alkalis. Above pH 5.0, the polymer becomes increasingly permeable. If desired, two or more types of polymeric substances may be mixed for use as the CR coating. Other polymers suitable for CR coatings, such as ethyl cellulose and cellulose acetate, can be used in the CR coating. The CR coating may comprise one or more suitable polymers, such as a combination of two or more of the polymers discussed above.

Optionally, the CR coating is itself coated by a layer of adhesive material that facilitates the adhesion of the particles/beads to a desired surface, such as a preferred GI tract surface. Various suitable adhesive materials are described herein above. For example, the pellets/beads may be coated by a top-layer of a bioadhesive polymer such as SPHEROMER™ I [p(FASA)], SPHEROMER™ II, SPHEROMER™ III, SPHEROMER™ IV, or mixtures thereof. In certain embodiments, the functions of a CR coating and bioadhesive coating can be combined in a single layer by using a mixture of polymers including a bioadhesive polymer and a polymer suitable for controlled release, i.e., a single layer may be both the CR layer and the bioadhesive layer of a particle.

Optionally, pellets can be further film-coated with an additional layer of a so-called "non-functional polymer" such as OPADRY™ II, EUDRAGIT™, hydroxypropylmethyl cellulose, hydroxypropyl cellulose, polyvinyl alcohol, polyvinylacetate, polyanhydride, carnauba waxes, magnesium stearate etc. This layer may serve as a dispersion-promoting coating that inhibits clumping and aggregation of the particles during dispersion. In embodiments wherein the pellets are further compressed with excipients to form tablets, this layer is preferably sufficiently strong or resilient to remain substantially intact during the compression process. This layer may also be protected by including a cushioning material among the excipients of the tablet matrix.

Optionally, an IR portion is included in the particle, such as over the dispersion-promoting coating, or between the dispersion-promoting coating and the adhesive layer, etc.

In an alternative embodiment, particles 1301 are not embedded within the inactive material 1302, but are instead disposed loose in a capsule that dissolves and releases the particles in the GI tract.

Figure 1N:
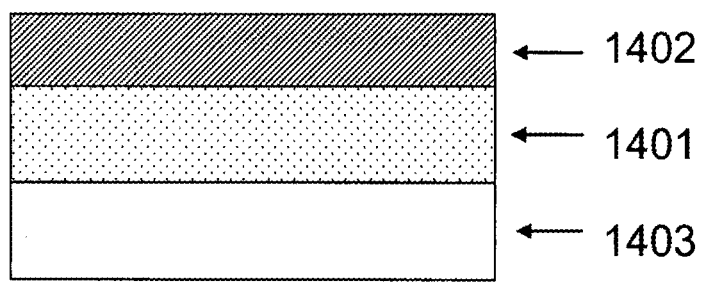

FIG. 1N features yet another embodiment of the delivery device, in which particles described herein above (e.g., with respect to FIG. 1L) are embedded within a slow eroding material 1401 (e.g., that gradually erodes over 30 minutes, 45 minutes, 1 hr, 2 hrs, 4 hrs, 6 hrs, or longer). At least a portion of the eroding material 1401 is covered by an IR portion 1402, which disintegrates relatively rapidly to expose a surface of eroding material 1401. A portion of the slow eroding material 1401 is also optionally covered by a passive polymer support layer and/or an adhesive material 1403 as described herein above. In certain embodiments, the IR portion 1402 may be disposed on the adhesive layer 1403 instead of the eroding material 1401 as depicted.

FIG. 1O features yet another embodiment of the delivery device, in which particles 1500 described herein above are disposed on the surface of a bioadhesive film 1501. The film may optionally be dried or cured, e.g., without disrupting the particle adhesion. The film may then be folded and placed in a capsule 1502 for administration to a patient. If needed the capsule containing the active containing bioadhesive film is coated with delayed release coating to allow the film to adhere to the proximal part of the GI tract. If needed, the film may first be folded or cut to a suitable shape or size. Once administered to a patient, the capsule releases the film, which then rehydrates (if necessary) and adheres to a mucosal surface, allowing the particles spreaded and adhered thereto to release the active components.

Figure 1P:
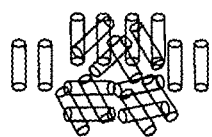

FIG. 1P features yet another embodiment of the delivery device where topiramate granules are extruded in the shape of minitablets and/or rod-like and/or thread-like structures and these structures are further coated with an enteric polymer.

Figure 1Q:
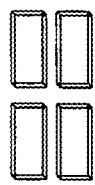

FIG. 1Q features yet another embodiment of the delivery device where topiramate granules are extruded in the shape of planar structures, such as flakes, e.g., to improve bioadhesion and bioavailability. These planar structures may be further coated with an enteric polymer.

VI. Controlled Release/Bioadhesive Layer

According to the instant invention, the subject dosage form is administered orally. In some embodiments, a portion of the topiramate is released to the lower gastrointestinal (GI) tract. Thus, it is desirable that the subject drug delivery system adhere to the lining of the appropriate viscus, such that its contents can be delivered as a function of proximity and duration of contact.

An orally ingested product can adhere to either the epithelial surface or the mucus lining of the GI tract. For the delivery of bioactive substances, it can be advantageous to have a polymeric drug delivery device adhere to the epithelium or to the mucous layer. Bioadhesion in the GI tract may proceed in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (e.g., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (e.g., van der Waals interactions) and stronger specific interactions, which include hydrogen bonds. The hydrophilic functional groups primarily responsible for forming hydrogen bonds are the hydroxyl and the carboxylic groups.

"Bioadhesion" is defined as the ability of a material to adhere to a biological tissue for an extended period of time. Bioadhesion is one solution to the problem of inadequate residence time resulting from intestinal peristalsis, and from displacement by ciliary movement. For sufficient bioadhesion to occur, an intimate contact must exist between the bioadhesive and the receptor tissue, the bioadhesive must penetrate into the crevice of the tissue surface and/or mucus, and mechanical, electrostatic, or chemical bonds must form. Polycarbophils and acrylic acid polymers usually have the best adhesive properties. Duchene et al., in *Drug Dev. Ind. Pharm.*, 14:283-318, 1988, reviewed the pharmaceutical and medical aspects of bioadhesive systems for drug delivery (incorporated herein by reference). These bioadhesive systems may be adapted for use in the instant invention. Other bioadhesive systems that may be adapted for use in the instant application are described in WO 93/21906; Smart et al., *J. Pharm. Pharmacol.* 36: 295-299, 1984; Gurney et al., *Biomaterials* 5: 336-340, 1984; Park et al., "Alternative Approaches to Oral Controlled Drug Delivery: Bioadhesives and In-Situ Systems," in J. M. Anderson and S. W. Kim, Eds., "*Recent Advances in Drug Delivery,*" Plenum Press, New York, 1984, pp. 163-183; Mikos et al., *J. Colloid Interface Sci.* 143: 366-373, 1991; and Lehr et al., *J. Controlled Rel.* 13: 51-62, 1990, all incorporated herein by reference.

In certain embodiments, the subject dosage forms have increased lower gastrointestinal retention time. For purposes of this invention, intestinal residence time is the time required for a dosage form to transit through pyloric sphincter to the intestine. For example, a dosage form of the invention has an intestinal residence time of at least 3 hours, at least 4 hours, at least 6 hours, at least 8 hours or at least 12 hours. The dosage forms of the invention may have an increased retention time in the small and/or large intestine, or in the area of the gastrointestinal tract that absorbs the drug contained in the dosage form. For example, dosage forms of the invention can be retained in the small intestine (or one or two portions thereof, selected from the duodenum, the jejunum and the ileum) for at least 6 hours, at least 8 hours or at least 12 hours, such as from 16 to 18 hours.

Certain polymers for use in the subject invention are described in more details below.

Polymers

Suitable bioadhesive polymeric coatings are disclosed in U.S. Pat. Nos. 6,197,346, 6,217,908 and 6,365,187 (the contents of which are incorporated herein by reference), and include soluble and insoluble, biodegradable and nonbiodegradable polymers. These can be hydrogels or thermoplastics, homopolymers, copolymers or blends, and/or natural or synthetic polymers. The preferred polymers are synthetic polymers, with controlled synthesis and degradation characteristics. Particularly preferred polymers are anhydride copolymers of fumaric acid and sebacic acid (P(FA:SA)), which have exceptionally good bioadhesive properties when administered to the GI tract. Examples of P(FA:SA) copolymers include those having a 1:99 to 99:1 ratio of fumaric acid to sebacic acid, such as 5:95 to 75:25, for example, 10:90 to 60:40 or at least 15:85 to 25:75. Specific examples of such copolymers have a 20:80 or a 50:50 ratio of fumaric acid to sebacic acid.

Polymers used in dosage forms of the invention preferably produce a bioadhesive interaction (fracture strength) of at least about 100 N/m$^2$ (10 mN/cm$^2$) when applied to the mucosal surface of rat intestine. The fracture strength of the dosage forms is advantageously at least about 250 N/m$^2$, at least about 500 N/m$^2$, or at least about 1000 N/m$^2$. The forces described herein refer to measurements made upon rat intestinal mucosa, unless otherwise stated. The same adhesive measurements made on a different species of animal will differ from those obtained using rats. This difference is attributed to both compositional and geometrical variations in the mucous layers of different animal species as well as cellular variations in the mucosal epithelium. However, the data shows that the same general trends prevail no matter what animal is studied (i.e., P(FA:SA) produces stronger adhesions than polylactic acid (PLA) in rats, sheep, pigs, etc.).

The fracture strength of a dosage form can be measured according to the methods disclosed by Duchene et al. Briefly, the dosage form is attached on one side to a tensile tester and is contacted with a testing surface (e.g., a mucosal membrane) on the opposite surface. The tensile tester measures the force required to displace the dosage form from the testing surface. Common tensile testers include a Texture Analyzer and the Instron tensile tester.

In the preferred method for mucoadhesive testing, dosage forms are pressed using flat-faced tooling, 0.3750" (9.525 mm) in diameter. Dosage form weight will depend on composition; in most cases, the dosage forms have a final weight of 200 mg. These dosage forms are then glued to a plastic 10 mm diameter probe using a common, fast-drying cyanoacrylate adhesive. Once the dosage forms are firmly adhered to the probe, the probe is attached to the Texture Analyzer. The Texture Analyzer is fitted with a 1 kg load cell for maximum sensitivity. The following settings are used:

| Pre-Test Speed | 0.4 mm/sec | Stop Plot At | Final Position |
|---|---|---|---|
| Test Speed | 0.1 mm/sec | Tare Mode | Auto |
| Post-Test Speed | 0.1 mm/sec | Delay Acquisition | Off |
| Applied Force | 20.0 g | Advanced Options | On |
| Return Distance | 0 mm | Proportional Gain | 0 |
| Contact Time | 420 s | Integral Gain | 0 |
| Trigger Type | Auto | Differential Gain | 0 |
| Trigger Force | 0.5 g | Max. Tracking Speed | 0 mm/sec |

The Test and Post-Test Speeds are as low as the instrument will allow, to ensure a maximum number of data points captured. The Pre-Test speed is used only until the probe encounters the Trigger Force; i.e., prior to contacting the tissue.

The Proportional, Integral, and Differential Gain are set to 0. These settings, when optimized, maintain the system at the Applied Force for the duration of the Contact Time. With soft tissue as a substrate, however, the probe and dosage form are constantly driven into the deformable surface. This results in visible damage to the tissue. Thus, the probe and dosage form are allowed to relax gradually from the Applied Force by setting these parameters to 0. The tracking speed, which is a measure of how rapidly the feedback is adjusted, is also set to 0.

The tissue on which the dosage forms are tested is secured in the Mucoadhesive Rig; the rig is then completely immersed in a 600 mL Pyrex beaker containing 375 mL of PBS. The tissue is maintained at approximately 37° C. for the duration of the test; no stirring is used as the machine can detect the oscillations from the stir bar.

In the past, two classes of polymers have shown useful bioadhesive properties, hydrophilic polymers and hydrogels. In the large class of hydrophilic polymers, those containing carboxylic groups (e.g., poly[acrylic acid]) exhibit the best bioadhesive properties. It is thus expected that polymers with the highest concentrations of carboxylic groups are preferred materials for bioadhesion on soft tissues. In other studies, the most promising polymers were sodium alginate, carboxymethylcellulose, hydroxymethylcellulose and methylcellulose. Some of these materials are water-soluble, while others are hydrogels.

Rapidly bioerodible polymers such as poly[lactide-co-glycolide], polyanhydrides, and polyorthoesters, whose carboxylic groups are exposed on the external surface as their smooth surface erodes, are suitable for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers suitable for the present invention include proteins (e.g., hydrophilic proteins), such as zein, modified zein, casein, gelatin, gluten, chitosan, serum albumin, or collagen, and polysaccharides such as cellulose, dextrans, polyhyaluronic acid, polymers of acrylic and methacrylic esters and alginic acid. These are generally less suitable for use in bioadhesive coatings due to higher levels of variability in the characteristics of the final products, as well as in degradation following administration. Synthetically modified natural polymers include alkyl celluloses, hydroxyalkyl celluloses, cellulose ethers, cellulose esters, and nitrocelluloses.

Representative synthetic polymers for use in bioadhesive coatings include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Other polymers suitable for use in the invention include, but are not limited to, methyl cellulose, hydroxypropyl cellulose, hydroxypropyl methyl cellulose, hydroxybutyl methyl cellulose, cellulose acetate phthalate, carboxymethyl cellulose, cellulose sulfate sodium salt, alginates, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, and polyvinylphenol. Representative bioerodible polymers for use in bioadhesive coatings include polylactides, polyglycolides and copolymers thereof, poly(ethylene terephthalate), poly(butyric acid), poly(valeric acid), poly(lactide-co-caprolactone), poly[lactide-co-glycolide], polyanhydrides (e.g., poly(adipic anhydride)), polyorthoesters, chitosan, chitin, hyaluronic acid, hyalurronan, Carbopols, Corplex polymers, Polycarbophils-Cysteine (Thiomers), Chitosan-Thioglycolic acid copolymers, poly(methacrylic acid-grafted-ethylene glycol), poly(methyl vinyl ether-co-malic anhydride), cholestyramine (Duolite AP-143), sucralfate and gliadin, blends and copolymers thereof.

Polyanhydrides are particularly suitable for use in bioadhesive delivery systems because, as hydrolysis proceeds, causing surface erosion, more and more carboxylic groups are exposed to the external surface. However, polylactides erode more slowly by bulk erosion, which is advantageous in applications where it is desirable to retain the bioadhesive coating for longer durations. In designing bioadhesive polymeric systems based on polylactides, polymers that have high concentrations of carboxylic acid are preferred. The high concentrations of carboxylic acids can be attained by using low molecular weight polymers (MW of 2000 or less), because low molecular weight polymers contain a high concentration of carboxylic acids at the end groups.

The polymers listed above can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif., or can alternatively be synthesized from monomers obtained from these suppliers using standard techniques.

When the bioadhesive polymeric coating is a synthetic polymer coating, the synthetic polymer is typically selected from polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly(butyric acid), poly(valeric acid), poly(lactide-co-glycolide), polyanhydrides, polyorthoesters, poly(fumaric acid), poly(maleic acid), and blends and copolymers of thereof. Preferably, the synthetic polymer is poly(fumaric-co-sebacic) anhydride.

Another group of polymers suitable for use as bioadhesive polymeric coatings are polymers that have a hydrophobic backbone with at least one hydrophobic group pendant from the backbone. Suitable hydrophobic groups are groups that are generally non-polar. Examples of such hydrophobic groups include alkyl, alkenyl and alkynyl groups. Preferably, the hydrophobic groups are selected to not interfere and instead to enhance the bioadhesiveness of the polymers.

A further group of polymers suitable for use as bioadhesive polymeric coatings are polymers having a hydrophobic backbone with at least one hydrophilic group pendant from the backbone. Suitable hydrophilic groups are groups that are capable of hydrogen bonding to another functional group. Example of such hydrophilic groups include negatively charged groups such as carboxylic acids, sulfonic acids and phosphonic acids, positively charged groups such as (protonated) amines and neutral, polar groups such as amides and imines. Preferably, the hydrophilic groups are selected to not interfere and instead to enhance the bioadhesiveness of the polymers. The hydrophilic groups can be either directly attached to a hydrophobic polymer backbone or attached through a spacer group. Typically, a spacer group is an alkylene group, particularly a $C_1$-$C_8$ alkyl group such as a $C_2$-$C_6$ alkyl group. Preferred compounds containing one or more hydrophilic groups include amino acids (e.g., phenylalanine, tyrosine and derivatives thereof) and amine-containing carbohydrates (sugars) such as glucosamine.

Polymers can be modified by increasing the number of carboxylic groups accessible during biodegradation, or on the polymer surface. The polymers can also be modified by binding amino groups to the polymer. The polymers can be modified using any of a number of different coupling chemistries available in the art to covalently attach ligand molecules with bioadhesive properties to the surface-exposed molecules of the polymeric microspheres.

The attachment of any positively charged ligand, such as polyethyleneimine or polylysine, to a polymer may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most polymers with the appropriate chemistry, such as with carbodiimidazole (CDI), and be expected to influence the binding to the gut. For example, polyclonal antibodies raised against components of mucin or else intact mucin, when covalently coupled to a polymer, would provide for increased bioadhesion. Similarly, antibodies directed against specific cell surface receptors exposed on the lumenal surface of the intestinal tract would increase the residence time when coupled to polymers using the appropriate chemistry. The ligand affinity need not be based only on electrostatic charge, but other useful physical parameters such as solubility in mucin or specific affinity to carbohydrate groups.

The covalent attachment of any of the natural components of mucin in either pure or partially purified form to the polymers would increase the solubility of the polymer in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetyl-neuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, such as polyaspartic acid and polyglutamic acid, may also increase bioadhesiveness. The polyamino chains would increase bioadhesion by means of chain entanglement in mucin strands as well as by increased carboxylic charge.

Polymer-Metal Complexes

As disclosed in U.S. Pat. Nos. 5,985,312, 6,123,965 and 6,368,586, the contents of which are incorporated herein by reference, polymers, such as those described above, having a metal compound incorporated therein have a further improved ability to adhere to tissue surfaces, such as mucosal membranes. The metal compound incorporated into the polymer can be, for example, a water-insoluble metal oxide. The incorporation of metal compounds into a wide range of different polymers, even those that are not normally bioadhesive, improves their ability to adhere to tissue surfaces such as mucosal membranes.

Metal compounds which can be incorporated into polymers to improve their bioadhesive properties preferably are water-insoluble metal compounds, such as water-insoluble metal oxides and metal hydroxides, which are capable of becoming incorporated into and associated with a polymer to thereby improve the bioadhesiveness of the polymer. As defined herein, a water-insoluble metal compound is defined as a metal compound with little or no solubility in water, for example, less than about 0.0 to 0.9 mg/mL.

The water-insoluble metal compounds can be derived from a wide variety of metals, including, but not limited to, calcium, iron, copper, zinc, cadmium, zirconium and titanium. The water insoluble metal compound preferably is a metal oxide or hydroxide. Water insoluble metal compounds of multivalent metals are preferred. Representative metal oxides suitable for use in the compositions described herein include cobalt (I) oxide (CoO), cobalt (II) oxide ($Co_2O_3$), selenium oxide ($SeO_2$), chromium (IV) oxide ($CrO_2$), manganese oxide ($MnO_2$), titanium oxide ($TiO_2$), lanthanum oxide ($La_2O_3$), zirconium oxide ($ZrO_2$), silicon oxide ($SiO_2$), scandium oxide ($Sc_2O_3$), beryllium oxide (BeO), tantalum oxide ($Ta_2O_5$), cerium oxide ($CeO_2$), neodymium oxide ($Nd_2O_3$), vanadium oxide ($V_2O_5$), molybdenum oxide ($Mo_2O_3$), tungsten oxide (WO), tungsten trioxide ($WO_3$), samarium oxide ($Sm_2O_3$), europium oxide ($Eu_2O_3$), gadolinium oxide ($Gd_2O_3$), terbium oxide ($Tb_4O_7$), dysprosium oxide ($Dy_2O_3$), holmium oxide ($Ho_2O_3$), erbium oxide ($Er_2O_3$), thulium oxide ($Tm_2O_3$), ytterbium oxide ($Yb_2O_3$), lutetium oxide ($Lu_2O_3$), aluminum oxide ($Al_2O_3$), indium oxide ($InO_3$), germanium oxide ($GeO_2$), antimony oxide ($Sb_2O_3$), tellurium oxide ($TeO_2$), nickel oxide (NiO), and zinc oxide (ZnO). Other oxides include barium oxide (BaO), calcium oxide (CaO), nickel oxide (III) ($Ni_2O_3$), magnesium oxide (MgO), iron (II) oxide (FeO), iron (III) oxide ($Fe_2O_3$), copper oxide (II) (CuO), cadmium oxide (CdO), and zirconium oxide ($ZrO_2$).

Preferred properties defining the metal compound include: (a) substantial insolubility in aqueous environments, such as acidic or basic aqueous environments (such as those present in the gastric lumen); and (b) ionizable surface charge at the pH of the aqueous environment.

The water-insoluble metal compounds can be incorporated into the polymer by one of the following mechanisms: (a) physical mixtures which result in entrapment of the metal compound; (b) ionic interaction between metal compound and polymer; (c) surface modification of the polymers which would result in exposed metal compound on the surface; and (d) coating techniques such as fluidized bed, pan coating, or any similar methods known to those skilled in the art, which produce a metal compound enriched layer on the surface of the device. In certain embodiments, nanoparticles or microparticles of the water-insoluble metal compound are incorporated into the polymer.

In certain embodiments, the metal compound is provided as a fine particulate dispersion of a water-insoluble metal oxide which is incorporated throughout the polymer or at least on the surface of the polymer which is to be adhered to a tissue surface. The metal compound also can be incorporated in an inner layer of the polymer and exposed only after degradation or else dissolution of a "protective" outer layer. For example, a tablet core containing a polymer and metal may be covered with an enteric coating designed to dissolve when exposed to intestinal fluid. The metal compound-enriched core then is exposed and become available for binding to GI mucosa.

Fine metal oxide particles can be produced for example by micronizing a metal oxide by mortar and pestle treatment to produce particles ranging in size, for example, from 10.0 to 300 nm. The metal oxide particles can be incorporated into the polymer, for example, by dissolving or dispersing the particles into a solution or dispersion of the polymer.

Advantageously, metal compounds which are incorporated into polymers to improve their bioadhesive properties can be metal compounds which are already approved by the FDA as either food or pharmaceutical additives, such as zinc oxide.

Suitable polymers which can be used and into which the metal compounds can be incorporated include soluble and water-insoluble, and biodegradable and nonbiodegradable polymers, including hydrogels, thermoplastics, and homopolymers, copolymers and blends of natural and synthetic polymers, provided that they have the requisite fracture strength when mixed with a metal compound. In additional to those listed above, representative polymers which can be used in conjunction with a metal compound include hydrophilic polymers, such as those containing carboxylic groups, including polyacrylic acid. Bioerodible polymers including polyanhydrides, poly(hydroxy acids) and polyesters, as well as blends and copolymers thereof also can be used. Representative bioerodible poly(hydroxy acids) and copolymers thereof which can be used include poly(lactic acid), poly(glycolic acid), poly(hydroxy-butyric acid), poly (hydroxyvaleric acid), poly(caprolactone), poly(lactide-co-caprolactone), and poly(lactide-co-glycolide). Polymers containing labile bonds, such as polyanhydrides and polyorthoesters, can be used optionally in a modified form with reduced hydrolytic reactivity. Positively charged hydrogels, such as chitosan, and thermoplastic polymers, such as polystyrene also can be used.

Representative natural polymers which also can be used include proteins, such as zein, modified zein, casein, gelatin, gluten, serum albumin, or collagen, and polysaccharides such as dextrans, polyhyaluronic acid and alginic acid. Representative synthetic polymers include polyphosphazenes, polyamides, polycarbonates, polyacrylamides, polysiloxanes, polyurethanes and copolymers thereof. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt.

Polymers of acrylic and methacrylic acids or esters and copolymers thereof can be used. Representative polymers which can be used include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other polymers which can be used include polyalkylenes such as polyethylene and polypropylene; polyarylalkylenes such as polystyrene; poly(alkylene glycols), such as poly(ethylene glycol); poly(alkylene oxides), such as poly(ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly(vinyl acetate), polyvinyl phenol and polyvinylpyrrolidone.

Water soluble polymers can also be used. Representative examples of suitable water soluble polymers include polyvinyl alcohol, polyvinylpyrrolidone, methyl cellulose, hydroxypropyl cellulose, hydroxypropylmethyl cellulose and polyethylene glycol, copolymers of acrylic and methacrylic acid esters, and mixtures thereof. Water insoluble polymers also can be used. Representative examples of suitable water insoluble polymers include ethylcellulose, cellulose acetate, cellulose propionate (lower, medium or -higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride), polyurethanes, and mixtures thereof. In certain embodiments, a water insoluble polymer and a water soluble polymer are used together, such as in a mixture. Such mixtures are useful in controlled drug release formulations, wherein the release rate can be controlled by varying the ratio of water soluble polymer to water insoluble polymer.

Polymers varying in viscosity as a function of temperature or shear or other physical forces also may be used. Poly(oxyalkylene) polymers and copolymers such as poly(ethylene oxide)-poly(propylene oxide) (PEO-PPO) or poly(ethylene oxide)-poly(butylene oxide) (PEO-PBO) copolymers, and copolymers and blends of these polymers with polymers such as poly(alpha-hydroxy acids), including but not limited to lactic, glycolic and hydroxybutylc acids, polycaprolactones, and polyvalerolactones, can be synthesized or commercially obtained. For example, polyoxyalkylene copolymers are described in U.S. Pat. Nos. 3,829,506, 3,535,307, 3,036,118, 2,979,578, 2,677,700 and 2,675,619. Polyoxyalkylene copolymers are sold, for example, by BASF under the trade name PLURONICS™. These materials are applied as viscous solutions at room temperature or lower which solidify at the higher body temperature. Other materials with this behavior are known in the art, and can be utilized as described herein. These include KLUCEL™ (hydroxypropyl cellulose), and purified konjac glucomannan gum.

Other suitable polymers are polymeric lacquer substances based on acrylates and/or methacrylates, commonly called EUDRAGIT™ polymers (sold by Rohm America, Inc.). Specific EUDRAGIT™ polymers can be selected having various permeability and water solubility, which properties can be pH dependent or pH independent. For example, EUDRAGIT™ RL100 and EUDRAGIT™ RS100 are acrylic resins comprising copolymers of acrylic and methacrylic acid esters with a low content of quaternary ammonium groups, which are present as salts and give rise to the permeability of the lacquer films, whereas EUDRAGIT™ RL100 is freely permeable and EUDRAGIT™ RS 100 is slightly permeable, independent of pH. In contrast, the permeability of EUDRAGIT™ L is pH dependent. EUDRAGIT™ L is an anionic polymer synthesized from methacrylic acid and methacrylic acid methyl ester. It is insoluble in acids and pure water, but becomes increasingly soluble in a neutral to weakly alkaline solution by forming salts with alkalis. Above pH 5.0, the polymer becomes increasingly permeable.

Polymer solutions that are liquid at an elevated temperature but solid or gelled at body temperature can also be utilized. A variety of thermoreversible polymers are known, including natural gel-forming materials such as agarose, agar, furcellaran, beta-carrageenan, beta-1,3-glucans such as curdlan, gelatin, or polyoxyalkylene containing compounds, as described above. Specific examples include thermosetting biodegradable polymers for in vivo use described in U.S. Pat. No. 4,938,763, the contents of which are incorporated herein by reference.

Polymer Blends with Monomers and/or Oligomers

Polymers with enhanced bioadhesive properties are provided by incorporating anhydride monomers or oligomers into one of the polymers listed above by dissolving, dispersing, or blending, as taught by U.S. Pat. Nos. 5,955,096 and 6,156,348, the contents of which are incorporated herein by reference. The polymers may be used to form drug delivery systems which have improved ability to adhere to tissue surfaces, such as mucosal membranes. The anhydride oligomers are formed from organic diacid monomers, preferably the diacids normally found in the Krebs glycolysis cycle. Anhydride oligomers which enhance the bioadhesive properties of a polymer have a molecular weight of about 5000 or less, typically between about 100 and 5000 Daltons, or include 20 or fewer diacid units linked by anhydride linkages and terminating in an anhydride linkage with a carboxylic acid monomer.

The oligomer excipients can be blended or incorporated into a wide range of hydrophilic and hydrophobic polymers including proteins, polysaccharides and synthetic biocompatible polymers, including those described above. In certain embodiments, anhydride oligomers may be combined with metal oxide particles, such as those described above, to improve bioadhesion even more than with the organic additives alone. Organic dyes, because of their electronic charge and hydrophobicity or hydrophilicity, can either increase or decrease the bioadhesive properties of polymers when incorporated into the polymers.

As used herein, the term "anhydride oligomer" refers to a diacid or polydiacid linked by anhydride bonds, and having carboxy end groups linked to a monoacid such as acetic acid by anhydride bonds. The anhydride oligomers have a molecular weight less than about 5000, typically between about 100 and 5000 Daltons, or are defined as including between one to about 20 diacid units linked by anhydride bonds. In certain embodiments, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example, from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile. As analyzed by gel permeation chromatography, the molecular weight may be, for example, on the order of 200-400 for fumaric acid oligomer (FAPP) and 2000-4000 for sebacic acid oligomer (SAPP). The anhydride bonds can be detected by Fourier transform infrared spectroscopy by the characteristic double peak at 1750 cm$^{-1}$ and 1820 cm$^{-1}$, with a corresponding disappearance of the carboxylic acid peak normally at 1700 cm$^{-1}$.

In certain embodiments, the oligomers may be made from diacids described for example in U.S. Pat. Nos. 4,757,128, 4,997,904 and 5,175,235, the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic dyes, because of their electronic charge and hydrophilicity or hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2, 3, 13 and 86, rose bengal, safranin, Sudan III and IV, Sudan black B and toluidine blue.

Polymers Functionalized with Hydroxy-Substituted Aromatic Groups

Polymers having an aromatic group which contains one or more hydroxyl groups grafted onto them or coupled to individual monomers are also suitable for use in the bioadhesive coatings of the invention. Such polymers can be biodegradable or non-biodegradable polymers. The polymer can be hydrophobic. Preferably, the aromatic group is catechol or a derivative thereof and the polymer contains reactive functional groups. Typically, the polymer is a polyanhydride and the aromatic compound is the catechol derivative DOPA. These materials display bioadhesive properties superior to conventional bioadhesives used in therapeutic and diagnostic applications.

The molecular weight of the suitable polymers and percent substitution of the polymer with the aromatic group may vary greatly. The degree of substitution varies based on the desired adhesive strength, it may be as low as 10%, 25% or 50%, or up to 100% substitution. Generally, at least 50% of the monomers in the polymeric backbone are substituted with at least one aromatic group. Preferably, about 100% of the monomers in the polymeric backbone are substituted with at least one aromatic group. The resulting polymer has a molecular weight ranging from about 1 to 2,000 kDa.

The polymer that forms that backbone of the bioadhesive material can be a biodegradable polymer. Examples of preferred biodegradable polymers include synthetic polymers such as poly hydroxy acids, such as polymers of lactic acid and glycolic acid, polyanhydrides, poly(ortho)esters, polyesters, polyurethanes, poly(butyric acid), poly(valeric acid), poly(caprolactone), poly(hydroxybutyrate), poly(lactide-co-glycolide) and poly(lactide-cocaprolactone), and natural polymers such as alginate and other polysaccharides, collagen and chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo and by surface or bulk erosion. The foregoing materials may be used alone, as physical mixtures (blends), or as co-polymers.

Suitable polymers can formed by first coupling the aromatic compound to the monomer and then polymerizing. In this example, the monomers may be polymerized to form a polymer backbone, including biodegradable and non-biodegradable polymers. Suitable polymer backbones include, but are not limited to, polyanhydrides, polyamides, polycarbonates, polyalkylenes, polyalkylene oxides such as polyethylene glycol, polyalkylene terephthalates such as poly(ethylene terephthalate), polyvinyl alcohols, polyvinyl ethers, polyvinyl esters, polyethylene, polypropylene, poly(vinyl acetate), poly(vinyl chloride), polystyrene, polyvinyl halides, polyvinylpyrrolidone, polyhydroxy acids, polysiloxanes, polyurethanes and copolymers thereof, alkyl cellulose, hydroxyalkyl celluloses, cellulose ethers, cellulose esters, nitrocellulloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly (isodecylmethacrylate), poly(lauryl methacrylate), poly (phenyl methacrylate), poly(methyl acrylate), poly(isopropyl acrylate), poly(isobutyl acrylate), poly(octadccyl acrylate).

A suitable polymer backbone can be a known bioadhesive polymer that is hydrophilic or hydrophobic. Hydrophilic polymers include CARBOPOL™, polycarbophil, cellulose esters, and dextran.

Non-biodegradable polymers, especially hydrophobic polymers are also suitable as polymer backbones. Examples of preferred non-biodegradable polymers include ethylene vinyl acetate, poly(methacrylic acid), copolymers of maleic anhydride with other unsaturated polymerizable monomers, poly(butadiene maleic anhydride), polyamides, copolymers and mixtures thereof and dextran, cellulose and derivatives thereof.

Hydrophobic polymer backbones include polyanhydrides, poly(ortho) esters, and polyesters such as polycaprolactone. Preferably, the polymer is sufficiently hydrophobic that it is not readily water soluble, for example the polymer should be soluble up to less than about 1% w/w in water, preferably about 0.1% w/w in water at room temperature or body temperature. In the most preferred embodiment, the polymer is a polyanhydride, such as a poly(butadiene maleic anhydride) or another copolymer of maleic anhydride. Polyanhydrides may be formed from dicarboxylic acids as described in U.S. Pat. No. 4,757,128 to Domb et al., incorporated herein by reference. Suitable diacids include aliphatic dicarboxylic acids, aromatic dicarboxylic acids, aromatic-aliphatic dicarboxylic acid, combinations of aromatic, aliphatic and aromatic-aliphatic dicarboxylic acids, aromatic and aliphatic heterocyclic dicarboxylic acids, and aromatic and aliphatic heterocyclic dicarboxylic acids in combination with aliphatic dicarboxylic acids, aromatic-aliphatic dicarboxylic acids, and aromatic dicarboxylic acids of more than one phenyl group. Suitable monomers include sebacic acid (SA), fumaric acid (FA), bis(p-carboxyphenoxy) propane (UP), isophthalic acid (IPh), and dodecanedioic acid (DD).

A wide range of molecular weights are suitable for the polymer that forms the backbone of the bioadhesive material. The molecular weight may be as low as about 200 Da (for oligomers) up to about 2,000 kDa. Preferably the polymer has a molecular weight of at least 1,000 Da, more preferably at least 2,000 Da, most preferably the polymer has a molecular weight of up to 20 kDa or up to 200 kDa. The molecular weight of the polymer may be up to 2,000 kDa.

The range of substitution on the polymer varies greatly and depends on the polymer used and the desired bioadhesive strength. For example, a butadiene maleic anhydride copolymer that is 100% substituted with DOPA will have the same number of DOPA molecules per chain length as a 67% substituted ethylene maleic anhydride copolymer. Typically, the polymer has a percentage substitution ranging from 10% to 100%, preferably ranging from 50% to 100%.

The polymers and copolymers that form the backbone of the bioadhesive material include reactive functional groups that interact with the functional groups on the aromatic compound.

It is desirable that the polymer or monomer that forms the polymeric backbone contains accessible functional groups that easily react with molecules contained in the aromatic compounds, such as amines and thiols. In a preferred embodiment, the polymer contains amino reactive moieties, such as aldehydes, ketones, carboxylic acid derivatives, cyclic anhydrides, alkyl halides, aryl azides, isocyanates, isothiocyanates, succinimidyl esters or a combination thereof.

Preferably, the aromatic compound containing one or more hydroxyl groups is catechol or a derivative thereof. Optionally, the aromatic compound is a polyhydroxy aromatic compound, such as a trihydroxy aromatic compound (e.g., phloroglucinol) or a multihydroxy aromatic compound (e.g., tannin). The catechol derivative may contain a reactive group, such as an amino, thiol, or halide group. The preferred catechol derivative is 3,4-dihydroxyphenylalanine (DOPA), which contains a primary amine. Tyrosine, the immediate precursor of DOPA, which differs only by the absence of one hydroxyl group in the aromatic ring, can also be used. Tyrosine is capable of conversion (e.g., by hydroxylation) to the DOPA form. A particularly preferred aromatic compound is an amine-containing aromatic compound, such as an amine-containing catechol derivative (e.g., dopamine).

Two general methods are used to form the polymer product. In one example, a compound containing an aromatic group which contains one or more hydroxyl groups is grafted onto a polymer. In this example, the polymeric backbone is a biodegradable polymer. In a second example, the aromatic compound is coupled to individual monomers and then polymerized.

Any chemistry which allows for the conjugation of a polymer or monomer to an aromatic compound containing one or more hydroxyl groups can be used, for example, if the aromatic compound contains an amino group and the monomer or polymer contains an amino reactive group, this modification to the polymer or monomer is performed through a nucleophilic addition or a nucleophilic substitution reaction, such as a Michael-type addition reaction, between the amino group in the aromatic compound and the polymer or monomer. Additionally, other procedures can be used in the coupling reaction. For example, carbodiimide and mixed anhydride based procedures form stable amide bonds between carboxylic acids or phosphates and amino groups, bifunctional aldehydes react with primary amino groups, bifunctional active esters react with primary amino groups, and divinylsulfone facilitates reactions with amino, thiol, or hydroxy groups.

The aromatic compounds are grafted onto the polymer using standard techniques to form the bioadhesive material. In one example, L-DOPA is grafted to maleic anhydride copolymers by reacting the free amine in L-DOPA with the maleic anhydride bond in the copolymer.

A variety of different polymers can be used as the backbone of the bioadhesive material, as described above. Additional representative polymers include 1:1 random copolymers of maleic anhydride with ethylene, vinyl acetate, styrene, or butadiene. In addition, a number of other compounds containing aromatic rings with hydroxy substituents, such as tyrosine or derivatives of catechol, can be used in this reaction.

In another embodiment, the polymers are prepared by conjugate addition of a compound containing an aromatic group that is attached to an amine to one or more monomers containing an amino reactive group. In a preferred method, the monomer is an acrylate or the polymer is acrylate. For example, the monomer can be a diacrylate such as 1,4-butanediol diacrylate, 1,3-propanediol diacrylate, 1,2-ethanediol diacrylate, 1,6-hexanediol diacrylate, 2,5-hexanediol diacrylate or 1,3-propanediol diacrylate. In an example of the coupling reaction, the monomer and the compound containing an aromatic group are each dissolved in an organic solvent (e.g., THF, $CH_2Cl_2$, methanol, ethanol, CHCl$_3$, hexanes, toluene, benzene, CCl$_4$, glyme, diethyl ether, etc.) to form two solutions. The resulting solutions are combined, and the reaction mixture is heated to yield the desired polymer. The molecular weight of the synthesized polymer can be controlled by the reaction conditions (e.g., temperature, starting materials, concentration, solvent, etc.) used in the synthesis.

For example, a monomer, such as 1,4-phenylene diacrylate or 1,4-butanediol diacrylate having a concentration of 1.6 M, and DOPA or another primary amine containing aromatic molecule are each dissolved in an aprotic solvent such as DMF or DMSO to form two solutions. The solutions are mixed to obtain a 1:1 molar ratio between the diacrylate and the amine group and heated to 56° C. to form a bioadhesive material.

Bioadhesive Polymer Blends

Hydrophobic polymers, such as polyesters, poly(anhydrides), ethyl cellulose, even if possibly non-adhesive on their own, may nevertheless be made bioadhesive simply by physically mixing the hydrophobic polymers with one or more suitable compounds (such as catechols or derivatives L-DOPA, D-DOPA, dopamine, or carbidopa, etc.) to create "bioadhesive compositions." Similarly, metal oxides may also be used for this purpose.

The molecular weight of the bioadhesive polymers and percent substitution of the polymers with residues of the compounds disclosed may vary greatly. The degree of substitution varies based on the desired adhesive strength, it may be as low as 10%, 20%, 25%, 50%, or up to 100% substitution. On average, at least 50% of the repeat units in the polymeric backbone are substituted with at least one residue. In one particular embodiment, 75-95% of the residues in the backbone are substituted with at least one residue. In another particular embodiment, on average 100% of the repeat units in the polymeric backbone are substituted with at least one residue. The resulting bioadhesive polymer typically has a molecular weight ranging from about 1 to 2,000 kDa, such as 1 to 1,000 kDa, 10 to 1,000 kDa or 100 to 1,000 kDa. Polymers used in bioadhesive compositions typically have the same range of molecular weights.

Unlike the bioadhesive polymers described above, there is typically no covalent bond formed between the compounds and the polymer in the bioadhesive compositions (i.e., the polymer does not chemically react with the compound, although hydrogen bonds, ionic bonds and/or van der Waals interactions can occur).

Suitable polymers for use in bioadhesive compositions are described above. Typically, the polymer itself may not be bioadhesive, but the polymer can be bioadhesive (e.g., a polymer with hydrogen bond-forming pendant groups). Preferably, the polymer is a hydrophobic polymer such as a poly(lactone), e.g., poly(caprolactone).

To form the bioadhesive compositions of the invention, typically a polymer and a suitable compound are dissolved in a compatible solvent and mixed together. The solvent is then evaporated, preferably at a controlled temperature and rate of removal. Alternatively or in combination with general evaporation, the bioadhesive composition can be spray dried or dried at room temperature.

In another example, a mixture of a polymer and a suitable compound are melted at or slightly above the melting point of the polymer, typically while being mixed. Both the polymer and the suitable compound should be selected such that they are chemically stable (e.g., do not decompose, do not become oxidized) at the melting point temperature. After the composition has re-solidified, it can be milled in order to obtain particles of the desired size.

The subject bioadhesive compositions can also be prepared by dry mixing of a polymer and a suitable compound, provided that the suitable compound is sufficiently distributed throughout the composition.

In each of the above methods, additional components can be added to the mixture prior to dissolution, melting and/or mixing. The additional components are preferably stable under the conditions the mixture is exposed to. In particular, active agents should be stable at the melting point temperature if that method is employed.

The weight ratio of polymer to the suitable compound in a bioadhesive composition can be selected to give the desired amount of bioadhesion. Typically, the weight ratio of polymer to compound is 9:1 to 1:9, such as 3:1 to 1:3 or 2:1 to 1:2. For example, when the polymer is predominant component, the weight ratio is 9:1 to 1:1, 3:1 to 1:1 or 2:1 to 1:1.

Coatings

Preferred bioadhesive coatings do not appreciably swell upon hydration, such that they do not substantially inhibit or block movement (e.g., of ingested food) through the gastrointestinal tract, as compared to the polymers disclosed by Duchene et al. Generally, polymers that do not appreciably swell upon hydration include one or more hydrophobic regions, such as a polymethylene region (e.g., $(CH_2)_n$, where n is 4 or greater). The swelling of a polymer can be assessed by measuring the change in volume when the polymer is exposed to an aqueous solution. Polymers that do not appreciably swell upon hydration expand in volume by 50% or less when fully hydrated. Preferably, such polymers expand in volume by less than 25%, less than 20%, less than 15%, less than 10% or less than 5%. Even more preferably, the bioadhesive coatings are mucophilic. A polymer that does not appreciably swell upon hydration can be mixed with a polymer that does swell (e.g., CARBOPOL™, poly (acrylic acid), provided that the amount of swelling in the polymer does not substantially interfere with bioadhesiveness.

In certain embodiments, the bioadhesive polymeric coating consists of two layers, an inner bioadhesive layer that does not substantially swell upon hydration and an outer bioadhesive layer that is readily hydratable and optionally bioerodable, such as one comprised of CARBOPOL™.

The bioadhesive polymers discussed above can be mixed with one or more plasticizers or thermoplastic polymers. Such agents typically increase the strength and/or reduce the brittleness of polymeric coatings. Examples of plasticizers include dibutyl sebacate, polyethylene glycol, triethyl citrate, dibutyl adipate, dibutyl fumarate, diethyl phthalate, ethylene oxide-propylene oxide block copolymers such as PLURONIC™ F68 and di(sec-butyl) fumarate. Examples of thermoplastic polymers include polyesters, poly(caprolactone), polylactide, poly(lactide-co-glycolide), methyl methacrylate (e.g., EUDRAGIT™), cellulose and derivatives thereof such as ethyl cellulose, cellulose acetate and hydroxypropyl methyl cellulose (HPMC) and large molecular weight polyanhydrides. The plasticizers and/or thermoplastic polymers are mixed with a bioadhesive polymer to achieve the desired properties. Typically, the proportion of plasticizers and thermoplastic polymers, when present, is from 0.5% to 40% by weight.

In certain embodiments, the bioadhesive polymer coating, in a dry packaged form of a tablet, is a hardened shell.

A tablet or a drug eluting device can have one or more coatings in addition to the bioadhesive polymeric coating. These coatings and their thickness can, for example, be used to control where in the gastrointestinal tract the bioadhesive coating becomes exposed. In one example, the additional coating prevents the bioadhesive coating from contacting the mouth, esophagus, and stomach. In another example, the additional coating remains intact until reaching the small intestine (e.g., an enteric coating).

Examples of coatings include methylmethacrylates, zein, cellulose acetate, cellulose phthalate, HMPC, sugars, enteric polymers, gelatin and shellac. Premature dissolution of a tablet in the mouth can be prevented with hydrophilic polymers such as HPMC or gelatin.

Coatings used in tablets of the invention typically include a pore former, such that the coating is permeable to the drug. Exemplary pore formers include: sugar, mannitol, HPC (hydroxypropyl cellulose), HPMC, dextrates, urea, dendrites, NaCl, etc.

Tablets and drug eluting devices of the invention can be coated by a wide variety of methods. Suitable methods include compression coating, coating in a fluidized bed or a pan, enrobing, and hot melt (extrusion) coating, etc. Such methods are well known to those skilled in the art.

VII. Basifying Agents/Alkaline Stabilizers

Basifying agents/alkaline stabilizers may be used as buffering agents to increase the stability of topiramate in acidic environments. The amount of basifying agent in a subject topiramate formulation typically ranges from 1-75%, preferably 5-50%, more preferably 10-20%.

Suitable basifying agents include, but are not limited to amino methacrylate salts, Poloxamer 188, magnesium oxide, sodium lauryl sulfate, sodium carbonate, sodium bicarbonate, sodium phosphate dibasic, sodium phosphate tribasic, tris base, sodium citrate, magnesium hydroxide, magnesium carbonate, calcium carbonate, and calcium phosphate. Patents such as U.S. Pat. No. 5,180,589, U.S. Pat. No. 6,235,311, U.S. Pat. No. 5,225,202, U.S. Pat. No. 5,030,447 (which are incorporated herein by reference) describe aluminum oxide, all alkali metal hydroxides such as sodium hydroxide, potassium hydroxide or lithium hydroxide, or alkaline earth metal hydroxides such as calcium, magnesium, aluminum hydroxide, dihydroaluminum sodium carbonate, aluminum magnesium hydroxide sulfate, aluminum hydroxide magnesium carbonate co-dried gel, or ammonium hydroxides, calcium carbonate, magnesium carbonate, magnesium stearate, piperazine, sodium acetate, sodium citrate, sodium tartrate, sodium maleate, sodium succinate, and mixtures thereof.

The term alkaline stabilizer refers to a pharmaceutically acceptable alkaline, or basic substance. According to U.S. Pat. No. 6,103,281, examples of such alkaline stabilizers include organic buffering compounds such as tromethamine (e.g., Tris-buffer), N-amino sugars such as N-methyl-D-glucamine (Meglumine), N-ethyl-D-glucamine (Eglumine), alkali salts of citric acid, tartaric acid, alkali metal phosphates, silicates or carbonates, sodium, potassium, magnesium, calcium or aluminum hydroxides and organic amines such as ethylamine, dicyclohexylamine or triethanolamine, or alkaline ammonium salts. Preferred alkaline stabilizers are inorganic basic salts such as magnesium carbonate, magnesium oxide, magnesium hydroxide, magnesium silicate aluminate, magnesium silicate, calcium carbonate, calcium hydroxide, sodium carbonate, sodium hydrogen carbonate. Most preferred alkaline stabilizers are sodium lauryl sulfate, sodium phosphate dibasic, sodium phosphate tribasic, and tris base.

VIII. Surfactants and Co-Surfactants

Surfactants and co-surfactants may also be used to increase the stability of topiramate.

Among the anionic surfactants which may be used are the alkaline salts, ammonium salts, amine salts, amino alcohol salts and magnesium salts of the following compounds: alkyl sulphates, alkyl ether sulphates, alkylamidoether sulphates, alkylarylpolyether sulphates, monoglyceride sulphates; alkylsulphonates, alkylamide sulphonates, alkylarylsulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates and alkyl ether phosphates; acyl sarcosinates, acyl isothionates and N-acyl taurates. Other useful anionic surfactants are fatty acid salts such as oleic, ricinoleic, palmitic and stearic acid salts; coconut oil acid or hydrogenated coconut oil acid; and acyl lactylates. The acyl or alkyl radicals generally comprise from 8 to 30 carbon atoms. Preferred sorbitan esters include oxyethylenated sorbitan monolaurate (4EO) or Polysorbate 20, oxyethylenated sorbitan monostearate (4EO) or polysorbate 61 and oxyethylenated sorbitan monooleate (5EO) or Polysorbate 80. It is also possible to use polyoxyalkylenated alkyl or alkylaryl ether carboxylic acids or salts thereof, polyoxyalkylenated alkylamido ether carboxylic acids or salts thereof, and alkyl D-galactoside uronic acids or salts thereof.

Anionic surfactants are preferably used in proportions of between 1% and 50% by weight and more particularly between 5% and 40% by weight relative to the total weight of the composition.

The composition of the present invention can also contain one or more detergents chosen from nonionic surfactants other than the weakly oxyethylenated sorbitan esters defined above, amphoteric surfactants and zwitterionic surfactants in proportions that are sufficient to give the composition detergent properties.

The additional nonionic surfactants are chosen more particularly from polyethoxylated, polypropoxylated or polyglycerolated fatty acids or alkylphenols or alcohols, with a fatty chain containing 8 to 18 carbon atoms, the number of ethylene oxide or propylene oxide groups being between 2 and 50 and the number of glycerol groups being between 2 and 30, with the exception of oxyethylenated $C_8$-$C_{30}$ fatty acid esters of sorbitan with a number of moles of ethylene oxide of less than or equal to 10.

Copolymers of ethylene oxide and of propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 glycerol groups and in particular 1.5 to 4; polyethoxylated fatty amines preferably containing 2 to 30 mol of ethylene oxide; fatty acid esters of sorbitan oxyethylenated with 12 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or N-acylamidopropyl-morpholine oxides.

Amphoteric surfactants that are preferred are secondary or tertiary aliphatic amine derivatives, in which the aliphatic radical is a linear or branched chain comprising 8 to 22 carbon atoms and which contains at least one carboxylate, sulphonate, sulphate, phosphate or phosphonate water-solubilizing anionic group; ($C_8$-$C_{20}$)alkylbetaines, sulphobetaines ($C_8$-$C_{20}$)alkylamido ($C_1$-$C_6$)alkylbetaines or ($C_8$-$C_{20}$)alkylamido($C_1$-$C_6$)alkylsulphobetaines.

Among the amine derivatives which may be used are the products sold under the name Miranol (disclosed in patents U.S. Pat. Nos. 2,528,378 and 2,781,354 and classified in the CTFA dictionary, 7th edition, 1997, under the name Disodium Cocoamphodiacetate), disodium lauroamphodiacetate, disodium capryloamphodiacetate, disodium caproamphodiacetate, disodium cocoamphodipropionate, disodium lauroamphodipropionate, disodium caproamphodipropionate, disodium capryloamphodipropionate, lauroamphodipropionate acid, cocoamphodipropionate acid.

The detergent surfactants are generally present in proportions of between 1% and 50% by weight relative to the total weight of the composition and preferably between 5% and 40% by weight.

Cationic surfactants are chosen in particular from optionally polyoxyalkylenated primary, secondary and tertiary fatty amine salts; quaternary ammonium salts; imidazoline derivatives; and amine oxides of cationic nature.

Quaternary ammonium salts that are preferred are tetraalkylammonium halides (for example chlorides) such as, for example, dialkyldimethylammonium or alkyltrimethylammonium chlorides, in which the alkyl radical comprises from about 12 to 22 carbon atoms, in particular behenyltrimethylammonium chloride, distearyldimethylammonium chloride, cetyltrimethylammonium chloride, benzyldimethylstearylammonium chloride or stearamidopropyldimethyl (myristyl acetate)ammonium chloride, which are sold under the name "Cepharyl 70" by the company Van Dyk. Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (in particular chlorides or methyl sulphate), and mixtures thereof, can also be used.

Self-emulsifying surfactants which may be used include Cremophor EL, Capryal 90, Labrafil M 1944CS, Labrafil M 212 5.

Co-surfactants which may be used include Carbitol, PEG 400, polypropylene glycol, and dimethyl ether.

All the above compositions, derivatives, precursors, additional components that can be used with the subject topiramate compositions, dosage forms, methods of making and using, etc., are adaptable or directly useable with the instant invention, and are thus expressly incorporated herein by reference.

In order that this invention may be better understood, the following examples are set forth. These examples are for the purpose of illustration only and are not to be construed as limiting the scope of the invention in any manner.

EXAMPLES

Example 1: Degradation of Topamax® Tablets and Topiramate

Degradation of topiramate was detected during a dissolution profile of Topamax® tablets in simulated gastric fluid (i.e., 0.1 N HCl). Topamax® tablets were tested for dissolution in 900 mL of 0.1 N HCl at 37° C. using a USP II apparatus at 50 rpm. Topiramate analysis was carried out using HPLC equipped with Evaporative Laser Light Scattering Detector at 92° C. Separation was achieved using a C-8 reversed-phase column under isocratic conditions of 50% acetonitrile in water. The samples were kept at 4° C. throughout the analysis. Prior to sample injection, the system was equilibrated for 1 hr and subjected to a system suitability test. Linearity was evaluated by linearity curve with power fit. The samples were injected in duplicate and degradation was calculated using the sample area linearity slope and power.

After 4 hours in 0.1 N HCl at 37° C., approximately 20% of the topiramate in the Topamax® tablets was degraded (FIG. 2A). After 17 hrs, approximately 57% of the topiramate was degraded (FIG. 2A).

Degradation of topiramate under acidic conditions was subsequently verified in a stability study where approximately 70% of the topiramate was found to be degraded after 24 hours of incubation in 0.1 N HCl at 37° C. (FIG. 2B).

Topamax® tablets were also tested for dissolution in pH 6.8 phosphate buffer using a USP II apparatus at 50 rpm. Topamax® tablets released >85% of the drug in approx. 20 min, a typical characteristic of an immediate release tablet (FIG. 2C). The drug was stable in pH 6.8 phosphate buffer:

Example 2: Pharmacokinetic Study of Topamax® Tablets in Fed and Fasting Beagle Dogs To evaluate the effect of food on the bioavailability of topiramate, a randomized 2-way crossover relative bioavailability study with Topamax® tablets (containing 100 mg topiramate) was performed in 12 beagle dogs under fed and fasted conditions. In the fasting condition, the Topamax® tablets were given to 6 dogs with 50 mL of water. Dogs were fed after 3 hrs. In the fed condition, the Topamax® tablets were given with food. Drug formulations were administered as a single oral dose, following an overnight fast of at least 10 hours. Animals were monitored to ensure that the tablets were swallowed whole and not chewed. Blood samples (1 mL) were obtained from each dog at different time intervals and blood was placed in lithium heparin micro-vacutainers, centrifuged at 6000 g for 5 minutes and the plasma was removed and stored at 4° C. for subsequent analysis of topiramate. Each sample was analysed using a validated LC/MS/MS method.

The area under the plasma topiramate concentration vs. time curve (AUC), maximum concentration (Cmax), and time required to achieve Cmax (Tmax) were calculated, and the results are indicated in FIG. 3 and Table 1.

TABLE 1

Pharmacokinetic Parameters of Topamax® Tablets in Fed and Fasted Beagle Dogs

| Pharmacokinetic Parameters | Topamax® Tablets in Fasted Beagles, 100 mg | Topamax® Tablets in Fed Beagles, 100 mg |
|---|---|---|
| $AUC_{0-24}$ (μg/mL*hr) | 31.5 ± 4.2 | 45.9 ± 5.5 |
| Cmax (μg/mL) | 8.52 ± 1.6 | 11.9 ± 0.7 |
| Tmax (Hr) | 1.7 ± 0.6 | 1.0 ± 0.1 |

The AUC values indicate that the bioavailability of topiramate from the Topamax® tablets in the fed state was higher than the fasted state. It is well known that food acts as a buffer and raises the pH of the stomach content. In fact, both the AUC and Cmax were significantly reduced (by 45%) in the fasted condition compared to the fed state (FIG. 3). Degradation of topiramate in the acidic environment of the stomach is the likely cause of this reduced bioavailability.

Example 3: Improved Bioavailability of Enteric-Coated, Delayed-Release Topamax® Tablets Manufacturing of Enteric-Coated, Delayed-Release Topamax® Tablets:

Topamax® tablets (100 mg) were coated with the enteric polymer Eudragit L-100. Briefly, Topamax® tablets were manually coated by dipping into a 10% (w/v) solution of Eudragit L-100 in acetone containing 10% w/w triethyl citrate as plasticizer. Each tablet was dipped into the coating solution and was dried overnight to evaporate the solvent. The dipping procedure was repeated three times to produce a final coating weight gain of approximately 7 mg Eudragit L-100 per tablet.

In-Vitro Dissolution of Enteric-Coated, Delayed-Release Topamax® Tablets:

Topamax® tablets and enteric-coated, delayed-release Topamax® were tested for dissolution in 900 mL of phosphate buffer, pH 6.8 at 37° C. using a USP II apparatus at 50 rpm. Dissolution of Topamax® and enteric-coated, delayed-release Topamax® was complete within 30 min.

Pharmacokinetic Testing of Topamax® and Enteric-Coated Delayed-Release Topamax® Tablets in Fed Beagles:

To evaluate the improved bioavailability of enteric-coated, delayed-release topiramate tablets, bioavailability of delayed release topiramate (containing 100 mg topiramate) was evaluated in 6 beagle dogs under fed conditions and results were compared with compared with Topamax® tablet (containing 100 mg topiramate). The test formulations were administered as a single oral dose. Animals were monitored to ensure that the tablets were swallowed whole and not chewed. Blood samples (1 mL) were obtained from each dog at different time intervals and blood was placed in lithium heparin micro-vacutainers, centrifuged at 6000 g for 5 minutes and the plasma was removed and stored at 4° C. for subsequent analysis of topiramate. Each sample was analyzed using a validated LC/MS/MS method.

TABLE 2

Pharmacokinetic Parameters of Topamax ® Tablets, 100 mg and Delayed-Release Topamax ® Tablets in Fed Beagles

| Pharmacokinetic Parameters | Topamax ® Tablets, 100 mg | Delayed-Release Topamax ® Tablets, 100 mg |
|---|---|---|
| $AUC_{0-48}$ (μg/mL*hr) | 45.9 ± 5.5 | 77.5 ± 8.4 |
| Cmax (μg/mL) | 11.9 ± 0.7 | 14.3 ± 1.1 |
| Tmax (Hr) | 1.0 ± 0.1 | 4.3 ± 2.6 |

The pharmacokinetic parameters are summarized in FIG. 4 and Table 2. The AUC value of enteric-coated, delayed-release Topamax® tablets is significantly higher (approximately 70%) than that of the reference Topamax® tablets.

Example 4: Improved Bioavailability of Enteric-Coated, Delayed-Release Topamax® Tablets Manufacturing of Enteric-Coated, Delayed-Release Topamax® Tablets:

Topamax® tablets (100 mg) were coated with the enteric polymer composition Acryl-EZE (Colorcon). Briefly, 10% w/v suspension of Acryl-EZE was prepared in purified water. Topamax® tablets were sprayed with the Acryl-EZE suspension in a Labcoat M pan coater to achieve an approximately 13 mg weight gain. The following coating parameters were used: pump speed 8.0; inlet temperature 45° C.; exhaust temperature 31° C.; atomization air pressure 31 psi; air volume 60 cfm, and pan speed of 20 rpm.

In-Vitro Dissolution of Enteric-Coated Delayed-Release Topamax® Tablets:

The integrity of the enteric-coated, delayed-release Topamax® tablets in acidic medium was tested by observing the intactness of the tablets for 2 hrs in simulated gastric fluid at 37° C., pH 1.2 in a USP II apparatus at 50 rpm. The enteric-coated, delayed-release Topamax® tablets did not dissolve during the 2 hour test period and remained intact. Subsequently, the enteric-coated, delayed-release Topamax® tablets were transferred into 900 mL of phosphate buffer, pH 6.8 at 37° C. in a USP II apparatus at 50 rpm. Dissolution of Topamax® tablets and Acryl-EZE-coated Topamax® was complete within 30 min (FIG. 5A) in phosphate buffer, pH 6.8.

Pharmacokinetic Testing of Topamax® and Enteric-Coated, Delayed-Release Topamax® Tablets in Fasted Beagles:

To evaluate the bioavailability of Topamax® coated with Acryl-EZE formulation, bioavailability of an enteric-coated, delayed-release Topamax® test formulation (containing 100 mg topiramate) was evaluated in 6 beagle dogs under fasted conditions similar to Example 2. The results were compared with Topamax® Tablets (100 mg).

TABLE 3

Pharmacokinetic Parameters of Topamax ® Tablets (100 mg) and Delayed-Release Topamax ® Tablets (100 mg) in Fasted Beagle Dogs

| Pharmacokinetic Parameters | Topamax ® Tablets, 100 mg | Delayed Release Topamax ® Tablets, 100 mg |
|---|---|---|
| $AUC_{0-48}$ (μg/mL*hr) | 31.5 ± 4.2 | 76.4 ± 7.3 |
| Cmax (μg/mL) | 8.52 ± 1.6 | 15.3 ± 2.0 |
| Tmax (Hr) | 1.7 ± 0.6 | 1.5 ± 0.6 |

The pharmacokinetic parameters are summarized Table 3 and profiles shown in FIG. 5B. The enteric-coated, delayed-release Topamax® tablets showed an increased AUC (approximately 140%) and increased Cmax (approximately 80%) compared to the Topamax® reference tablets. The higher bioavailability of Acryl-EZE-coated Topamax® tablets was likely a result of reduced or no degradation of topiramate in the stomach.

Example 5: Topiramate Trilayer Extended-Release (XR) Bioadhesive Tablets, 100 mg The composition of the tablet is depicted in Table 4.

TABLE 4

Composition of Topiramate Trilayer XR Bioadhesive Tablet, 100 mg

| Ingredients | % Per Tablet | Wt. Per Tablet (mg) |
|---|---|---|
| Topiramate | 7.97 | 100.0 |
| Tris Base | 2.39 | 30.0 |
| Ludipress LCE | 36.04 | 452.0 |
| Ethocel 100 Std. FP | 11.96 | 150.0 |
| Talc | 1.28 | 16.0 |
| Aerosil 200 | 0.32 | 4.0 |

TABLE 4-continued

Composition of Topiramate Trilayer
XR Bioadhesive Tablet, 100 mg

| Ingredients | % Per Tablet | Wt. Per Tablet (mg) |
| --- | --- | --- |
| Magnesium Stearate | 0.28 | 3.5 |
| Spheromer III | 35.77 | 448.5 |
| AcDiSol | 3.99 | 50.0 |
| Total | 100 | 1254.0 |

Manufacturing of Topiramate Bioadhesive XR Trilayer Tablets:

The central core blend containing topiramate, tris base, Ludipress LCE, Ethocel 100 Std. FP, talc, and Aerosil was prepared by mixing and initially blending the materials for 5 min. followed by additional blending with magnesium stearate for 5 min. The bioadhesive mix was prepared by mixing and initially blending Spheromer III and AcDiSol for 5 min followed by additional blending with magnesium stearate for 5 min.

Trilayer XR bioadhesive tablets containing 100 mg topiramate in the central core layer and outer bioadhesive layers were compressed using 0.3000×0.8300" capsule-shaped dies (Natoli Engineering) at 4000 psi for 6-8 seconds in a Globe Pharma manual Tablet Compaction Machine (MTCM-1).

Pharmacokinetic Testing of Topamax® Tablets and Bioadhesive Trilayer XR Tablets in Fed Beagles To evaluate the effect of the bioadhesive trilayer XR tablet formulation on the pharmacokinetic parameters of topiramate, bioavailability of topiramate bioadhesive trilayer XR tablet formulation was evaluated in beagle dogs under fed conditions similar to Example 3. The results were compared with Topamax® Tablets. The pharmacokinetic parameters are summarized in Table 5 below.

TABLE 5

Pharmacokinetic Parameters of Topamax ® Tablets
and Bioadhesive Trilayer XR Tablets in Fed Beagles

| Pharmacokinetic Parameters | Topamax ® Tablets, 100 mg | Topiramate Bioadhesive Trilayer XR Tablets, 100 mg |
| --- | --- | --- |
| $AUC_{0-48}$ (µg/mL*hr) | 45.9 ± 5.5 | 58.0 ± 13.8 |
| Cmax (µg/mL) | 12.2 ± 1.5 | 9.0 ± 1.2 |
| Tmax (Hr) | 1.0 ± 0.1 | 2.5 ± 0.5 |

The 100 mg bioadhesive trilayer XR tablets showed higher AUC compared to Topamax® Tablets. The higher Tmax of the bioadhesive XR trilayer tablets compared to the Topamax® was characteristic of a controlled release formulation. Also, the Cmax was reduced compared to the Topamax® tablets (Table 5 and FIG. 6).

Example 6: Topiramate Trilayer Extended-Release (XR) Bioadhesive Tablets Manufactured Utilizing the Drug Concentration Gradient Approach The composition of the tablet is depicted in Table 6.

TABLE 6

Composition of Topiramate Trilayer
XR Bioadhesive Tablets, 100 mg

| Ingredients | % Per Tablet | Wt. Per Tablet (mg) |
| --- | --- | --- |
| Topiramate | 11.1 | 100.0 |
| Hypermellose HPMC 4K cps | 13.3 | 120.0 |
| Methocel E5 | 9.5 | 86.0 |
| Starch | 6.6 | 60.0 |
| Dibasic sodium phosphate | 6.9 | 62.0 |
| Magnesium stearate | 0.8 | 7.5 |
| Spheromer III | 51.8 | 468.5 |
| Total | 100.0 | 904.0 |

Manufacturing of Bioadhesive Trilayer Tablets:

The central core blend containing topiramate, hypermellose, Methocel E5, starch and dibasic sodium phosphate was prepared by mixing and blending the materials for 5 min. followed by additional 5 min blending with magnesium stearate. The bioadhesive mix was prepared by mixing and blending granulated Spheromer III and magnesium stearate for 5 min.

Trilayer XR Bioadhesive tablets containing 70 mg of topiramate in the central core layer and 30 mg in the bioadhesive layers were compressed using 0.3000×0.8300" capsule-shaped dies (Natoli Engineering) at 4000 psi for 6-8 seconds in a Globe Pharma manual Tablet Compaction Machine (MTCM-1).

Pharmacokinetic Testing of Topamax® tablets and Bioadhesive Trilayer XR Tablets in Fed Beagles To evaluate the effect of the bioadhesive trilayer XR tablet formulation on the pharmacokinetic parameters of topiramate, bioavailability of topiramate bioadhesive trilayer XR tablet formulation (100 mg topiramate) was evaluated in 6 beagle dogs under fed conditions similar to Example 3. The area under the plasma topiramate concentration vs. time curve (AUC), maximum concentration (Cmax) and time required to achieve Cmax (Tmax) were calculated, and the results are indicated in Table 7 below.

TABLE 7

Pharmacokinetic Parameters of Topamax ® Tablets and
Topiraamte Bioadhesive Trilayer XR Tablets in Fed Beagles

| Pharmacokinetic Parameters | Topamax ® Tablets, 100 mg | Topiramate Bioadhesive Trilayer XR Tablets 100 mg |
| --- | --- | --- |
| $AUC_{0-48}$ (µg/mL*hr) | 45.9 ± 5.5 | 54.6 ± 5.6 |
| Cmax (µg/mL) | 12.2 ± 1.5 | 6.0 ± 0.7 |
| Tmax (Hr) | 1.0 ± 0.1 | 6.8 ± 1.0 |

The 100 mg bioadhesive trilayer XR tablets showed higher AUC value than the immediate release reference form, Topamax®. The higher Tmax of the bioadhesive XR trilayer tablets compared to the Topamax® was characteristic of a controlled release formulation. Also, the Cmax was reduced compared to the Topamax® tablets (Table 7 and FIG. 7).

Example 7: Topiramate Trilayer Extended-Release (XR) Bioadhesive Tablets, 100 mg Manufactured Utilizing the Drug Concentration Gradient Approach The composition of the tablet is depicted in Table 8.

TABLE 8

Composition of Topiramate Trilayer XR Bioadhesive Tablet, 100 mg

| Ingredients | % Per Tablet | Wt. Per Tablet (mg) |
|---|---|---|
| Topiramate | 11.1 | 100.0 |
| Hypermellose HPMC 4K cps | 6.7 | 60 |
| Methocel E5 | 12.1 | 108.8 |
| Klucel HXF | 6.7 | 60.0 |
| Dibasic sodium phosphate | 6.7 | 60.0 |
| Sodium lauryl sulphate | 4.4 | 40.0 |
| Magnesium stearate | 0.3 | 2.7 |
| Spheromer III | 46.5 | 418.0 |
| Citric acid | 5.6 | 50.0 |
| Total | 100.0 | 899.5 |

Manufacturing of Topiramate Bioadhesive Trilayer Tablets:

The central core blend containing topiramate, hypermellose, Methocel E5, Klucel HXF, sodium lauryl sulphate and dibasic sodium phosphate was prepared by mixing and blending the materials for 5 min. followed by additional 5 min blending with magnesium stearate. The bioadhesive mix was prepared by mixing and initially blending Spheromer III and citric acid for 5 min followed by additional blending with magnesium stearate for 5 min.

Trilayer XR bioadhesive tablets containing 70 mg of topiramate in the central core layer and 30 mg in the bioadhesive layers were compressed using 0.3000×0.8300" capsule-shaped dies (Natoli Engineering) at 4000 psi for 6-8 seconds in a Globe Pharma manual Tablet Compaction Machine (MTCM-1).

Pharmacokinetic Testing of Topamax® tablets and Bioadhesive Trilayer XR Tablets in Fed Beagles To evaluate the effect of the bioadhesive trilayer XR tablet formulation on the bioavailability of topiramate, bioavailability of topiramate bioadhesive trilayer XR tablet formulation (containing 100 mg topiramate) was evaluated in 6 beagle dogs under fed conditions similar to Example 3. The area under the plasma topiramate concentration vs. time curve (AUC), maximum concentration (Cmax) and time required to achieve Cmax (Tmax) were calculated, and the results are indicated in Table 9 below.

TABLE 9

Pharmacokinetic Parameters of Topamax ® Tablets and Topiramate Bioadhesive Trilayer XR Tablets in Fed Beagles

| Pharmacokinetic Parameters | Topamax ® Tablets, 100 mg | Topiramate Bioadhesive Trilayer XR Tablets 100 mg |
|---|---|---|
| $AUC_{0-48}$ (µg/mL*hr) | 45.9 ± 5.5 | 53.8 ± 7.9 |
| Cmax (µg/mL) | 12.2 ± 1.5 | 6.8 ± 0.6 |
| Tmax (Hr) | 1.0 ± 0.1 | 6.0 ± 0.8 |

The 100 mg topiramate bioadhesive tri layer XR tablets showed higher AUC value than the of the immediate release reference form, Topamax® Tablets. The higher Tmax of the bioadhesive XR trilayer tablets compared to the Topamax® was characteristic of a controlled release formulation. Also, the Cmax was reduced compared to the Topamax® tablets (Table 9 and FIG. 8).

Examples 8, 9, 10, 11: Topiramate Bioadhesive Extended-Release (XR) Multiparticulates in Enteric-Coated Capsules The compositions of the topiramate bioadhesive delayed and extended release multiparticulate formulations are depicted in Table 10, 11, 12, and 13 below.

TABLE 10

Composition of Topiramate Bioadhesive, Delayed and Extended Release Multiparticulate Formulation, Example 8

| Ingredients | Wt. Per Tablet (mg) |
|---|---|
| Topiramate | 100.0 |
| Microcrystalline cellulose (Emcocel ® 90M) | 78.1 |
| Hydroxypropyl cellulose (Klucel EF) | 13.4 |
| Dibasic sodium phosphate | 19.5 |
| Sodium lauryl Sulfate | 48.1 |
| Polyvinylpyrrolidone (Povidone K-30) | 8.0 |
| Ammonio alkyl methacrylate copolymer type B (Eudragit ® RS 100) | 2.1 |
| Ammonio alkyl methacrylate copolymer type A (Eudragit ® RL 100) | 2.1 |
| Colloidal silicone dioxide (Aerosil ®) | 0.2 |
| Triethyl citrate | 7.7 |
| Methacrylic acid copolymer type A (Eudragit ® L 100) | 3.1 |
| Methacrylic acid copolymer type B (Eudragit ® S 100) | 11.0 |
| Spheromer ™ III | 11.1 |
| Poloxamer 188 (Lutrol ® F 68) | 0.6 |
| Hard gelatin capsules | 94 |
| Opadry ™ clear | 7.9 |
| Acryl-EZE ™ clear | 39.9 |
| Total | 446.7 |

TABLE 11

Composition of Topiramate Bioadhesive, Delayed and Extended Release Multiparticulate Formulation, Example 9

| Ingredients | Wt. Per Tablet (mg) |
|---|---|
| Topiramate | 100.0 |
| Microcrystalline cellulose (Emcocel ® 90M) | 78.1 |
| Hydroxypropyl cellulose (Klucel EF) | 13.4 |
| Dibasic sodium phosphate | 19.5 |
| Sodium lauryl sulfate | 48.1 |
| Polyvinylpyrrolidone (Povidone K-30) | 8.0 |
| Ammonio alkyl methacrylate copolymer type B (Eudragit ® RS 100) | 2.8 |
| Ammonio alkyl methacrylate copolymer type A (Eudragit ® RL 100) | 2.8 |
| Colloidal silicone dioxide (Aerosil ®) | 0.2 |
| Triethyl citrate | 5.6 |
| Methacrylic acid copolymer type B (Eudragit ® S 100) | 13.8 |
| Spheromer ™ III | 12.2 |
| Poloxamer 188 (Lutrol ™ F 68) | 0.6 |
| Hard gelatin capsules | 94.0 |
| Opadry ™ clear | 9.9 |
| Acryl-EZE ™ clear | 49.3 |
| Total | 458.1 |

TABLE 12

Composition of Bioadhesive, Delayed-Release Topiramate XR Multiparticulate Formulation, Example 10

| Ingredients | Wt. Per Tablet (mg) |
| --- | --- |
| Topiramate | 100.0 |
| Microcrystalline cellulose (Emcocel ® 90M) | 78.1 |
| Hydroxypropyl cellulose (Klucel EF) | 13.4 |
| Dibasic sodium phosphate | 19.5 |
| Sodium lauryl sulfate | 48.1 |
| Polyvinylpyrrolidone (Povidone K-30) | 8.0 |
| Ammonio alkyl methacrylate copolymer type B (Eudragit ® RS 100) | 5.5 |
| Ammonio alkyl methacrylate copolymer type A (Eudragit ® RL 100) | 5.5 |
| Colloidal silicone dioxide (Aerosil ®) | 0.2 |
| Triethyl citrate | 3.4 |
| Methacrylic acid copolymer type A (Eudragit ® L 100) | 8.3 |
| Methacrylic acid copolymer type B (Eudragit ® S 100) | 5.9 |
| Spheromer ™ III | 12.4 |
| Poloxamer 188 (Lutrol ® F 68) | 0.7 |
| Hard gelatin capsules | 94.0 |
| Opadry ™ clear | 8.0 |
| Acryl-EZE ™ clear | 40.3 |
| Total | 451.3 |

TABLE 13

Composition of Bioadhesive, Delayed-Release Topiramate XR Multiparticulate Formulation, Example 11

| Ingredients | Wt. Per Tablet (mg) |
| --- | --- |
| Topiramate | 100.0 |
| Microcrystalline cellulose (Emcocel ® 90M) | 78.1 |
| Hydroxypropyl cellulose (Klucel EF) | 13.4 |
| Dibasic sodium phosphate | 19.5 |
| Sodium lauryl sulfate | 48.1 |
| Polyvinylpyrrolidone (Povidone K-30) | 8.0 |
| Ammonio alkyl methacrylate copolymer type B (Eudragit ® RS 100) | 3.2 |
| Spheromer ™ III | 14.1 |
| Poloxamer 188 (Lutrol ® 68) | 0.7 |
| Hard gelatin capsules | 74.0 |
| Opadry ™ clear | 7.2 |
| Acryl-EZE ™ clear | 35.9 |
| Total | 402.1 |

Manufacturing of Topiramate Bioadhesive Delayed and Extended Release Multiparticulate Formulations Containing 100 mg of Topiramate (Examples 8, 9, 10, and 11):

Active pellets were prepared by extrusion spheronization. Topiramate was blended with Emcocel 90M, Hydroxypropylcellulose EF Pharm, dibasic sodium phosphate, sodium lauryl sulfate, and Povidone K-30 and wet granulated by addition of purified water while mixing in a Hobart mixer. The granulation was then extruded into rods using a Caleva Model 25 twin-roller extruder and spheronized at 1000 rpm, using a Caleva Model 250 spheronizer, to produce multiparticulate cores with diameters ranging from 1-2 mm. The cores were tray-dried at 40° C. for 18 hrs in an oven.

These multiparticulates were coated with release rate controlling polymers Eudragit RS-100 and Eudragit RL-100 (5% w/w) using a Vector MFL.01 laboratory fluid bed coater. A coating composition containing 5% w/v Eudragit RS-100 and Eudragit RL-100 in methanol containing 5% w/v Triethyl citrate was sprayed onto fluidized cores using the following process parameters: inlet temperature=30-32° C.; atomization pressure=18-20 psi; coating solution feed rate=6 mL/min; fluidization=200-250 L/min.

A portion of rate controlled multiparticulate pellets were also coated with delayed-release polymer compositions containing Eudragit L-100 and/or Eudragit S100 using the coating parameters explained above.

A bioadhesive polymer Spheromer™ III coating (5% w/w) was applied to the extended release cores in a Vector MFL.01 laboratory fluid bed coater. A 5% (w/v) Spheromer™ III solution in methanol containing 5% w/v Poloxamer 188 (Lutrol F68) was sprayed onto fluidized cores using the following process parameters: inlet temperature=35° C.; atomization pressure=18-20 psi; coating solution feed rate=6 mL/min; fluidization=200-250 L/min.

The bioadhesive, delayed-release topiramate XR multiparticulate formulations containing 100 mg topiramate, was encapsulated in size "0" gelatin capsules, and the capsule was banded with gelatin solution (4 gelatin capsules dissolved in 10 mL of distilled water). 10% Opadry® Clear solution was prepared in mixture of ethanol and water (88:12). Briefly, 10% w/v suspension of Acryl-EZE™ was prepared in ethanol. The topiramate capsules were sprayed with Opadry solution for 2% weight gain followed by Acryl-EZE coating suspension in a Labcoat M pan coater to get approximately 10% weight gain. The following coating parameters were used: pump speed 8.0; inlet air temperature 45° C.; exhaust temperature 31° C.; atomization air pressure 31 psi; air volume 60 cfm and pan speed 20 rpm.

In-Vitro Dissolution of Topiramate Bioadhesive Delayed and Extended Release Multiparticulate Formulations (Examples 8, 9, 10, and 11):

Topiramate bioadhesive XR multiparticulates in enteric-coated capsules were tested for dissolution using a USP II apparatus at 50 rpm. The capsules were stirred in 900 mL of 0.1 N HCl for 2 hrs and subsequently transferred into phosphate buffer, pH 6.8 for 24 hrs at 37° C. The dissolution profile was compared with Topamax® Tablets as indicated in FIG. 9. The capsules did not dissolve during the 2 hr test period in 0.1 N HCl and remained intact. Dissolution of multiparticulates formulations was completed between 6-10 hrs as shown in FIG. 9.

Figure 10:
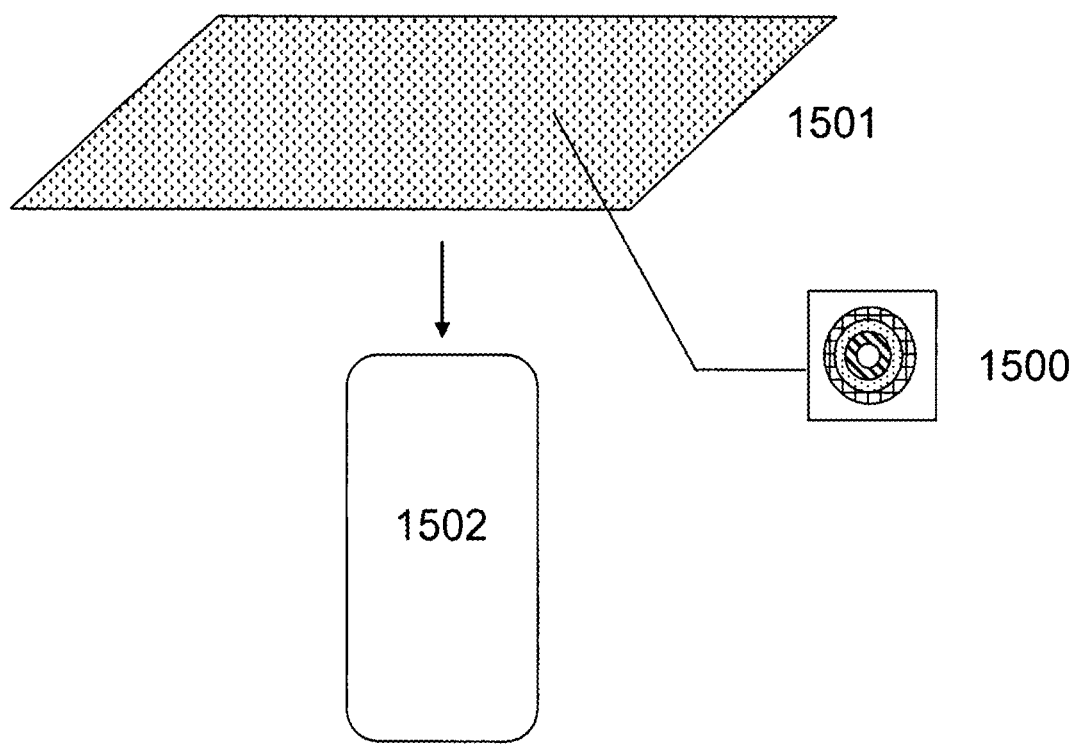
FIG. 10 shows the pharmacokinetic profiles of Topamax® tablets, 100 mg and topiramate bioadhesive delayed and extended-release topiramate multiparticulate formulations (100 mg) (from Examples 8-11).

Pharmacokinetic Testing of Topiramate Bioadhesive, Delayed and Extended Release Multiparticulate Formulations in Fasted Beagles (Examples 8, 9, 10, and 11):

Topiramate Bioadhesive, Delayed and Extended Release Multiparticulate Formulations (100 mg of topiramate) test formulations were administered to cohorts of 6 beagle dogs each under fasted state, and plasma levels of topiramate were measured using LC/MS/MS as in Example 2 (FIG. 10).

The area under the plasma topiramate vs. time curve (AUC), maximum concentration (Cmax) and time required to achieve Cmax (Tmax) were calculated and were compared with Topamax® Tablets. The results are shown in the Table 14 below and FIG. 10.

TABLE 14

Pharmacokinetic Parameters of Topamax ® Tablets and Topiramate Bioadhesive Delayed and Extended Release Multiparticulates in Enteric-Coated Capsules in Fasted Beagles

| Pharmacokinetic Parameters | Topamax ® Tablets, 100 mg | Topiramate Bioadhesive Trilayer XR Tablets 100 mg Example 8 | Topiramate Bioadhesive Trilayer XR Tablets 100 mg Example 9 | Topiramate Bioadhesive Trilayer XR Tablets 100 mg Example 10 | Topiramate Bioadhesive Trilayer XR Tablets 100 mg Example 11 |
|---|---|---|---|---|---|
| AUC (μg/mL*hr) | 31.5 ± 4.2 | 41.9 ± 7.1 | 58.3 ± 5.9 | 48.1 ± 5.5 | 46.2 ± 8.3 |
| Cmax (μg/mL) | 8.52 ± 1.6 | 5.9 ± 0.7 | 8.5 ± 0.5 | 4.9 ± 0.3 | 6.8 ± 1.2 |
| Tmax (Hr) | 1.7 ± 0.6 | 3.3 ± 0.5 | 2.8 ± 0.5 | 6.4 ± 0.4 | 4.5 ± 0.4 |

The AUC was higher for topiramate bioadhesive multiparticulate XR formulations compared to Topamax® tablets (Table 14, FIG. 10, Examples 8, 9, 10, and 11).

Example 12: Topiramate Bioadhesive Delayed and Extended Release Multiparticulates Formulations Type A and Type B The composition of the Delayed Release Topiramate XR Multiparticulate Formulations Type A and Type B are depicted in Table 15 and Table 16 respectively.

TABLE 15

Composition of Topiramate Bioadhesive Delayed and Extended Release Multiparticulate Formulation, Type A

| Composition | Wt. per Tablet (mg) |
|---|---|
| Topiramate | 100.0 |
| Microcrystalline cellulose (Emcocel 90 M) | 79.7 |
| Hydroxypropyl cellulose (Klucel EF) | 13.6 |
| Dibasic Sodium Phosphate | 19.9 |
| Sodium Lauryl Sulfate | 49.1 |
| Polyvinylpyrrolidone | 8.2 |
| Ammonio alkyl methacrylate type A (Eudragit ® RL 100) | 5.6 |
| Ammonio alkyl methacrylate type B (Eudragit ® RS 100) | 5.6 |
| Triethyl Citrate | 0.3 |
| Colloidal silicone dioxide | 0.2 |
| Spheromer ™ III | 11.9 |
| Poloxamer 188 (Lutrol F68) | 0.8 |
| Opadry ™ clear | 11.1 |
| Acryl-EZE ™ clear | 36.9 |
| Total | 342.7 |

TABLE 16

Composition of Topiramate Bioadhesive Delayed and Extended Release Multiparticulates Formulation, Type B

| Components | Wt. per Tablet (mg) |
|---|---|
| Topiramate | 100.0 |
| Microcrystalline cellulose (Emcocel 90M) | 79.7 |
| Hydroxypropyl cellulose (Klucel EF) | 13.6 |
| Dibasic sodium phosphate | 19.9 |
| Sodium lauryl sulfate | 49.1 |
| Polyvinylpyrrolidone (Povidone K-30) | 8.2 |
| Ammonio alkyl methacrylate copolymer type A (Eudragit RL-100) | 2.2 |
| Ammonio alkyl methacrylate copolymer type B (Eudragit RS-100) | 2.2 |
| Colloidal silicon dioxide (Aerosil) | 0.2 |
| Triethyl citrate | 3.0 |
| Methacrylic acid copolymer type B | 8.0 |
| Spheromer ™ III | 11.9 |
| Poloxamer 188 (Lutrol F 68) | 0.6 |
| Opadry ® Clear | 12.2 |
| Acryl-EZE ™ White | 40.7 |
| Total | 351.5 |

Manufacturing of Bioadhesive Delayed Release Topiramate XR Multiparticulates Formulations Type A and Type B:

Active pellets were prepared by extrusion spheronization. Topiramate was blended with Emcocel 90M, hydroxypropylcellulose EF Pharm, dibasic sodium phosphate, sodium lauryl sulfate, and Povidone K-30 and wet granulated by addition of purified water while mixing in a Hobart mixer. The granulation was then extruded using a Caleva Model 25 twin-roller extruder and spheronized at 1000 rpm, using a Caleva Model 250 spheronizer, to produce multiparticulate cores with diameters ranging from 1-2 mm. The cores were dried at 45±5° C. using a Fluid Air Model 5 Fluidized bed unit.

Multiparticulates were subsequently coated with a release rate-controlling polymer solution containing Eudragit RS-100, Eudragit RL-100, triethyl citrate and colloidal silicon dioxide in methanol (5.5% w/w weight gain) using a MFL.01 Vector Fluid Bed Coater using the parameters mentioned in Example 8. Another portion of these rate controlled multiparticulates (in Type B formulation) were coated with a delayed release polymer composition containing Eudragit S-100 (10% weight gain).

A bioadhesive polymer coating solution containing Spheromer™ III, Poloxamer 188 and methanol (5.5% w/w weight gain) was applied to the Eudragit RS-100 and Eudragit RL-100 coated cores by Wurster-coating with a Vector MFL.01 laboratory fluid bed coater. For bioadhesive coating, a 10% (w/v) Spheromer™ III solution in methanol containing 5% (w/v) Poloxamer 188 (Lutrol F68) was sprayed onto fluidized cores using the process parameters mentioned in Examples 8-11.

Multiparticulate pellets [uncoated pellets; and release rate controlling polymers Eudragit RS-100 and Eudragit RL-100 and Spheromer™ III coated pellets (Type A); and delayed release polymer Eudragit S 100 and Spheromer™ III coated pellets (Type B)] equivalent to 100 mg topiramate were encapsulated in size "0" gelatin capsules and capsules were banded with gelatin solution. The banded capsules were coated with a 3% (w/w) coating of Opadry™ Clear followed by 10% weight gain of Acryl-EZE enteric coating using a O'Hara Labcoat M pan coating system. Briefly, 10% w/v suspension of Acryl-EZE™ was prepared in ethanol. 10% (w/w) Opadry® Clear solution was prepared in mixture of ethanol and water (88:12, v:v). The following coating parameters were used: pump speed=8.0%; an inlet air temperature=35° C.; exhaust temp.=31° C.; an atomization air pressure=20 psi; air volume=60 cfm and pan speed=20 rpm.

Figure 11:
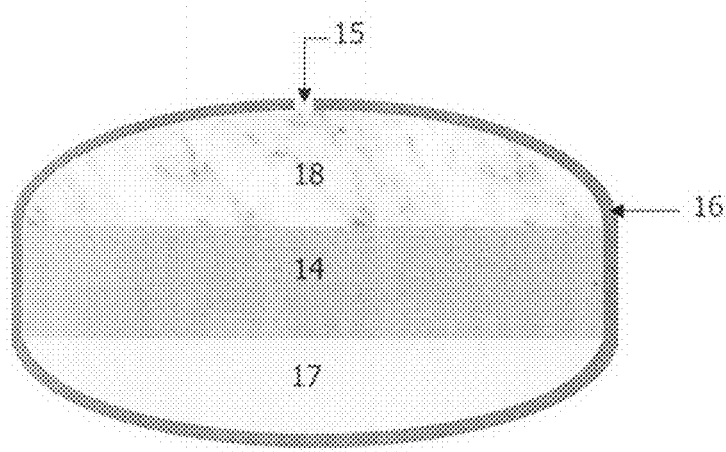
FIG. 11A shows the dissolution profile of topiramate bioadhesive delayed and extended-release multiparticulate capsules (100 mg) Type A and Type B in phosphate buffer, pH 6.8 at 37° C.
FIG. 11B shows topiramate plasma concentration time profiles after administration of a single dose of 100 mg topiramate bioadhesive delayed and extended release multiparticulate formulations type A and type B, and Topamax® tablets (100 mg) in healthy human volunteers.

In-Vitro Dissolution of Topiramate Bioadhesive Delayed and Extended Release Multiparticulate Formulations Type A and Type B:

The integrity of the topiramate bioadhesive delayed and extended release multiparticulate formulation; type A and type B in acidic medium was tested by observing the capsules for 2 hrs in simulated gastric fluid (0.1N HCl, pH 1.2) at 37° C. in a USP II apparatus at 50 rpm for signs of failure. The capsules did not dissolve during the 2 hr test period and remained intact. The multiparticulate formulation Type A demonstrated a controlled release dissolution profile releasing 40% drug at 2 hrs, 75% at 4 hrs and more than 85% at 6 hrs. The multiparticulate formulation Type B released >60% drug at 1 hrs and >85% at 4 hrs as it has more delayed release multiparticulates. The dissolution profiles generated in pH 6.8 buffer are shown in FIG. 11A.

Singe-Dose Pilot Human Pharmacokinetic Study Comparing Topiramate Bioadhesive Delayed and Extended Release Multiparticulate Formulations Type A and Type B with Topamax® Tablets A single-dose, three way crossover study comparing the pharmacokinetics and tolerability of topiramate bioadhesive extended release multiparticulates formulations 100 mg (Type A and Type B) and an equal dose of Topamax® tablets was carried out in 12 healthy volunteers. Each subject received a single dose of each of the formulations in random order following a light breakfast and plasma levels of topiramate were measured using LC/MS/MS. The doses were separated by 2-week washout periods. FIG. 11B shows the topiramate plasma concentration vs time graph.

The area under the plasma topiramate vs time curve (AUC), maximum concentration (Cmax), time to maximum concentration (Tmax) were calculated and are indicated in the Table 17.

The results depicted in Table 17 show that the AUC of topiramate from the topiramate bioadhesive delayed and extended release multiparticulate formulations were 106% (type A) and 94% (type B) of the Topamax® tablets. As desired, the Cmax was greatly reduced by 47% (type A) and 37% (type B) for the XR formulations and also the variability in the Cmax was significantly reduced. Tmax of the XR formulations was extended to 22 hrs (Type B) and 26 hrs (Type A), which is typical of controlled release formulations. The high Cmax of the Topamax® tablets is linked to side effects. Both the formulations showed reduced variability in $AUC_{0-144}$ as well as in Cmax.

Example 13

Micronized Topiramate Immediate Release Tablets Formulation

Preparation of Micronized Topiramate Immediate Release Tablets:

Jet Milling of Topiramate

Topiramate was micronized using a jet mill (Glenn Mills Inc.). The jet mill was connected to the compressed air line and the regulator was set to 120 psi. The main valve on the jet mill was opened and both the O and P line regulators were adjusted to 90 psi. 50.0 g of topiramate was weighed and added slowly to the feed chute. The jet mill was allowed to run for 5 minutes after all of the topiramate was in the mill. The main air valve was closed and topiramate was recovered from the collection vessel, filter bag, and main frame. This entire process was then repeated twice with the recovered product. The final product was reweighed and determined to be 30.6 g. Particle size analysis of the milled topiramate was carried out using the Microtrac-S3000 particle size analyzer. FIG. 12A shows the particle size analysis of the final micronized topiramate. The d10, d50, and d90 of the micronized topiramate were 1.41, 2.89, 7.29 microns, respectively.

Manufacturing of Immediate Release Topiramate Tablets, 100 mg

Immediate release tablets (Table 18) containing 100 mg micronized topiramate were compressed using 0.2900" round shaped die (Natoli Engineering) at 4000 psi for 6-8 seconds in a Globe Pharma manual tablet compression machine. The composition of the immediate release topiramate tablet is shown in Table 18:

TABLE 17

PK parameters after a single dose of 100 mg Bioadhesive Delayed Release Topiramate XR Multiparticulate Formulations Type A and Type B and an equivalent dose of Topamax ® tablets.

| PK Parameters | Topamax ® Tablets 100 mg | Topiramate Bioadhesive Delayed Release XR Multiparticulate Formulation, Type A, 100 mg | Bioadhesive Delayed Release Topiramate XR Multiparticulate Formulation, Type B, 100 mg |
|---|---|---|---|
| $AUC_{0-144}$ (ng/mL*hr) | 73156.27 ± 27858.55 | 69717.88 ± 21587.10 | 67164.90 ± 20734.16 |
| $AUC_{0-inf}$ (ng/mL*hr) | 83068.23 ± 35801.35 | 88027.03 ± 44281.63 | 78268.80 ± 30653.61 |
| Cmax (ng/mL) | 2057.50 ± 634.29 | 1101.83 ± 304.56 | 1294.50 ± 357.10 |
| Tmax (Hr) | 2.58 ± 0.90 | 25.92 ± 11.07 | 21.92 ± 9.50 |

TABLE 18

Unit Dose Composition of Micronized Topiramate
Immediate Release Tablets, 100 mg

| Components | Wt. per tablet (mg) |
|---|---|
| Micronized Topiramate | 100.00 |
| Microcrystalline Cellulose | 46.69 |
| Dibasic Sodium Phosphate | 19.95 |
| Sodium lauryl sulfate | 49.16 |
| AcDiSol | 54.20 |
| Magnesium Stearate | 0.81 |
| Total | 271.00 |

Pharmacokinetic Study of Micronized Topiramate Immediate Release Tablets in Fasted Beagle Dogs The bioavailability of the micronized topiramate immediate release tablets, 100 mg, was evaluated in beagle dogs under fasted conditions. The drug formulation was administered as a single oral dose. Animals were monitored to ensure that the tablets are swallowed whole and not chewed. From each dog, blood samples (1 mL) were obtained at the following time points: "0" hour (pre-dosing) 0.5, 1, 1.5, 2, 2.5, 3, 3.5, 4, 4.5, 5, 6, 8, 10, 12, 16, 24, and 36 hours post dosing, for a total of 18 blood samples per study period. The blood was placed in lithium heparin micro-vacutainers, centrifuged at 6000 g for 5 minutes and the plasma was removed and stored at 0° C. for subsequent analysis of topiramate. Plasma samples were tested for topiramate using a validated LC/MS/MS method. The pharmacokinetic parameters were observed following the validated software. FIG. 12B shows the topiramate plasma concentration profiles for both Topamax and immediate release tablets containing micronized topiramate. The pharmacokinetic parameters are summarized in Table 19.

TABLE 19

PK parameters after a single dose of 100 mg Micronized
Topiramate Immediate Release and an equivalent dose
of Topamax tablets in Fasted Beagles.

| PK Parameters | Topamax Tablets (100 mg) | Immediate Release Tablets with Micronized Topiramate (100 mg) |
|---|---|---|
| $AUC_{0-36}$ (µg/mL*hr) | 31.5 ± 4.2 | 55.8 ± 5.3 |
| Cmax (µg/mL) | 8.5 ± 1.6 | 11.6 ± 0.7 |
| Tmax (hr) | 1.7 ± 0.6 | 1.1 ± 0.2 |

The micronized topiramate immediate release formulation showed improved bioavailability compared to Topamax tablets.

As expected, PK results in Table 19 showed improved extent of exposure of the micronized topiramate immediate release formulation compared to Topamax tablets. This micronized topiramate immediate release formulation also has a shorter Tmax than Topamax tablets.

Example 14

Preparation of Amorphous Topiramate

Amorphous topiramate was prepared by a spray drying process using Buchi spray dryer. Table 20 specifies the composition of the spray-dried topiramate.

TABLE 20

Composition of Spray Dried Amorphous Topiramate

| Ingredients | % w/w |
|---|---|
| Topiramate | 65.8 |
| Tris Base | 7.9 |
| Methocel E5 | 6.6 |
| Povidone K15 | 19.7 |
| Total | 100.0 |

For manufacturing of spray dried amorphous topiramate, 3 g of Tris base was dissolved in water. 25 g of topiramate, 2.5 g of Methocel E5, and 7.5 g of Povidone K15 was dissolved in 200 mL of methanol and was mixed with tris base solution. This solution was sprayed using Buchi Spray Drier using the following parameters: Inlet temperature—100° C.; Nitrogen flow rate—450; and Aspirator—95%. After spraying whole of the solution, the Spray Drier was allowed to cool down for 20 min. The cyclone and the collection vessel were then removed and product was collected using spatula and was dried under vacuum overnight.

The DSC scan of the final product was taken using the Perkin Elmer Pyris 6 DSC. FIG. 13 shows the DSC scan of topiramate (FIG. 13A) and spray dried topiramate (FIG. 13B). FIG. 13A shows large peak at 125° C. with topiramate whereas FIG. 13B shows no peak at 125° C. with spray dried topiramate indicating that all the topiramate was converted to amorphous form.

Example 15

Preparation of 0.6 to 1.4 mm Topiramate Pellets

Table 21 specifies the composition of the 0.6-1.4 mm topiramate pellets produced by granulation, extrusion, spheronization, and drying

TABLE 21

Components of the topiramate pellet formulation

| Components | % w/w | Wt (g)/Batch |
|---|---|---|
| Topiramate | 43 | 161.3 |
| Microcrystalline cellulose (MCC) | 25 | 93.8 |
| Hydroxypropyl cellulose (HPC) | 5 | 18.8 |
| Dibasic Sodium Phosphate | 12 | 45 |
| Sodium lauryl sulfate (SLS) | 10 | 37.5 |
| AcDiSol | 5 | 18.8 |
| Total | 100 | 375 |

Blending

A dry blend was made by mixing topiramate, microcrystalline cellulose, hydroxypropyl cellulose (11.3 g), dibasic sodium phosphate, sodium lauryl sulfate, and AcDiSol in a planetary mixer for 15 min.

Granulation

The remaining hydroxypropyl cellulose (7.5 g) was dissolved in 200 mL of HPLC-grade water. A plastic spray bottle was filled with this hydroxypropyl cellulose solution and weighed. The whole solution was slowly sprayed onto the dry blend while mixing. The granulation was continued with of HPLC-grade water until the resulting granules held together when compressed. The mixing was continued for an additional 5 min.

Extrusion

An extruder was equipped with a 0.8 mm screen and its speed was adjusted at 10 rpm. The granules were added slowly to the running extruder using a plastic scoop. At the completion of extrusion, the extrudate was transferred into the mixer bowl using a small brush. Any product that was forced out of the extruder top without being extruded was transferred back into the machine for extrusion.

Spheronization

The spheronizer was assembled with a cross-hatched patterned spheronization plate, and its speed was set at 1250 rpm. A supply of nitrogen gas at 120 psi was connected to the spheronizer. The spheronizer was started and all of the extrudate was added to the spheronizer at once. The spheronization was continued for 5 min until the particles visually appeared evenly rounded. The spheronized particles (pellets) were removed and transferred into the product bowl of a mini fluid bed drier.

Drying

A supply of compressed air at 120 psi was connected to the fluid bed drier. The inlet air was set at 50° C. and pellets were dried by fluidization as described below. The dried pellets were refrigerated immediately after drying.

Drying Process Parameters and Loss on Drying Values

| Process | Fluid Bed Drying Time (min) | | | | |
|---|---|---|---|---|---|
| | 0 | 45 | 105 | 170 | 225 |
| Drying Air Flow (LPM) | 330 | 330 | 306 | 315 | 315 |
| Drying Air Temperature (° C.) | 50 | 50 | 50 | 50 | 50 |
| Sample Collected (g) | 1.0 | 1.0 | 1.0 | 1.0 | 1.0 |
| Loss on drying (%) | 30.3 | 14.0 | 5.6 | 2.5 | 1.1 |

Particle Size

Topirmate pellets were sieved through a stack of 14, 16, 18, 20, 25, and 30 mesh screens on a mechanical sieve shaker. The sieves were shaken for 7 min. The particles retained on each screen and on the bottom tray were collected and weighed. The weight fraction of particles in each size class was calculated. The particle size distribution data are given in the following table.

| U.S. Std. Mesh Size | Opening (mm) | Size Class | Weight (g) | Weight Fraction (%) |
|---|---|---|---|---|
| 14 | 1.4 | >14 | 0.04 | 0.01 |
| 16 | 1.18 | <14/>16 | 1.95 | 0.67 |
| 18 | 1.00 | <16/>18 | 95.11 | 32.85 |
| 20 | 0.85 | <18/>20 | 157.11 | 54.26 |
| 25 | 0.71 | <20/>25 | 33.88 | 11.70 |
| 30 | 0.6 | <25/>30 | 1.33 | 0.46 |
| pan | | <35 | 0.15 | 0.05 |
| | | Total | 289.57 | |

Example 16

Topiramate Rapidly Disintegrating Extended Release (XR) Pelletized Tablets, 100 Mg Table 22 specifies the composition of Topiramate rapidly disintegrating extended release (XR) Pelletized Tablets

TABLE 22

Components of the topiramate bioadhesive extended release (XR) pellet formulation

| Component | Wt. per Tablet (mg) |
|---|---|
| Topiramate | 100 |
| Microcrystalline cellulose (MCC) | 58.2 |
| Hydroxypropyl cellulose (HPC) | 11.6 |
| Dibasic Sodium Phosphate | 27.9 |
| Sodium lauryl sulfate (SLS) | 23.3 |
| AcDiSol | 11.6 |
| Ammonio alkyl methacrylate copolymer type A (Eudragit RL-100) | 3.0 |
| Ammonio alkyl methacrylate copolymer type B (Eudragit RS-100) | 8.7 |
| Triethyl citrate | 0.6 |
| Spheromer ™ III | 9.5 |
| Succinic acid | 13.1 |
| Citric acid | 1.2 |
| Acryl-EZE ™ | 27.8 |
| Ludipress | 278.5 |
| Avicel PH 105 | 148.2 |
| Magnesium Stearate | 1.7 |
| Total | 724.9 |

Manufacturing of Topiramate Rapidly Disintegrating Extended Release (XR) Pelletized Tablets:

Granulation of the composition of Table 22 was performed as discussed in Example 15. After the granulation, a portion of the granules was dried for subsequent use as an immediate release component.

Topiramate pellets were prepared by extrusion spheronization as discussed in Example 15.

Preparation of Topiramate Controlled Release Pellets.

The topiramate pelletized tablets were coated with release rate-controlling polymers solution containing Eudragit RS 100, Eudragit RL 100, triethyl citrate and colloidal silicon dioxide in methanol (6.6% w/w weight gain), using MFL.01 Vector Fluid Bed Coater. The following process parameters were used for bioadhesive coating process: inlet temperature=32° C.; atomization pressure=18 psi; spray pump speed=25 rpm; fluidization=250 L/min.

Preparation of Topiramate Bioadhesive Extended Release Pellets.

A bioadhesive polymer coating solution containing Spheromer™ III, Succinic acid and citric acid (12% w/w weight gain) was applied over the release rate-controlling polymers Eudragit RS 100 and Eudragit RL 100 coated cores by Wurster-coating with a Vector MFL.01 laboratory fluid bed coater.

An enteric polymer coating solution containing Acryl-EZE solution in methanol was applied (10% w/w wt. gain) to the bioadhesive extended release pellets.

Enteric polymer coated topiramate bioadhesive controlled release pellets were mixed with topiramate immediate release granules, Ludipress, Avicel PH 105, and magnesium stearate in a V-shell blender. Topiramate rapidly disintegrating XR pelletized tablets containing 100 mg of topiramate were compressed using 0.2500×0.7090" capsule-shaped dies (Natoli Engineering) at 2000 psi for 2 seconds in a Globe Pharma manual Tablet Compaction Machine (MTCM-1).

In-Vitro Dissolution of Topiramate Rapidly Disintegrating XR Pelletized Tablets:

The dissolution of the tablet was tested by observing the tablet for 2 hrs in simulated gastric fluid (0.1N HCl, pH 1.2) at 37° C. in a USP I apparatus at 100 rpm followed by in ammonium phosphate buffer, pH 6.8. The tablet demonstrated a controlled release dissolution profile as shown in FIG. 14.

Example 17: Topiramate Delayed Release Rapidly Disintegrating Extended Release (XR) Pelletized Tablets, 100 mg Topiramate bioadhesive controlled release pellets as discussed in Example 16, were mixed with topiramate granules, Ludipress, Avicel PH 105, and magnesium stearate in a V-shell blender. Topiramate rapidly disintegrating XR pelletized tablets containing 100 mg of topiramate were compressed using 0.2500×0.7090" capsule-shaped dies (Natoli Engineering) at 2000 psi for 2 seconds in a Globe Pharma manual Tablet Compaction Machine (MTCM-1). These tablets were subsequently coated with an enteric coating composition as outlined in example 3 to prepare Topiramate delayed release rapidly disintegrating XR pelletized tablets. A schematic design of Topiramate delayed release rapidly disintegrating XR pelletized tablet is shown in FIG. 15.

Example 18: Topiramate Rapidly Disintegrating Extended Release (XR) Pelletized Tablets, 100 mg with Split Function Topiramate delayed release bioadhesive controlled release pellets from Example 16, were mixed with topiramate granules, Ludipress, Avicel PH 105, and magnesium stearate in a V-shell blender. Separately, Avicel, Ludipress, and magnesium stearate were mixed to make a rapidly disintegrating placebo mixture. Multilayer topiramate rapidly disintegrating XR pelletized longitudinally compressed tablets containing 100 mg of topiramate with split function were compressed using deep fill 0.2900" dies and punches (Natoli Engineering) at 2000 psi for 2 seconds in a Globe Pharma manual Tablet Compaction Machine (MTCM-1) having placebo layer between the two active layers. A score line was applied on the middle placebo layer. A schematic design of topiramate rapidly disintegrating XR pelletized tablet with divisible mechanism is shown in FIG. 16.

Example 19: Steady State Pharmacokinetic Profiles of Topiramate Bioadhesive Extended Release Tablets Reduce degree of fluctuation is expected from extended release topiramate formulations as disclosed herein for a multi-dose study. FIGS. 17A and 17B shows the predicted steady state plasma levels of topiramate after multiple dosing. The predicted plasma topiramate levels observed for topiramate bioadhesive delayed and extended release multiparticulate formulations for Type A and Type B were based on a single dose pharmacokinetic trial in healthy volunteers as discussed in Example 12.

Example 20: Topiramate Delayed Extended Release Capsule, 100 mg

Table 23 specifies the composition of topiramate XR capsule, 100 mg comprising of extended release multiparticulates without bioadhesive polymer. The manufacturing of XR capsule was identical to that of Examples 8-11 with the exception that no Spheromer III bioadhesive coating was applied onto the Eudragit RL-100/RS-100 coated pellets.

Enteric-coated capsules were tested for dissolution in USP II apparatus at 50 rpm. The capsules were stirred in 900 mL of 0.1 N HCl for 2 hrs and subsequently transferred into phosphate buffer, pH 6.8 for 24 hours at 37° C. Capsules did not dissolve during 2 hours of testing in 0.1 N HCl and remained intact. The release profile for the capsules was identical to the multiparticulate formulation "A" as given in Example 12 and demonstrated a controlled release profile releasing 40% of drug at 2 hrs, 75% at 4 hrs and greater than 85% at 6 hrs.

TABLE 23

Unit Dose Compositions of Topiramate XR Capsule, 100 mg

| | | 100 mg | |
| --- | --- | --- | --- |
| Components | Function | Weight (mg) | Amount (% w/w) |
| Topiramate | Active | 100.0 | 23.8 |
| Microcrystalline Cellulose | Spheronization aid | 80.24 | 19.1 |
| Hydroxypropyl Cellulose | Binder | 13.6 | 3.2 |
| Povidone K-30 | Binder | 7.9 | 1.9 |
| Dibasic Sodium Phosphate | Solubilizer | 19.9 | 4.7 |
| Sodium Lauryl Sulfate | Surfactant | 49.2 | 11.7 |
| Ammonio Methacrylate Copolymer, Type A (Eudragit ® RL 100) | Release rate controlling polymer | 3.3 | 0.8 |
| Ammonio Methacrylate Copolymer, Type B (Eudragit ® RS 100) | Release rate controlling polymer | 3.3 | 0.8 |
| Colloidal Silicon Dioxide | Glidant | 0.1 | <0.1 |
| Triethyl Citrate | Plasticizer | 0.3 | 0.1 |
| Opadry ® Clear (YS-1-19025-A) | Film Former, seal coating | 11.3 | 2.7 |
| Acryl-EZE ™ White (93O18509) | Enteric coating | 38.4 | 9.1 |
| Gelatin capsule | Carrier | 93.0 | 22.1 |
| Water, Purified | Solvent | * | * |
| Methanol | Solvent | * | * |
| Ethanol (Dehydrated Alcohol) | Solvent | * | * |
| Total | | 420.5 | 100.0 |

* Solvents used as process aid, removed during processing

Single-Dose Human Pharmacokinetic Study Comparing Topiramate Non-Bioadhesive Delayed XR Capsule, 100 mg (Example 20), Topiramate Bioadhesive Delayed XR Capsule 100 mg (Example 12) with Topamax Tablets A single-dose, three-way crossover study comparing the pharmacokinetics and tolerability of three topiramate containing formulations at 100 mg dose was carried out in 12 healthy volunteers. Each subject received a single dose of each of the formulation in random order following a light breakfast and plasma levels of topiramate were measured using the LC/MS/MS. The doses were separated by a 2-week washout period. FIG. 18 shows the topiramate plasma concentrations vs. time profiles. As shown in Table 24, topiramate XR formulation with bioadhesive showed improved bioavailability compared to that without bioadhesive formulation. Both topiramate XR formulations, compared to Topamax tablets, showed improved bioavailability. This was primarily due to delayed release coating onto the extended release formulations not allowing the topiramate to be released in the stomach where it is susceptible to breakdown.

TABLE 24

Summary of Pharmacokinetic Parameters

| PK Parameter | Topiramate XR Bioadhesive (100 mg) | Topiramate XR Non-Bioadhesive (100 mg) | Topamax (100 mg) |
|---|---|---|---|
| $C_{max}$ (ng/mL) | 1005 | 1051 | 1479 |
| $T_{max}$ (hr) | 24 | 24 | 5 |
| $AUC_{0-\infty}$ (ng/mL*hr) | 77751 (114%) | 71681 (105%) | 68142 (100%) |

Assessment of Cognitive Functions with Topiramate Formulations

In addition to PK testing, the cognition profiles of various topiramate formulations were also tested using a battery of neuropsychological tests. These tests included the Computerized Neuropsychological Test Battery (CNTB) as well as classic paper-and-pencil tests, e.g., Controlled Oral Word Association Test (COWAT) and Symbol Digital Modalities Test, i.e., timed graphomotor coding task (SDMT). CNTB testing uses a computer as an expert system and was selected as being more comprehensive in its sampling of neuropsychological functions. Choice reaction time, paired associate learning, delayed recall, visual memory and working memory were the five CNTB modules, among 11 modules, used in this study. COWAT is a timed test of phonemic verbal frequency generating words beginning with a specific letter. Patients were familiarized with the cognition testing procedure prior to study entry during a training session. A baseline assessment was conducted and then patients were randomized to receive one of three 100 mg topiramate formulations. Tests were applied at 2 hours, 5 hours, 9 hours, 23 hours and 48 hours. The COWAT test was performed only at 2 hours and 23 hours to reduce practice effects. These scores were contrasted between three dosing conditions.

As shown in FIGS. 19 through 21, cognition data indicated that subjects given topiramate XR capsule formulations, 100 mg performed better than those tested with Topamax tablets, 100 mg. Significant differences were seen most clearly in the COWAT, SDMT and working memory. Although there was no consistent effect found for SDMT, the trend was same for both topiramate XR formulations over time. There was a significant pattern in improvement for the working memory. This deterioration of cognition functions data were supported by the spontaneous adverse events reported by subjects on Topamax tablets.

Single-Dose Pharmacokinetic/Cognition Study Comparing Topiramate Non-Bioadhesive Delayed XR Capsule, 200 mg (Example 20) with Topamax Tablets, 200 mg in Healthy Volunteers A single-dose, blind, two-way crossover study comparing the pharmacokinetics and tolerability of two topiramate containing formulations at 200 mg dose was carried out in 24 healthy volunteers i.e. PK in 12 subjects and cognition functions in 24 subjects. Four 25 mg Topamax tablets were encapsulated in each capsule and 2 capsules were administered as a single dose. Each subject received a single dose of each of the formulation in random order following a light breakfast and plasma levels of topiramate were measured using the LC/MS/MS. The doses were separated by 2-week washout period. FIG. 22 shows the topiramate plasma concentrations vs. time profiles demonstrating similar extent of exposure for both formulations but reduced inter-subject variability for the XR formulation. In addition to PK testing, the cognition profiles of various topiramate formulations were also tested using a battery of neuropsychological tests as outlined in Example 20. As shown in FIGS. 23 through 26, cognition data indicated that subjects given topiramate XR capsule formulations, 200 mg performed better than those tested with Topamax tablets, 200 mg in all the tests.

Example 21: Topiramate Delayed Extended Release Capsule Comprising Layered Pellets, 200 mg Table 25 specifies the composition of topiramate XR capsule, 200 mg in which the immediate release topiramate component outlined in previous examples was layered onto the Eudragit RL-100/RS-100 coated pellets.

A dosage form was manufactured as follows beginning with the first drug composition. First 818 g of microcrystalline cellulose, 700 g of topiramate, 234 g of sodium lauryl sulfate and 148 g of dibasic sodium phosphate were mixed in high shear granulator (Pharmx, Fluid Air with 8 L product bowl) for 6 minutes at a mixing speed of 100 rpm. The dry mixture was then sprayed with a binder solution of hydroxypropyl cellulose in purified water with continuous mixing. The granulation was then extruded into rods using a Twin dome extruder (LCI Corporation) equipped with a 0.8 mm screen. The extruded rods were fed into the spheronizer (LCI corporation) equipped with a cross-hatched plate and spheronized at 1000 rpm, to produce multiparticulate cores. The cores were dried in the fluidized bed unit at 50° C. for 150 minutes.

These multiparticulate cores were coated with release rate controlling polymers, Eudragit RS-100 and Eudragit RL-100 using a Vector MFL01 laboratory fluid bed coater. A coating composition containing 14.1 g of Eudragit RS-100, 14.1 g of Eudragit RL-100, 1.5 g of triethyl citrate and 0.3 g of Aerosil, dispersed in 600 mL of ethanol solution containing 30 g of purified water, was sprayed onto the cores using the following process parameters: inlet temperature=30-32° C.; atomization pressure=18-20 psi; coating solution feed rate=20 rpm; fluidization air=150-230 L/min.

Multiparticulate beads coated with Eudragit RS-100/Eudragit RL-100 polymer were subsequently applied with second drug composition. 37.5 g of topiramate, 2.5 g of PEG-8000 and 10.0 g of hydroxypropyl cellulose SSL were added to 50 mL of purified water and mixed until a uniform dispersion was formed. The suspension was then applied onto the beads in the Vector MFL01 laboratory fluid bed coater using the coating parameters mentioned above with the exception that inlet temperature was maintained at 40° C.

The topiramate beads coated with second drug composition were then applied with Opadry II (85F19250) moisture barrier coating composition in the Vector MFL01 laboratory fluid bed coater. Opadry II-coated multiparticulate beads containing 200 mg topiramate, were encapsulated in size "00" capsules. The filled capsules were subsequently applied with a seal coating of Opadry Clear (03K19229) (10% w/w) and an enteric coating of Acryl-EZE Clear (93F19255) (20% w/w) in the Labcoat M pan coater. A seal coating composition containing 50 g of Opadry Clear (03K19229) was dissolved in a mixture of 394.5 g of dehydrated alcohol and 55.6 g of purified water. Similarly an enteric coating suspension containing 75 g of Acryl-EZE Clear (93F19255), 25 g of triethyl citrate was prepared in a mixture of 336.9 g of dehydrated alcohol and 62.5 g of purified water. The following coating parameters were used: pump speed=9.0; inlet air temperature=42° C.; exhaust temperature=33-34° C.; atomization air pressure=17-18 psi; air volume=65-70 cfm and pan speed of 23-30 rpm.

Enteric-coated capsules were tested for dissolution in USP II apparatus at 50 rpm. The capsules were stirred in 900 mL of 0.1 N HCl for 2 hrs and subsequently transferred into phosphate buffer, pH 6.8 for 24 hours at 37° C. Capsules did not dissolve during 2 hours of testing period in 0.1 N HCl and remained intact. The release profile for the capsules as given in FIG. 27 demonstrated a controlled release profile releasing 45% of drug at 2 hrs, 75% at 4 hrs and greater than 85% at 6 hrs.

TABLE 25

Unit Dose Compositions of Topiramate XR Capsule, 200 mg

| Components | Function | Amount (% w/w) |
|---|---|---|
| Topiramate | Active | 23.1 |
| Microcrystalline Cellulose | Spheronization aid | 21.6 |
| Hydroxypropyl Cellulose | Binder | 3.9 |
| Dibasic Sodium Phosphate | Solubilizer | 3.9 |
| Sodium Lauryl Sulfate | Surfactant | 6.2 |
| Ammonio Methacrylate Copolymer, Type A (Eudragit ® RL 100) | Release rate controlling polymer | 1.8 |
| Ammonio Methacrylate Copolymer, Type B (Eudragit ® RS 100) | Release rate controlling polymer | 1.8 |
| Colloidal Silicon Dioxide | Glidant | 0.1 |
| Triethyl Citrate | Plasticizer | 3.8 |
| Polyethylene Glycol 8000 | Plasticizer, pore former | 0.3 |
| Opadry ® II (85F19250) | Moisture barrier coating | 3.5 |
| Opadry ® Clear (03K19229) | Film Former, seal coating | 6.2 |
| Acryl-EZE ™ Clear (93F19255) | Enteric coating | 10.6 |
| Gelatin (hard gelatin capsule, size 00) | Carrier | 13.2 |
| Water, Purified | Solvent | * |
| Ethanol (Dehydrated Alcohol) | Solvent | * |
| Total | | 100.0 |

* Solvents used as process aid, removed during processing

Example 22: Topiramate Delayed Release, Sprinkle Bead Capsule

Example 22 defines the composition of topiramate immediate-release coating applied onto the sugar sphere beads as well as enteric coating applied onto the topiramate coated beads to form topiramate delayed-release, sprinkle bead capsule. The advantage of this formulation is that enteric-coated topiramate beads can easily be sprinkled onto foods, such as apple sauce or jelly, and can thus be used for pediatric and geriatric subjects who may have difficulty taking capsules, tablets, and the like. The enteric coating not only protects the drug from breakdown in the stomach but also acts as a taste masking coating. The enteric coating also acts as a moisture barrier coating and provides improved stability to the drug.

TABLE 26

Composition of Topiramate Immediate Release (IR) Coating and Enteric Coating to form Topiramate Delayed Release Sprinkle Bead Capsule
Topiramate IR Coating

| Components | Desired Wt % | Desired Qty (g) |
|---|---|---|
| Topiramate (micronized) | 85 | 17.0 |
| PEG 8000 | 5 | 1.0 |

TABLE 26-continued

Composition of Topiramate Immediate Release (IR) Coating and Enteric Coating to form Topiramate Delayed Release Sprinkle Bead Capsule
Topiramate IR Coating

| Components | Desired Wt % | Desired Qty (g) |
|---|---|---|
| Hydroxypropyl cellulose SSL | 10 | 2.0 |
| P. Water* | — | 200.0 |
| Total Solids | 100 | 20.0 g |

*Removed during drying/coating process

Batch amount of each of the topiramate IR coating were accurately weighed out and suspended in purified water using a mixer. The batch quantity of sugar spheres (20-25 mesh), NF, were charged into the Vector MFL01 laboratory fluid bed coater and sprayed with topiramate suspension using the coating parameters mentioned above in Example 21. The core beads were dried at 60° C. for at least 15 minutes. The core beads were then sized through 16 mesh and 25 mesh screens to remove fine and agglomerates.

| Enteric Coating | | |
|---|---|---|
| Components | Desired Wt % | Desired Qty (g) |
| Acryl-Eze White (93018508) | 100 | 20.0 |
| Water* | — | 200.0 |
| Total Solids | 100 | 20.0 g |

*Removed during drying/coating process

The core beads were subsequently applied with AcrylEze™ White coating suspension in the Vector MFL01 laboratory fluid bed coater until a target weight gain of 10% was achieved.

The strengths of topiramate delayed-release sprinkle bead capsules, 15, 25, 50, 100 and 200 mg were obtained from a single formulation of topiramate enteric coated sprinkle beads by encapsulating the proportionate amounts of coated beads in appropriate sized and marked capsules.

Enteric-coated sprinkle beads were tested for dissolution in USP II apparatus at 50 rpm. The capsules were stirred in 900 mL of 0.1 N HCl for 2 hrs and subsequently transferred into phosphate buffer, pH 6.8 for 24 hours at 37° C. Beads remained intact during 2 hours of testing period in 0.1 N HCl and demonstrated completed drug release in pH 6.8 buffer in 30 minutes Although the micronized topiramate was layered onto the sugar spheres, various other particles such as cellulose spheres, microcrystalline cellulose, polymeric micro- or nanoparticles, various salt crystals (sodium chloride, dibasic sodium phosphate, etc.) can also be used as substrates.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A delayed-release oral pharmaceutical composition, comprising:
   (a) only one active agent, the active agent being selected from the group consisting of topiramate and pharmaceutically acceptable salts thereof,
   (b) particles having a core formulated as a matrix comprising the active agent coated with an enteric polymer coating
   or particles having a core coated with a layer comprising the active agent, and further coated with an enteric polymer coating,
   wherein the enteric polymer coating becomes soluble at a pH above 4.5 and delays the release of topiramate about 0.5 to about 4 hours.

2. The composition of claim 1, further comprising a release-controlling polymer selected from the group consisting of ammonio methacrylate copolymer, types A and B; ethylcellulose aqueous dispersions, hydroxyethyl cellulose, cellulose acetate, cellulose acetate butyrate, hydroxypropyl cellulose, hydroxypropyl methylcellulose, polyvinylpyrrolidone, polyvinylpyrrolidone/vinyl acetate copolymer, and any combination thereof.

3. The composition of claim 1, wherein the composition comprises two or more cores.

4. The composition of claim 3, wherein at least one core is formulated for immediate release (IR).

5. The composition of claim 3, wherein at least one core comprises a release-controlling polymer.

6. The composition of claim 3, comprising a first immediate release core and a second core coated with a release-controlling polymer.

7. The composition of claim 6, wherein the release-controlling polymer is selected from ammonio methacrylate copolymer, types A and B; ethylcellulose aqueous dispersions, hydroxyethyl cellulose, cellulose acetate, cellulose acetate butyrate, hydroxypropyl cellulose, hydroxypropyl methylcellulose, polyvinylpyrrolidone, polyvinylpyrrolidone/vinyl acetate copolymer, or any combination thereof.

8. The composition of claim 1, wherein the enteric coating is selected from cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride, ethyl methyacrylate-methylmethacrylate-chlorotrimethylammonium ethyl acrylate copolymer, natural resins, carboxymethyl ethylcellulose, co-polymerized methacrylic acid/methacrylic acid methyl esters, or any combination thereof.

9. The composition of claim 1, wherein the composition comprises micronized topiramate having a median particle size in the range of 1-250 microns.

10. The composition of claim 1, further comprising at least one basifying agent.

11. The composition of claim 1, further comprising a least one surfactant or co-surfactant.

12. The composition of claim 1 for once-a-day administration.

13. The composition of claim 1, wherein the matrix further comprises at least one pharmaceutically acceptable excipient selected from a group consisting of binding agents, bulking agents, and disintegrants.

14. The composition of claim 1, wherein at least one core is coated with an IR layer.

15. The composition of claim 1, wherein at least one core is coated with an extended release (XR) layer.

16. The composition of claim 3, wherein a first core is an immediate release core and a second core is coated with a release-controlling polymer.

17. The composition of claim 15, wherein the XR layer comprises a release-controlling polymer selected from the group consisting of ammonio methacrylate copolymer, types A and B; ethylcellulose aqueous dispersions, hydroxyethyl cellulose, cellulose acetate, cellulose acetate butyrate, hydroxypropyl cellulose, hydroxypropyl methylcellulose, polyvinylpyrrolidone, polyvinylpyrrolidone/vinyl acetate copolymer, and any combination thereof.

18. The composition of claim 1, wherein the particles are encapsulated in a gelatin capsule.

19. The composition of claim 1, wherein the particles are multiparticulate beads or pellets.

20. The composition of claim 19, wherein the multiparticulate beads or pellets are encapsulated in a gelatin capsule.

21. The composition of claim 1, wherein the Cmax produced by dosing the composition in vivo is higher by about 20% to about 80% of the Cmax of the same amount of topiramate administered as an immediate release composition.

22. The composition of claim 1, wherein the AUC produced by dosing the composition in vivo is higher by about 70% to about 140% of the AUC of the same amount of topiramate administered as an immediate release composition.

23. The composition of claim 1, wherein the weight of the enteric polymer coating is about 7% to about 13% of the weight of the composition.

24. The composition of claim 1, wherein the topiramate or a pharmaceutically acceptable salt thereof is present in an amount of about 15 mg to about 400 mg.

25. The composition of claim 8, wherein the natural resin is zein, shellac, or copal collophorium.

* * * * *